US007186699B2

(12) United States Patent
Harding et al.

(10) Patent No.: US 7,186,699 B2
(45) Date of Patent: Mar. 6, 2007

(54) METHOD FOR TREATING CANCER BY VECTOR-MEDIATED DELIVERY OF ONE OR MORE ANTI-ANGIOGENIC OR PRO-APOPTOTIC GENES

(75) Inventors: Thomas Harding, San Francisco, CA (US); Karin Jooss, Bellevue, WA (US); Alshad Lalani, San Francisco, CA (US); Brian Donahue, Los Altos, CA (US)

(73) Assignee: Cell Genesys, Inc., South San Francisco, CA (US)

( * ) Notice: Subject to any disclaimer, the term of this patent is extended or adjusted under 35 U.S.C. 154(b) by 17 days.

(21) Appl. No.: 10/855,559

(22) Filed: May 28, 2004

(65) Prior Publication Data

US 2005/0031593 A1 Feb. 10, 2005

Related U.S. Application Data

(60) Provisional application No. 60/475,006, filed on Jun. 3, 2003.

(51) Int. Cl.
*A61K 31/70* (2006.01)
*A01N 45/00* (2006.01)
*C12N 15/00* (2006.01)
*C12N 15/63* (2006.01)
*C07H 21/04* (2006.01)

(52) U.S. Cl. ............... 514/44; 435/455; 435/320.1
(58) Field of Classification Search ............... None
See application file for complete search history.

(56) References Cited

U.S. PATENT DOCUMENTS

| | | | |
|---|---|---|---|
| 5,436,146 A | 7/1995 | Shenk et al. | |
| 5,686,279 A | 11/1997 | Finer et al. | |
| 5,712,380 A | 1/1998 | Kendall et al. | |
| 5,736,129 A * | 4/1998 | Medenica et al. | 424/85.4 |
| 5,753,500 A | 5/1998 | Shenk et al. | |
| 5,872,005 A | 2/1999 | Wang et al. | |
| 5,955,311 A | 9/1999 | Rockwell et al. | |
| 5,994,106 A | 11/1999 | Kovesdi et al. | |
| 6,011,003 A | 1/2000 | Charnock-Jones et al. | |
| 6,040,183 A | 3/2000 | Ferrari et al. | |
| 6,093,570 A | 7/2000 | Ferrari et al. | |
| 6,127,175 A | 10/2000 | Vigne et al. | |
| 6,133,028 A | 10/2000 | Imler et al. | |
| 6,156,303 A | 12/2000 | Russell et al. | |
| 6,180,613 B1 | 1/2001 | Kaplitt et al. | |
| 6,287,814 B1 | 9/2001 | Hope et al. | |
| 6,503,888 B1 | 1/2003 | Kaplitt et al. | |
| 6,548,286 B1 | 4/2003 | Samulski et al. | |
| 6,780,409 B2 * | 8/2004 | During et al. | 424/93.2 |
| 2002/0168342 A1 | 11/2002 | Wang et al. | |
| 2003/0017977 A1 | 1/2003 | Xia et al. | |
| 2003/0228282 A1 | 12/2003 | Gao et al. | |
| 2004/0005684 A1 * | 1/2004 | Hung et al. | 435/191 |
| 2004/0057933 A1 | 3/2004 | Wilson et al. | |

FOREIGN PATENT DOCUMENTS

| | | |
|---|---|---|
| WO | WO 97/44453 | 11/1997 |
| WO | WO 98/13071 | 4/1998 |
| WO | WO 99/61066 | 12/1999 |
| WO | WO 00/75319 | 12/2000 |
| WO | WO 02/060489 | 8/2002 |

OTHER PUBLICATIONS

Verma et al. Gene Therapy: Twenty-first century medicine. Annu. Rev. Biochem. 74:711-738, 2005.*
Goncalves, M. A concise peer into the background, initial thoughts and practices of human gene therapy. BioEssays 27:506-517, 2005.*
Gardlik et al. Vectors and delivery systems in gene therapy. Med. Sci. Monit. 11(4):RA110-121, 2005.*
Altschul et al., "Basic Local Alignment Search Tool", J. Mol. Biol., 215:403-410 (1990).
Ashkenazi, "Targeting Death and Decoy Receptors of the Tumour-Necrosis Factor Superfamily", Nat. Rev. Cancer, 2:420-430 (2002).
Bergers et al., "Effects of Angiogenesis Inhibitors on Multistage Carcinogenesis in Mice", Science, 284:808-811 (1999).
Batzer et al., "Enhanced evolutionary PCR using oligonucleotides with inosine at the 3'-terminus", Nucleic Acids Res., 19:5081 (1991).
Bobo et al., "Convection-enhanced delivery of macromolecules in the brain", PNAS, 91(6):2076-2080 (1994).
Bossis and Chiorini, "Cloning of an Avian Adeno-Associated Virus (AAAV) and Generation of Recombinant AAAV Particles", J. Virol, 77(12):6799-6810 (2003).
Byrne et al., "Vascular Endothelial Growth Factor-Trap Decreases Tumor Burden, Inhibits Ascites, and Causes Dramatic Vascular Remodeling in an Ovarian Cancer Model", Clin. Can. Res., 9:5721-5728 (2003).
Capecchi, "High Efficiency Transformation by Direct Microinjection of DNA into Cultured Mammalian Cells", Cell, 22:479-488 (1980).
Chiorini et al., "Cloning and Characterization of Adeno-Associated Virus Type 5", J. Virol., 73(2):1309-1319 (1999).
Cunningham et al., "Distribution of AAV-TK Following Intracranial Convection-Enhanced Delivery Into Rats", Cell Transplantation, vol. 9:585-594 (2000).

(Continued)

*Primary Examiner*—Quang Nguyen
(74) *Attorney, Agent, or Firm*—DLA Piper US LLP

(57) ABSTRACT

The present invention provides therapeutic compositions and methods for vector-mediated delivery and in vivo expression of polynucleotides encoding anti-cancer compounds that are effective in the treatment of cancer. In particular, the invention relates to the use of recombinant viral and non-viral vectors to deliver genes encoding one or more anti-angiogenic or proapoptotic gene products for the treatment of cancer.

15 Claims, 34 Drawing Sheets

OTHER PUBLICATIONS

Davidson et al., "Recombinant adeno-associated virus type 2, 4, and 5 vectors" Transduction of variant cell types and regions in the mammalian central nervous system, PNAS, 97(7):3428-3432 (2000).

Donnelly et al., "The cleavage activities of aphthovirus and cardiovirus 2A proteins", J. Gen. Virol., 78:13-21 (1997).

Dull et al., "A Third-Generation Lentivirus Vector with a Conditional Packaging System", J. Virology, 72(11):8463-8471 (1998).

Felgner et al., "Lipofection: A highly efficient, lipid-mediated DNA-transfection procedure", Proc. Natl. Acad. Sci. USA, 84:7413-7417 (1987).

Furler et al., "Recombinant AAV vectors containing the foot and mouth disease virus 2A sequence confer efficient bicistronic gene expression in cultured cells and rat substantia nigra neurons", Gene Therapy, 8(11):864-873 (2001).

Gao et al., "Novel adeno-associated viruses from rhesus monkeys as vectors for human gene therapy", PNAS, 99(18):11854-11859 (2002).

Gao et al., "Adeno-associated viruses undergo substantial evolution in primates during natural infections", PNAS, 100(10):6081-6086 (2003).

Gengrinovitch et al., "Platelet Factor-4 Inhibits the Mitogenic Activity of $VEGF_{121}$ and $VEGF_{165}$ Using Several Concurrent Mechanisms", J. Biol. Chem., 270:15059-15065 (1995).

Griscelli et al., "Angiostatin gene transfer: Inhibition of tumor growth in vivo by blockage of endothelial cell proliferation associated with a mitosis arrest", Proc. Natl. Acad. Sci. USA, 95(11):6367-6372 (1998).

Guo et al., "Evaluation of promoter strength for hepatic gene expression in vivo following adenovirus-mediated gene transfer", Gene Ther., 3(9):802-810 (1996).

Hagedorn et al., "Domain Swapping in a COOH-terminal Fragment of Platelet Factor 4 Generates Potent Angiogenesis Inhibitors" Cancer Research, 62(23):6884-6890 (2002).

Halbert et al., "Repeat Transduction in the Mouse Lung by Using Adeno-Associated Virus Vectors with Different Serotypes", Journal of Virology, 74(3):1524-1532 (2000).

Hanahan et al., "Heritable formation of pancreatic β-cell tumours in transgenic mice expressing recombinant insulin/simian virus 40 oncogenes", Nature, 315(6015):115-122 (1985).

Harbury et al., "A Switch Between Two-, Three-, and Four-Stranded Coiled Coils in GCN4 Leucine Zipper Mutants", Science, 262:1401-1407 (1993).

Hartley et al., "Naturally Occurring Murine Leukemia Viruses in Wild Mice: Characterization of a New "Amphotropic" Class", J. Virol., 19:19-25 (1976).

Hiraga et al., "The Bisphosphonate Ibandronate Promotes Apoptosis in MDA-MB-231 Human Breast Cancer Cells in Bone Metastases", Cancer Res., 61(11):4418-4424 (2001).

Holash et al., "VEGF-Trap: A VEGF blocker with potent antitumor effects", PNAS, 99(17):11393-11398 (2002).

Horoszewicz et al., "LNCaP Model of Human Prostatic Carcinoma", Cancer Res., 43(4):1809-1818 (1983).

Huang, et al., "Regression of established tumours and metastases by potent vascular endothelial growth factor blockade", Proc. Nat. Acad. Sci. USA, 100(13):7785-7790 (2003).

Kim et al, "Use of the human elongation factor 1α promoter as a versatile and efficient expression system", Gene, 91(2):217-223 (1990).

Kim et al., "Potent VEGF blockage causes regression of coopted vessels in a model of neuroblastoma", Proc. Nat. Acad. Sci. USA, 99(17):11399-11404 (2002).

Lin et al., "Inhibition of Tumor Growth by Targeting Tumor Endothelium Using a Soluble Vascular Endothelial Growth Factor Receptor", Cell Growth Differ., 9(1):49-58 (1998).

Liu et al., "Hydrodynamics-based transfection in animals by systemic administration of plasmid DNA", Gene Ther., 6:1258-1266 (1999).

Lucas et al., "Multiple Forms of Angiostatin Induce Apoptosis in Endothelial Cells", Blood, 92(12):4730-4741 (1998).

Maione et al., "Inhibition of Angiogenesis by Recombinant Human Platelet Factor-4 and Related Peptides", Science, 237:77-79 (1990).

Mannino et al., "Liposome Mediated Gene Transfer", Bio Techn., 6:682-690 (1988).

McCarty et al., "Self-complementary recombinant adeno-associated virus (scAAV) vectors promoter efficient transduction independently of DNA synthesis", Gene Ther., 8(16):1248-1254 (2001).

Miller, "Human gene therapy comes of age", Nature, 357:455-460 (1992).

Mulligan et al., "Expression of a Bacterial Gene in Mammalian Cells", Science, 209:1422-1427 (1980).

Nguyen et al., "Convection-enhanced delivery of AAV-2 combined with heparin increases TK gene transfer in the rat brain", Neuroreport, 12(9):1961-1964 (2001).

Niwa et al., "Efficient selection for high-expression transfectants with a novel eukaryotic vector", Gene, 108(2):193-199 (1991).

No et al., "Ecdysone-inducible gene expression in mammalian cells and transgenic mice", Proc. Nat. Acad. Sci., 93:3346 (1996).

Ohtsuka et al, "An Alternative Approach to Deoxyoligonucleotides as Hybridization Probes by Insertion of Deoxyinosine at Ambiguous Codon Positions", J. Biol. Chem., 260:2605-2608 (1985).

Ory et al., "A stable human-derived packaging cell line for production of high titer retrovirus/vesicular stomatitis virus G pseudodtypes", Proc. Natl. Acad. Sci., 93:11400-11406 (1996).

Osterwalder et al., "A conditional tissue-specific transgene expression system using inducible GAL4", Proc. Natl. Acad. Sci., 98(22):12596-12601 (2001).

Passini et al., "Intraventricular Brain Injection of Adeno-Associated Virus Type 1 (AAV1) in Neonatal Mice Results in Complementary Patterns of Neuronal Transduction to AAV2 and Total Long-Term Correction of Storage Lesions in the Brains of β-Glucuronidase-Deficient Mice", J. Virology, 77(12):7034-7040, (2003).

Pearson, et al., "Improved tools for biological sequence comparison", Proc. Nat'l. Acad. Sci. USA, 85:2444 (1988).

Perollet, "Platelet Factor 4 Modulates Fibroblast Growth Factor 2 (FGF-2) Activity and Inhibits FGF-2 Dimerization", Blood, 91:3289-3299 (1998).

Remington's Pharmaceutical Sciences, 18th Edition, A. Gennaro, ed., Mack Publishing Co., Easton, PA (1990).

Ryan et al., "Cleavage of foot-and-mouth disease virus polyprotein is mediated by residues located within a 19 amino acid sequence", J. Gen. Virol. 72:2727-2732 (1991).

Sambrook et al., Molecular Cloning: A Laboratory Manual (Second Edition), Cold Spring Harbor Press, Plainview, NY (1989).

Shigekawa et al., "Electroporation of Eukaryotes and Prokaryotes: A General Approach to the ntroduction of Macromolecules into Cells", BioTechn., 6:742-751(1988).

Smith et al., "Comparison of Biosequences", Adv. Appl. Math., 2:482 (1981).

Sugden et al., "A Vector That Replicates as a Plasmid and Can Be Efficiently Selected in B-lymphoblasts Transformed by Epstein-Barr Virus", Mol. Cell Biol., 5(2):410-413 (1985).

Suhr et al., "High level transactivation by a modified Bombyx ecdysone receptor in mammalian cells without exogenous retinoid X receptor", Proc. Nat. Acad. Sci., 95:7999 (1998).

Vakharia et al., "Proteolytic Processing of Foot-and-Mouth Disease Virus Polyproteins Expressed in a Cell-Free System from Clone-Derived Transcript", J. Virol., 61:3199-3207 (1987).

Walczak et al., "Tumoricidal activity of tumor necrosis factor-related apoptosis-inducing ligand in vivo", Nat. Med., 5:157-163 (1999).

Wu et al., "Regression of Human Mammary Adenocarcinoma by Systemic Administration of a Recombinant Gene Encoding the hFlex-TRAIL Fusion Protein", Molecular Therapy, 3(3):368-374 (2001).

Ye et al., "Regulated Delivery of Therapeutic Proteins After in Vivo Somatic Cell Gene Transfer", Science, 283:88-91 (2000).

Zhang et al., "High Levels of Foreign Gene Expression in Hepatocytes after Tail Vein Injection of Naked Plasmid DNA", Human Gene Ther., 10:1735-1737 (1999).

Zufferey et al., "Self-Inactivating Lentivirus Vector for Safe and Efficient In Vivo Gene Delivery", J. Virology, 72(12):9873-9880 (1998).

* cited by examiner

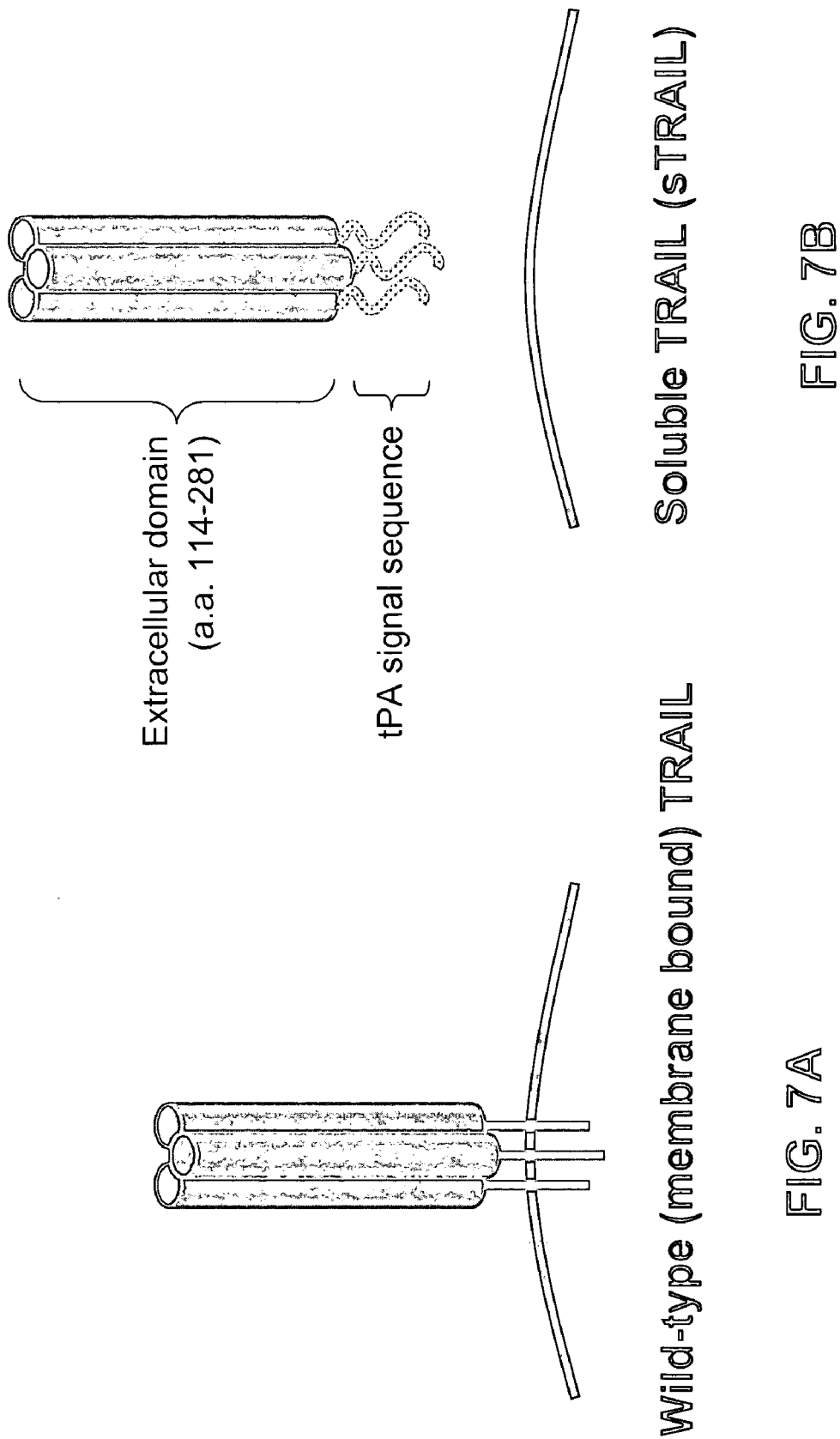

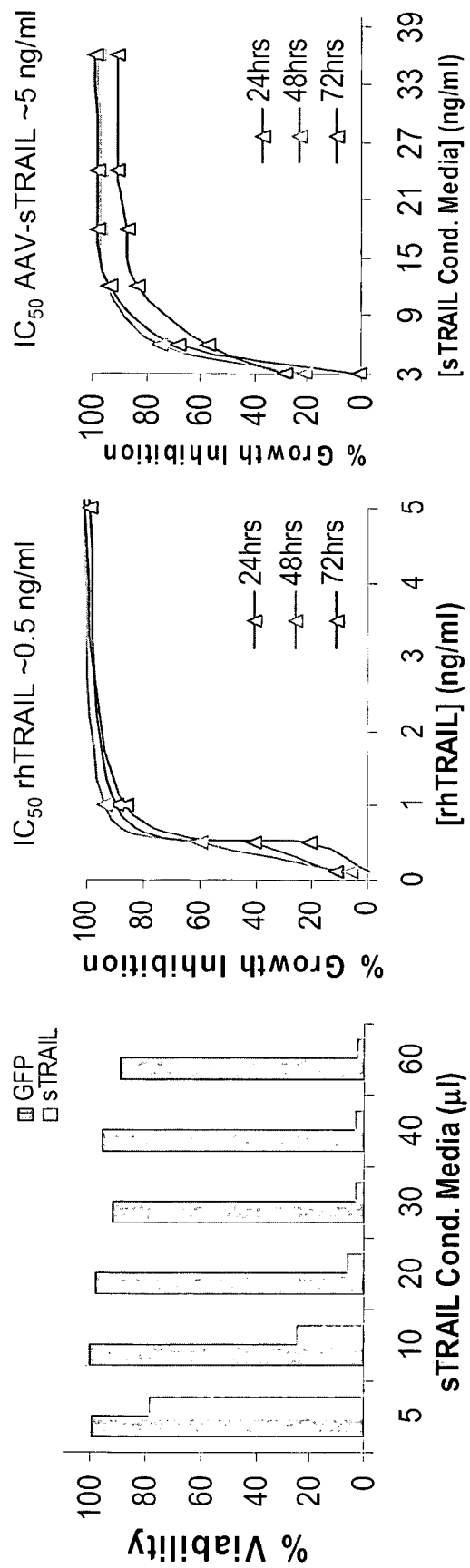

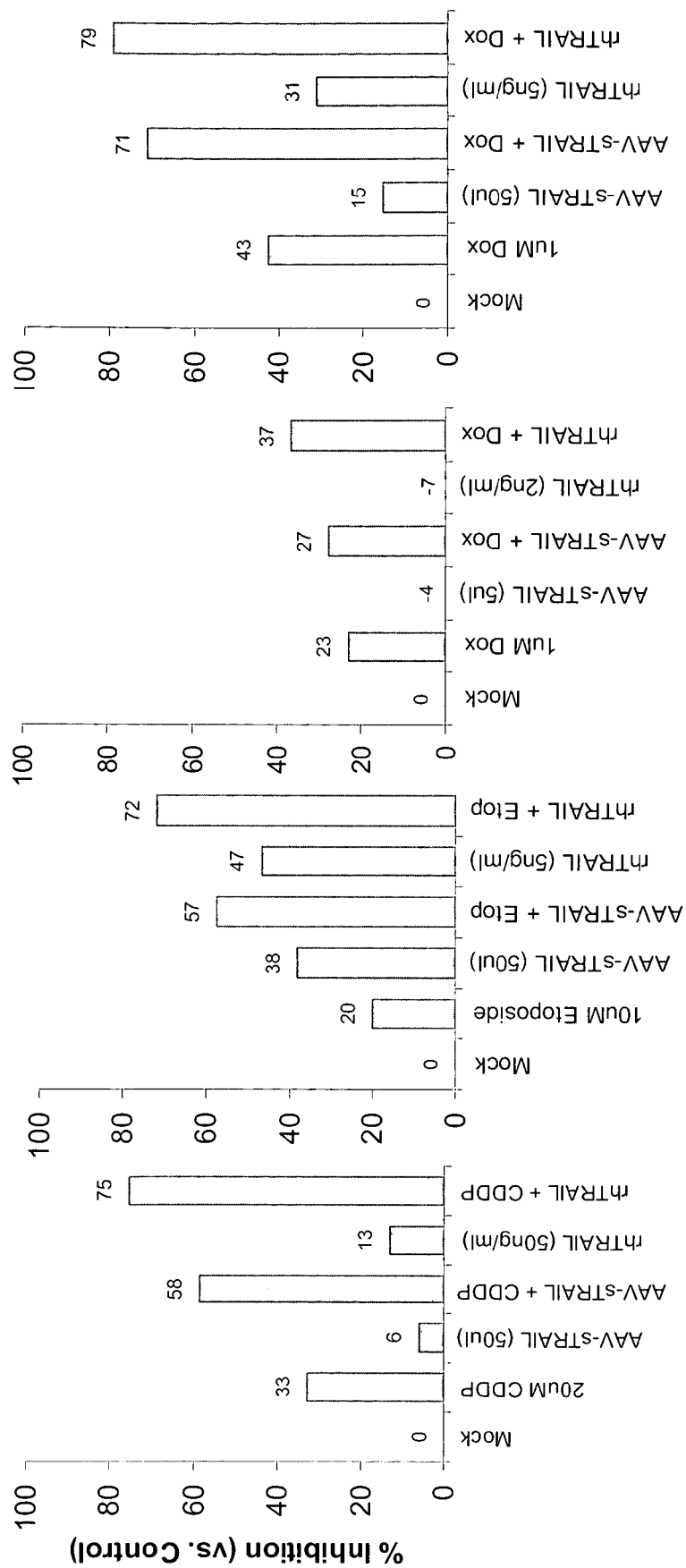

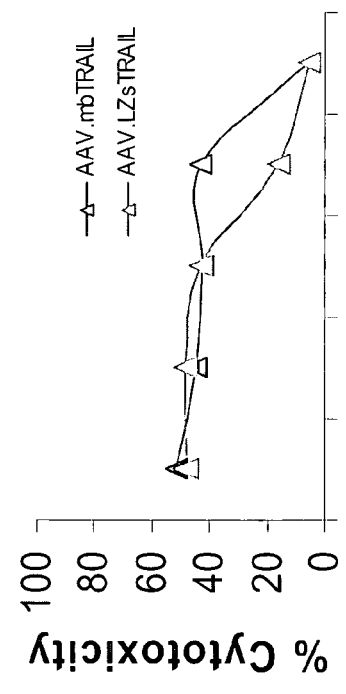
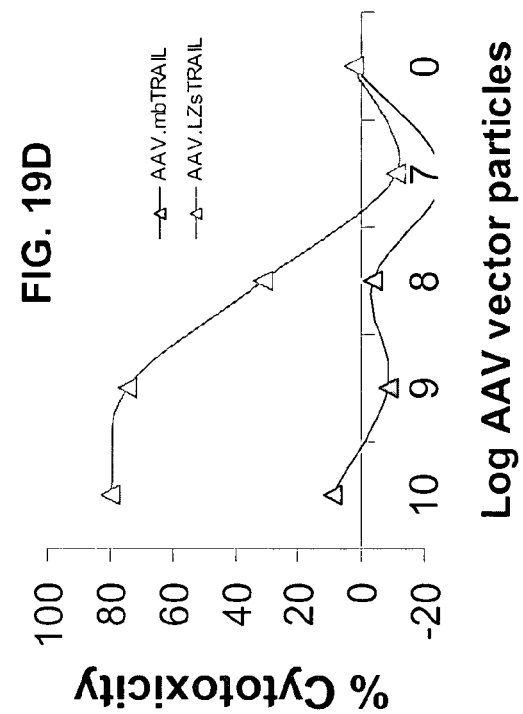
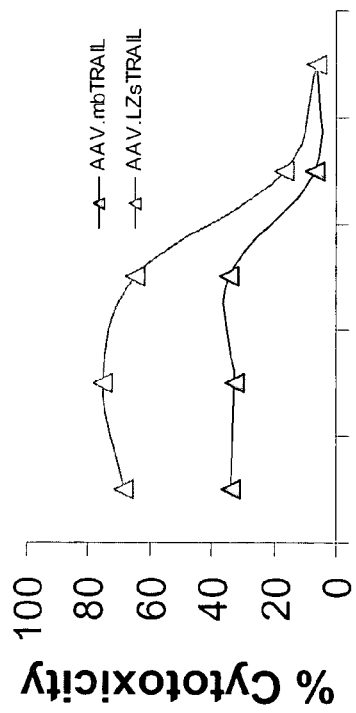
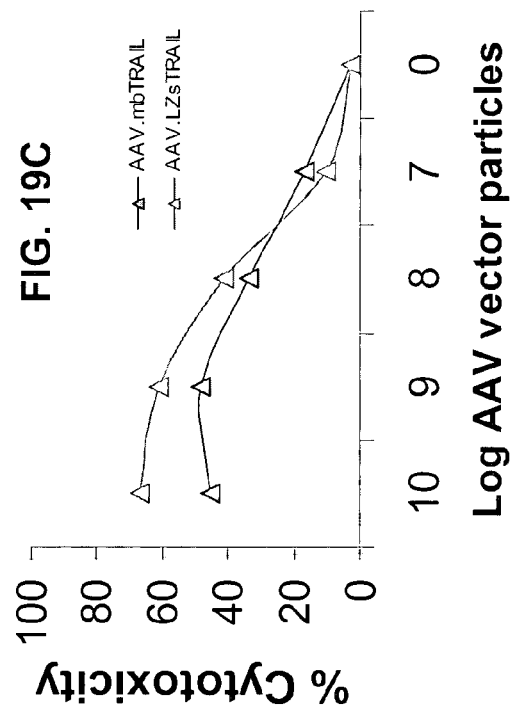
FIG. 19A  FIG. 19B  FIG. 19C  FIG. 19D
FIG. 19

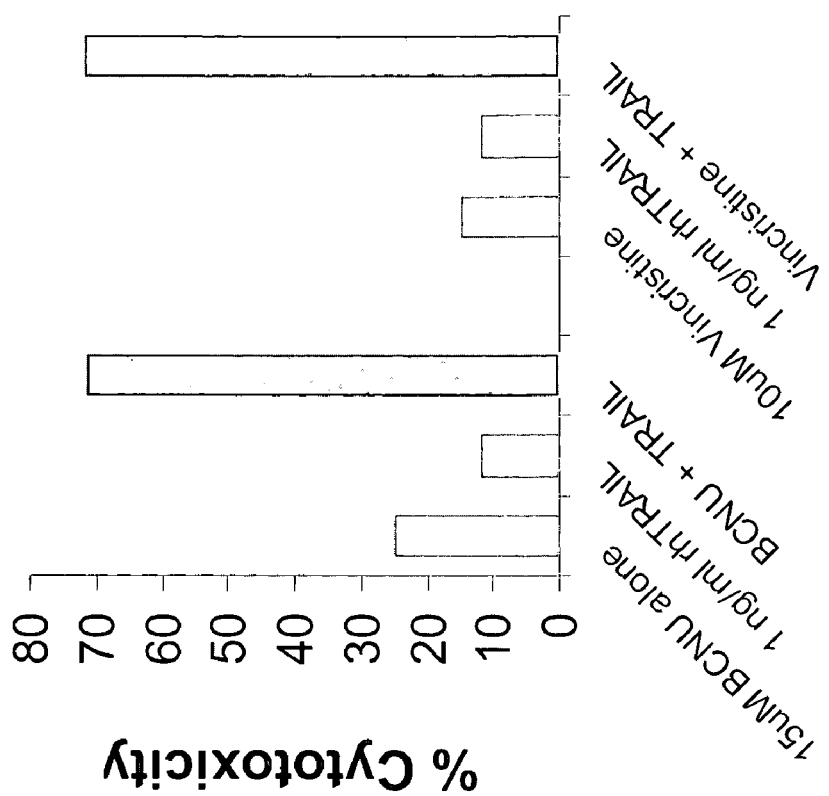
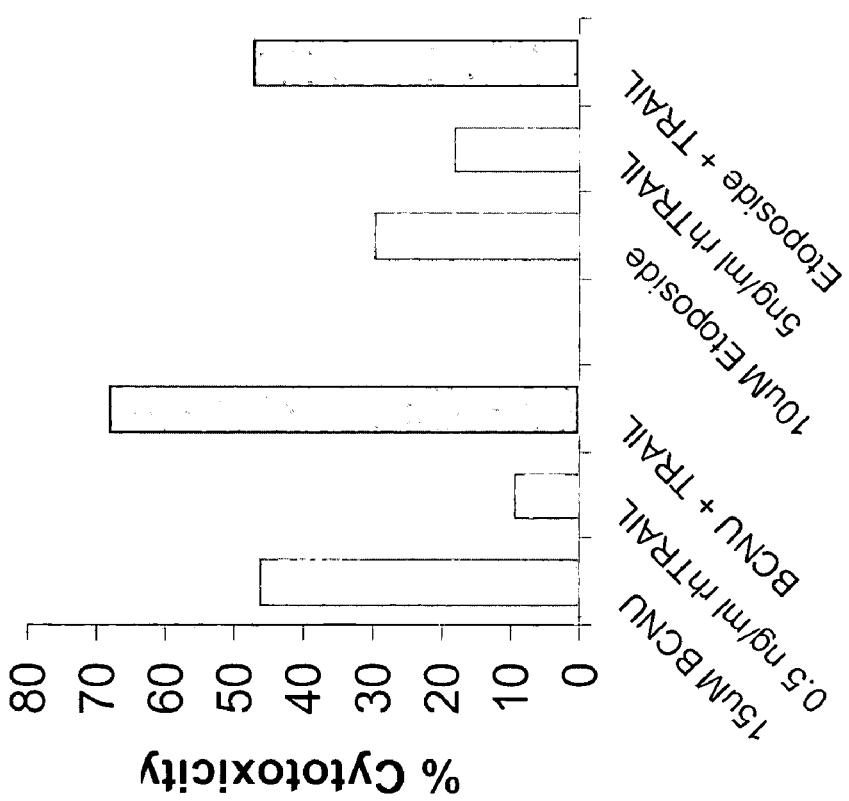
FIG. 22B
FIG. 22A

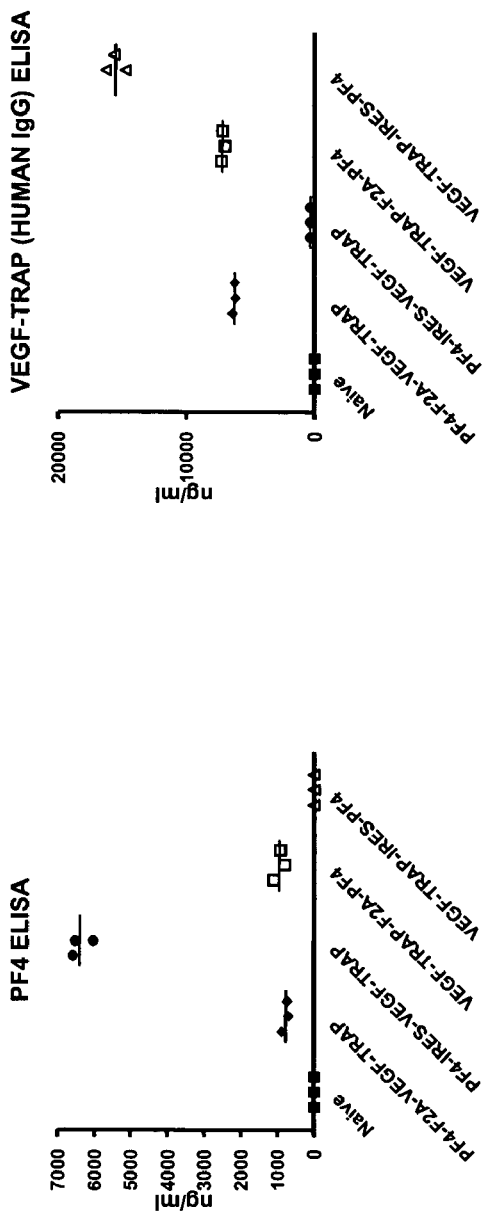
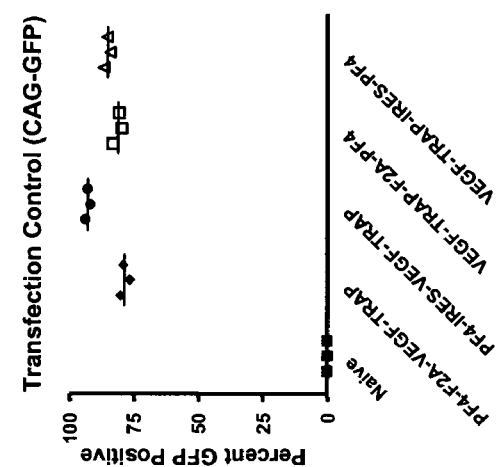
Fig. 34A
Fig. 34B
Fig. 34C

SEQUENCE LISTING

<160> NUMBER OF SEQ ID NOS: 30

<210> SEQ ID NO 1
<211> LENGTH: 846
<212> TYPE: DNA
<213> ORGANISM: Homo sapien

<400> SEQUENCE: 1

```
atggctatga tggaggtcca gggggaccc  agcctgggac agacctgcgt gctgatcgtg      60
atctttacag tgctcctgca gtctctctgt gtggctgtaa cttacgtgta ctttaccaac     120
gagctgaagc agatgcagga caagtactcc aaaagtggca ttgcttgttt cttaaaagaa     180
gatgacagtt attgggaccc caatgacgaa gagagtatga acagcccctg ctggcaagtc     240
aagtggcaac tccgtcagct cgttagaaag atgattttga gaacctctga ggaaaccatt     300
tctacagttc aagaaaagca acaaaatatt tctcccctag tgagagaaag aggtcctcag     360
agagtagcag ctcacataac tgggaccaga ggaagaagca acacattgtc ttctccaaac     420
tccaagaatg aaaaggctct gggccgcaaa ataaactcct gggaatcatc aaggagtggg     480
cattcattcc tgagcaactt gcacttgagg aatggtgaac tggtcatcca tgaaaaaggg     540
ttttactaca tctattccca acatactttt cgatttcagg aggaaataaa agaaacacac     600
```

```
aagaacgaca acaaatggt ccaatatatt tacaaataca caagttatcc tgaccctata    660
ttgttgatga aaagtgctag aaatagttgt tggtctaaag atgcagaata tggactctat    720
tccatctatc aaggggggaat atttgagctt aaggaaaatg acagaatttt tgtttctgta    780
acaaatgagc acttaataga catggaccat gaagccagtt ttttcggggc ctttttagtt    840
ggctaa                                                                846
```

<210> SEQ ID NO 2
<211> LENGTH: 281
<212> TYPE: PRT
<213> ORGANISM: Homo sapien

<400> SEQUENCE: 2

```
Met Ala Met Met Glu Val Gln Gly Gly Pro Ser Leu Gly Gln Thr Cys
  1               5                  10                  15

Val Leu Ile Val Ile Phe Thr Val Leu Leu Gln Ser Leu Cys Val Ala
                 20                  25                  30

Val Thr Tyr Val Tyr Phe Thr Asn Glu Leu Lys Gln Met Gln Asp Lys
             35                  40                  45

Tyr Ser Lys Ser Gly Ile Ala Cys Phe Leu Lys Glu Asp Asp Ser Tyr
         50                  55                  60

Trp Asp Pro Asn Asp Glu Glu Ser Met Asn Ser Pro Cys Trp Gln Val
 65                  70                  75                  80

Lys Trp Gln Leu Arg Gln Leu Val Arg Lys Met Ile Leu Arg Thr Ser
                 85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280
```

<210> SEQ ID NO 3
<211> LENGTH: 689
<212> TYPE: DNA
<213> ORGANISM: Homo sapien

```
<400> SEQUENCE: 3
catggatgca atgaagagag ggctctgctg tgtgctgctg ctgtgtggag cagtcttcgt    60
ttcgccgtcc ggcatgaagc agatcgagga caaaattgag gaaatccttt cgaagattta   120
ccacatcgag aacgagatcg cccggattaa gaagcttatt ggcgagaggg aaggatccgg   180
tgtgagagaa agaggtcctc agagagtagc agctcacata actgggacca gaggaagaag   240
caacacattg tcttctccaa actccaagaa tgaaaaggct ctgggccgca aaataaactc   300
ctgggaatca tcaaggagtg ggcattcatt cctgagcaac ttgcacttga ggaatggtga   360
actggtcatc catgaaaaag gttttactac catctattcc caaacatact ttcgatttca   420
ggaggaaata aaagaaaaca caagaacga caaacaaatg gtccaatata tttacaaata   480
cacaagttat cctgacccta tattgttgat gaaaagtgct agaaatagtt gttggtctaa   540
agatgcagaa tatggactct attccatcta tcaaggggga atatttgagc ttaaggaaaa   600
tgacagaatt tttgtttctg taacaaatga gcacttgata gacatggacc atgaagccag   660 tttttttcggg gcctttttag ttggctaag                                    689

<210> SEQ ID NO 4
<211> LENGTH: 228
<212> TYPE: PRT
<213> ORGANISM: Homo sapien

<400> SEQUENCE: 4

Met Asp Ala Met Lys Arg Gly Leu Cys Cys Val Leu Leu Cys Gly
  1               5                  10                  15

Ala Val Phe Val Ser Pro Ser Gly Met Lys Gln Ile Glu Asp Lys Ile
             20                  25                  30

Glu Glu Ile Leu Ser Lys Ile Tyr His Ile Glu Asn Glu Ile Ala Arg
         35                  40                  45

Ile Lys Lys Leu Ile Gly Glu Arg Glu Gly Ser Gly Val Arg Glu Arg
     50                  55                  60

Gly Pro Gln Arg Val Ala Ala His Ile Thr Gly Thr Arg Gly Arg Ser
 65                  70                  75                  80

Asn Thr Leu Ser Ser Pro Asn Ser Lys Asn Glu Lys Ala Leu Gly Arg
                 85                  90                  95

Lys Ile Asn Ser Trp Glu Ser Ser Arg Ser Gly His Ser Phe Leu Ser
            100                 105                 110

Asn Leu His Leu Arg Asn Gly Glu Leu Val Ile His Glu Lys Gly Phe
        115                 120                 125

Tyr Tyr Ile Tyr Ser Gln Thr Tyr Phe Arg Phe Gln Glu Glu Ile Lys
    130                 135                 140

Glu Asn Thr Lys Asn Asp Lys Gln Met Val Gln Tyr Ile Tyr Lys Tyr
145                 150                 155                 160

Thr Ser Tyr Pro Asp Pro Ile Leu Leu Met Lys Ser Ala Arg Asn Ser
                165                 170                 175

Cys Trp Ser Lys Asp Ala Glu Tyr Gly Leu Tyr Ser Ile Tyr Gln Gly
            180                 185                 190

Gly Ile Phe Glu Leu Lys Glu Asn Asp Arg Ile Phe Val Ser Val Thr
        195                 200                 205

Asn Glu His Leu Ile Asp Met Asp His Glu Ala Ser Phe Phe Gly Ala
    210                 215                 220

Phe Leu Val Gly
225
```

-continued

<210> SEQ ID NO 5
<211> LENGTH: 33
<212> TYPE: PRT
<213> ORGANISM: Homo sapien

<400> SEQUENCE: 5

Met Lys Gln Ile Glu Asp Lys Ile Glu Ile Leu Ser Lys Ile Tyr
1               5                   10                  15

His Ile Glu Asn Glu Ile Ala Arg Ile Lys Lys Leu Ile Gly Glu Arg
            20                  25                  30

Glu

<210> SEQ ID NO 6
<211> LENGTH: 306
<212> TYPE: DNA
<213> ORGANISM: Artificial Sequence
<220> FEATURE:
<223> OTHER INFORMATION: platelet factor-4

<400> SEQUENCE: 6
atgagctccg cagccgggtt ctgcgcctca cgccccgggc tgctgttcct ggggttgctg      60
ctcctgccac ttgtggtcgc cttcgccagc gctgaagctg aagaagatgg ggacctgcag     120
tgcctgtgtg tgaagaccac ctcccaggtc cgtcccaggc acatccagc cctggaggtg      180 atcaaggccg accccactg ccccactgcc caactgatag ccacgctgaa gaatggaagg      240
aaaatttgct tggacctgca agccccgctg tacaagaaaa taattaagaa acttttggag     300
agttag                                                                306

<210> SEQ ID NO 7
<211> LENGTH: 101
<212> TYPE: PRT
<213> ORGANISM: Artificial Sequence
<220> FEATURE:
<223> OTHER INFORMATION: platelet factor-4

<400> SEQUENCE: 7

Met Ser Ser Ala Ala Gly Phe Cys Ala Ser Arg Pro Gly Leu Leu Phe
1               5                   10                  15

Leu Gly Leu Leu Leu Leu Pro Leu Val Val Ala Phe Ala Ser Ala Glu
            20                  25                  30

Ala Glu Glu Asp Gly Asp Leu Gln Cys Leu Cys Val Lys Thr Thr Ser
        35                  40                  45

Gln Val Arg Pro Arg His Ile Thr Ser Leu Glu Val Ile Lys Ala Gly
    50                  55                  60

Pro His Cys Pro Thr Ala Gln Leu Ile Ala Thr Leu Lys Asn Gly Arg
65                  70                  75                  80

Lys Ile Cys Leu Asp Leu Gln Ala Pro Leu Tyr Lys Lys Ile Ile Lys
                85                  90                  95

Lys Leu Leu Glu Ser
            100

<210> SEQ ID NO 8
<211> LENGTH: 306
<212> TYPE: DNA
<213> ORGANISM: Artificial Sequence
<220> FEATURE:
<223> OTHER INFORMATION: platelet factor-4 with DLR mutation

<400> SEQUENCE: 8

```
atgagctccg cagccgggtt ctgcgcctca cgccccgggc tgctgttcct ggggttgctg      60
ctcctgccac ttgtggtcgc cttcgccagc gctgaagctg aagaagatgg ggacctgcag     120
tgcctgtgtg tgaagaccac ctcccaggtc cgtcccaggc acatcaccag cctggaggtg     180
atcaaggccg gacccactg ccccactgcc caactgatag ccacgctgaa gaatggaagg     240
aaaatttgct tggacctgcg agccccgctg tacaagaaaa taattaagaa acttttggag     300
agttag                                                               306
```

<210> SEQ ID NO 9
<211> LENGTH: 101
<212> TYPE: PRT
<213> ORGANISM: Artificial Sequence
<220> FEATURE:
<223> OTHER INFORMATION: platelet factor-4 with DLR mutation

<400> SEQUENCE: 9

```
Met Ser Ser Ala Ala Gly Phe Cys Ala Ser Arg Pro Gly Leu Leu Phe
1               5                   10                  15

Leu Gly Leu Leu Leu Leu Pro Leu Val Val Ala Phe Ala Ser Ala Glu
            20                  25                  30

Ala Glu Glu Asp Gly Asp Leu Gln Cys Leu Cys Val Lys Thr Thr Ser
        35                  40                  45

Gln Val Arg Pro Arg His Ile Thr Ser Leu Glu Val Ile Lys Ala Gly
    50                  55                  60

Pro His Cys Pro Thr Ala Gln Leu Ile Ala Thr Leu Lys Asn Gly Arg
65                  70                  75                  80

Lys Ile Cys Leu Asp Leu Arg Ala Pro Leu Tyr Lys Lys Ile Ile Lys
                85                  90                  95

Lys Leu Leu Glu Ser
            100
```

<210> SEQ ID NO 10
<211> LENGTH: 50
<212> TYPE: DNA
<213> ORGANISM: Artificial Sequence
<220> FEATURE:
<223> OTHER INFORMATION: PCR forward primer for PF4(DLR)

<400> SEQUENCE: 10

```
ggaaaatttg cttggacctg cgagccccgc tgtacaagaa aataattaag                 50
```

<210> SEQ ID NO 11
<211> LENGTH: 50
<212> TYPE: DNA
<213> ORGANISM: Artificial Sequence
<220> FEATURE:
<223> OTHER INFORMATION: PCR reverse primer for PF4(DLR)

<400> SEQUENCE: 11

```
cttaattatt ttcttgtaca gcggggctcg caggtccaag caaattttcc                 50
```

<210> SEQ ID NO 12
<211> LENGTH: 1377
<212> TYPE: DNA
<213> ORGANISM: Artificial Sequence
<220> FEATURE:
<223> OTHER INFORMATION: VEGF-TRAP

<400> SEQUENCE: 12

```
atggtcagct actgggacac cggggtcctg ctgtgcgcgc tgctcagctg tctgcttctc      60
```

-continued

```
acaggatcta gttccggagg tagacctttc gtagagatgt acagtgaaat ccccgaaatt    120
atacacatga ctgaaggaag ggagctcgtc attccctgcc gggttacgtc acctaacatc    180
actgttactt taaaaaagtt tccacttgac actttgatcc ctgatggaaa acgcataatc    240
tgggacagta gaaagggctt catcatatca aatgcaacgt acaaagaaat agggcttctg    300
acctgtgaag caacagtcaa tgggcatttg tataagacaa actatctcac acatcgacaa    360
accaatacaa tcatagctgt ggttctgagt ccgtctcatg gaattgaact atctgttgga    420
gaaaagcttg tcttaaattg tacagcaaga actgaactaa atgtggggat tgacttcaac    480
tgggaatacc cttcttcgaa gcatcagcat aagaaacttg taaaccgaga cctaaaaacc    540
cagtctggga gtgagatgaa gaaatttttg agcaccttaa ctatagatgg tgtaacccgg    600
agtgaccaag gattgtacac ctgtgcagca tccagtgggc tgatgaccaa gaagaacagc    660
acatttgtca gggtccatga aaagggcccg gcgacaaaa ctcacacatg cccactgtgc    720
ccagcacctg aactcctggg gggaccgtca gtcttcctct tccccccaaa acccaaggac    780
accctcatga tctcccggac ccctgaggtc acatgcgtgg tggtggacgt gagccacgaa    840
gaccctgagg tcaagttcaa ctggtacgtg gacggcgtgg aggtgcataa tgccaagaca    900
aagccgcggg aggagcagta caacagcacg taccgtgtgg tcagcgtcct caccgtcctg    960
caccaggact ggctgaatgg caaggagtac aagtgcaagg tctccaacaa agccctccca   1020
gcccccatcg agaaaaccat ctccaaagcc aaagggcagc cccgagaacc acaggtgtac   1080
accctgcccc catcccggga tgagctgacc aagaaccagg tcagcctgac ctgcctagtc   1140
aaaggcttct atcccagcga catcgccgtg gagtgggaga gcaatgggca gccggagaac   1200
aactacaagg ccacgcctcc cgtgctggac tccgacggct ccttcttcct ctacagcaag   1260
ctcaccgtgg acaagagcag gtggcagcag gggaacgtct tctcatgctc cgtgatgcat   1320
gaggctctgc acaaccacta cacgcagaag agcctctccc tgtctccggg taaatga      1377
```

<210> SEQ ID NO 13
<211> LENGTH: 458
<212> TYPE: PRT
<213> ORGANISM: Artificial Sequence
<220> FEATURE:
<223> OTHER INFORMATION: VEGF-TRAP

<400> SEQUENCE: 13

```
Met Val Ser Tyr Trp Asp Thr Gly Val Leu Leu Cys Ala Leu Leu Ser
  1               5                  10                  15

Cys Leu Leu Leu Thr Gly Ser Ser Ser Gly Gly Arg Pro Phe Val Glu
             20                  25                  30

Met Tyr Ser Glu Ile Pro Glu Ile Ile His Met Thr Glu Gly Arg Glu
         35                  40                  45

Leu Val Ile Pro Cys Arg Val Thr Ser Pro Asn Ile Thr Val Thr Leu
     50                  55                  60

Lys Lys Phe Pro Leu Asp Thr Leu Ile Pro Asp Gly Lys Arg Ile Ile
 65                  70                  75                  80

Trp Asp Ser Arg Lys Gly Phe Ile Ile Ser Asn Ala Thr Tyr Lys Glu
                 85                  90                  95

Ile Gly Leu Leu Thr Cys Glu Ala Thr Val Asn Gly His Leu Tyr Lys
            100                 105                 110

Thr Asn Tyr Leu Thr His Arg Gln Thr Asn Thr Ile Ile Asp Val Val
        115                 120                 125

Leu Ser Pro Ser His Gly Ile Glu Leu Ser Val Gly Glu Lys Leu Val
```

```
                130             135             140
Leu Asn Cys Thr Ala Arg Thr Glu Leu Asn Val Gly Ile Asp Phe Asn
145                 150                 155                 160

Trp Glu Tyr Pro Ser Ser Lys His Gln His Lys Lys Leu Val Asn Arg
                165                 170                 175

Asp Leu Lys Thr Gln Ser Gly Ser Glu Met Lys Lys Phe Leu Ser Thr
            180                 185                 190

Leu Thr Ile Asp Gly Val Thr Arg Ser Asp Gln Gly Leu Tyr Thr Cys
        195                 200                 205

Ala Ala Ser Ser Gly Leu Met Thr Lys Lys Asn Ser Thr Phe Val Arg
210                 215                 220

Val His Glu Lys Gly Pro Gly Asp Lys Thr His Thr Cys Pro Leu Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Ala Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 14
<211> LENGTH: 330
<212> TYPE: DNA
<213> ORGANISM: Artificial Sequence
<220> FEATURE:
<223> OTHER INFORMATION: VEGFR domain 2

<400> SEQUENCE: 14
gactagcagt ccggaggtag acctttcgta gagatgtaca gtgaaatccc cgaaattata      60
cacatgactg aaggaaggga gctcgtcatt ccctgccggg ttacgtcacc taacatcact     120
gttactttaa aaagtttcc acttgacact tgatccctg atggaaaacg cataatctgg       180
gacagtagaa agggcttcat catatcaaat gcaacgtaca aagaaatagg gcttctgacc     240
```

```
tgtgaagcaa cagtcaatgg gcatttgtat aagacaaact atctcacaca tcgacaaacc    300
aatacaatca tagatgtggt tctgagtccg                                     330
```

<210> SEQ ID NO 15
<211> LENGTH: 36
<212> TYPE: DNA
<213> ORGANISM: Artificial Sequence
<220> FEATURE:
<223> OTHER INFORMATION: PCR forward primer VEGFR1 domain 2

<400> SEQUENCE: 15

```
gactagcagt ccggaggtag acctttcgta gagatg                               36
```

<210> SEQ ID NO 16
<211> LENGTH: 33
<212> TYPE: DNA
<213> ORGANISM: Artificial Sequence
<220> FEATURE:
<223> OTHER INFORMATION: PCR reverse primer VEGFR1 domain 2

<400> SEQUENCE: 16

```
cggactcaga accacatcta tgattgtatt ggt                                  33
```

<210> SEQ ID NO 17
<211> LENGTH: 333
<212> TYPE: DNA
<213> ORGANISM: Artificial Sequence
<220> FEATURE:
<223> OTHER INFORMATION: VEGFR2 domain 3

<400> SEQUENCE: 17

```
acaatcatag atgtggttct gagtccgtct catggaattg aactatctgt tgagaaaag     60 cttgtcttaa attgtacagc aagaactgaa ctaaatgtgg ggattgactt caactgggaa   120 taccttctt cgaagcatca gcataagaaa cttgtaaacc gagacctaaa aacccagtct    180
gggagtgaga tgaagaaatt tttgagcacc ttaactatag atggtgtaac ccggagtgac   240
caaggattgt acacctgtgc agcatccagt gggctgatga ccaagaagaa cagcacattt   300
gtcagggtcc atgaaaaggg cccgggcatt atc                                333
```

<210> SEQ ID NO 18
<211> LENGTH: 44
<212> TYPE: DNA
<213> ORGANISM: Artificial Sequence
<220> FEATURE:
<223> OTHER INFORMATION: PCR former primer for VEGFR2 domain 3

<400> SEQUENCE: 18

```
acaatcatag atgtggttct gagtccgtct catgcccact gtgc                      44
```

<210> SEQ ID NO 19
<211> LENGTH: 38
<212> TYPE: DNA
<213> ORGANISM: Artificial Sequence
<220> FEATURE:
<223> OTHER INFORMATION: PCR reverse primer for VEGFR2 domain 3

<400> SEQUENCE: 19

```
gataatgccc gggcccttttt catggaccct gacaaatg                            38
```

<210> SEQ ID NO 20
<211> LENGTH: 695
<212> TYPE: DNA

-continued

<213> ORGANISM: Artificial Sequence
<220> FEATURE:
<223> OTHER INFORMATION: IgG1 FC region

<400> SEQUENCE: 20
agggcccggg cgacaaaact cacacatgcc cactgtgccc agcacctgaa ctcctggggg    60
gaccgtcagt cttcctcttc cccccaaaac ccaaggacac cctcatgatc tcccggaccc   120
ctgaggtcac atgcgtggtg gtggacgtga gccacgaaga ccctgaggtc aagttcaact   180
ggtacgtgga cggcgtggag gtgcataatg ccaagacaaa gccgcgggag gagcagtaca   240
acagcacgta ccgtgtggtc agcgtcctca ccgtcctgca ccaggactgg ctgaatggca   300
aggagtacaa gtgcaaggtc tccaacaaag ccctcccagc ccccatcgag aaaaccatct   360
ccaaagccaa aggcagcccc gagaaccaca ggtgtacacc ctgcccccca tcccgggatg   420
agctgaccaa gaaccaggtc agcctgacct gcctagtcaa aggcttctat cccagcgaca   480
tcgccgtgga gtgggagagc aatgggcagc cggagaacaa ctacaaggcc acgcctcccg   540
tgctggactc cgacggctcc ttcttcctct acagcaagct caccgtggac aagagcaggt   600
ggcagcaggg gaacgtcttc tcatgctccg tgatgcatga ggctctgcac aaccactaca   660
cgcagaagag cctctccctg tctccgggta aatga                              695

<210> SEQ ID NO 21
<211> LENGTH: 38
<212> TYPE: DNA
<213> ORGANISM: Artificial Sequence
<220> FEATURE:
<223> OTHER INFORMATION: PCR forward primer for IgG1 FC region

<400> SEQUENCE: 21
agggcccggg cgacaaaact cacacatgcc cactgtgc                            38

<210> SEQ ID NO 22
<211> LENGTH: 22
<212> TYPE: DNA
<213> ORGANISM: Artificial Sequence
<220> FEATURE:
<223> OTHER INFORMATION: PCR reverse primer for IgG1 FC region

<400> SEQUENCE: 22
caatgctagc tcatttaccc gg                                             22

<210> SEQ ID NO 23
<211> LENGTH: 93
<212> TYPE: DNA
<213> ORGANISM: Artificial Sequence
<220> FEATURE:
<223> OTHER INFORMATION: VEGFR1 signal sequence synthetic
      oligonucleotide

<400> SEQUENCE: 23
tcgaagatct atggtcagct actgggacac cggggtcctg ctgtgcgcgc tgctcagctg    60
tctgcttctc acaggatcta gttccggagg tag                                 93

<210> SEQ ID NO 24
<211> LENGTH: 72
<212> TYPE: DNA
<213> ORGANISM: Homo sapien

<400> SEQUENCE: 24
gctccagtaa agcagactct aaacttcgat cttctcaagc tcgctggaga tgttgagagc    60

```
aacccaggtc ca                                                            72

<210> SEQ ID NO 25
<211> LENGTH: 593
<212> TYPE: DNA
<213> ORGANISM: Artificial Sequence
<220> FEATURE:
<223> OTHER INFORMATION: WPRE

<400> SEQUENCE: 25
aatcaacctc tggattacaa aatttgtgaa agattgactg gtattcttaa ctatgttgct        60
ccttttacgc tatgtggata cgctgcttta atgcctttgt atcatgctat tgcttcccgt      120
atggctttca ttttctcctc cttgtataaa tcctggttgc tgtctcttta tgaggagttg      180
tggcccgttg tcaggcaacg tggcgtggtg tgcactgtgt ttgctgacgc aaccccact       240 ggttggggca ttgccaccac ctgtcagctc ctttccggga cttttgcttt cccctccct       300 attgccacgg cggaactcat cgccgcctgc cttgcccgct gctggacagg ggctcggctg      360
ttgggcactg acaattccgt ggtgttgtcg gggaagctga cgtcctttcc atggctgctc      420
gcctgtgttg ccacctggat tctgcgcggg acgtccttct gctacgtccc ttcggccctc      480
aatccagcgg accttccttc ccgcggcctg ctgccggctc tgcggcctct tccgcgtctt      540
cgccttcgcc ctcagacgag tcggatctcc ctttgggccg cctccccgcc tgg             593

<210> SEQ ID NO 26
<211> LENGTH: 224
<212> TYPE: DNA
<213> ORGANISM: Artificial Sequence
<220> FEATURE:
<223> OTHER INFORMATION: Bovine GrowthHormone Polyadenylation Signal
      Sequence

<400> SEQUENCE: 26
gtgagatccg ctcgctgatc agcctcgact gtgccttcta gttgccagcc atctgttgtt       60
tgcccctccc ccgtgccttc cttgaccctg gaaggtgcca ctcccactgt cctttcctaa      120
taaaatgagg aaattgcatc gcattgtctg agtaggtgtc attctattct ggggggtggg      180
gtggggcagg acagcaaggg ggaggattgg gaagacaata gcag                       224

<210> SEQ ID NO 27
<211> LENGTH: 492
<212> TYPE: DNA
<213> ORGANISM: Artificial Sequence
<220> FEATURE:
<223> OTHER INFORMATION: EMCV IRES

<400> SEQUENCE: 27
gttattttcc accatattgc cgtcttttgg caatgtgagg gcccggaaac ctggccctgt       60
cttcttgacg agcattccta gggtctttcc cctctcgcc aaaggaatgc aaggtctgtt      120
gaatgtcgtg aaggaagcag ttcctctgga agcttcttga agacaaacaa cgtctgtagc      180
gaccctttgc aggcagcgga accccccacc tggcgacagg tgcctctgcg gccaaaagcc      240
acgtgtataa gatacacctg caaaggcggc acaaccccag tgccacgttg tgagttggat      300
agttgtggaa agagtcaaat ggctctcctc aagcgtattc aacaaggggc tgaaggatgc      360
ccagaaggta ccccattgta tgggatctga tctggggcct cggtgcacat gctttacatg      420
tgtttagtcg aggttaaaaa aacgtctagg ccccccgaac cacggggacg tggttttcct      480
ttgaaaaaca cg                                                          492
```

```
<210> SEQ ID NO 28
<211> LENGTH: 72
<212> TYPE: DNA
<213> ORGANISM: Homo sapien

<400> SEQUENCE: 28
gctccagtaa agcagactct aaacttcgat cttctcaagc tcgctggaga tgttgagagc      60
aacccaggtc ca                                                         72

<210> SEQ ID NO 29
<211> LENGTH: 15
<212> TYPE: DNA
<213> ORGANISM: Artificial Sequence
<220> FEATURE:
<223> OTHER INFORMATION: pTR-CAG-VEGFR3-WPRE-BGHpA reverse primer

<400> SEQUENCE: 29
cattcgctag caatt                                                      15

<210> SEQ ID NO 30
<211> LENGTH: 93
<212> TYPE: DNA
<213> ORGANISM: Artificial Sequence
<220> FEATURE:
<223> OTHER INFORMATION: VEGFR1 signal sequence complementary strand

<400> SEQUENCE: 30
ctacctccgg aactagatcc tgtgagaagc agacagctga gcagcgcgca cagcaggacc      60
ccggtgtccc agtagctgac ctaagatctt cga                                  93
```

METHOD FOR TREATING CANCER BY VECTOR-MEDIATED DELIVERY OF ONE OR MORE ANTI-ANGIOGENIC OR PRO-APOPTOTIC GENES

This application claims priority from U.S. Provisional Application Ser. No. 60/475,006 filed June 3, 2003. The entirety of that provisional application is incorporated herein by reference.

BACKGROUND OF THE INVENTION

1. Field of the Invention

The present invention relates to vector-mediated delivery and in vivo expression of polynucleotides encoding proteins that are effective in the treatment of cancer. In particular, the invention relates to the use of recombinant viral and non-viral vectors to deliver genes encoding one or more anti-angiogenic or pro-apoptotic gene products for the treatment of cancer.

2. Background of the Technology

In normal tissue homeostasis is achieved by the balance between the rate of cell proliferation and the rate of cell death. Disruption of this balance is thought to be a major event in the development of cancer. Growth of new blood vessels (angiogenesis) is also known to play a key role in cancer progression in addition to its role in tissue repair. Cellular invasion is an important aspect of cancer metastasis. Currently, standard medical therapies for treatment of cancer including chemotherapy, surgery, radiation therapy and cellular immuno-therapy, have clear limitations with regard to both efficacy and toxicity. To date, these approaches have met with varying degrees of success dependent upon the type of cancer, general health of the patient, stage of disease at the time of diagnosis, etc.

Previous approaches to gene therapy for cancer have focused primarily on the delivery of suicide genes using retroviral, adenoviral and herpes viral vectors. Gene therapy strategies are the subject of ongoing clinical trials, but have not yet demonstrated clinical efficacy. Limited success has been observed, with problems attributed to inefficient gene transfer. Previous anti-cancer strategies include delivery of genes directly to the tumor, direct bolus injection or sustained systemic delivery of anti-cancer agents. Despite advances, lack of significant clinical benefit and/or severe side effects due to the toxicity of currently used treatment regimens remains a problem.

Accordingly, there remains a need for cancer therapies that improve clinical benefit while reducing toxic side effects. Innovative strategies, such as vector-mediated delivery of anti-angiogenic or proapoptotic genes alone or in combination with standard medical treatments, may therefore provide a means for enhanced effectiveness and decreased toxicity in the treatment of cancer.

The present invention addresses this by providing vectors and methods that allow for effective gene delivery and expression of one or more therapeutic genes in patients with cancer. Preferably, such methods exhibit efficient transduction of target cells, good therapeutic yield of the therapeutic factor(s), low toxicity and result in an overall improved clinical benefit for the patient under treatment.

SUMMARY OF THE INVENTION

The invention provides vectors and methods for vector-mediated delivery and expression of anti-cancer factors that are effective in the treatment of cancer. In particular, the invention relates to the use of recombinant viral and non-viral vectors to deliver genes encoding one or more anti-angiogenic or pro-apoptotic gene products to a subject for the treatment of cancer.

In one aspect, the vector is an AAV vector comprising the coding sequence for one or more anti-cancer factors selected from the group consisting of VEGF-TRAP (SEQ ID NO: 12), soluble tumor necrosis factor alpha-related apoptosis-inducing ligand (SEQ ID NO: 1) and an isoluecine zipper modified variant version of soluble human TRAIL (LZsTRAIL; SEQ ID NO: 3), soluble platelet factor 4 (sPF4) (SEQ ID NO: 6), and soluble platelet factor 4 with a DLR mutation (sPF4; SEQ ID NO: 8).

In another aspect, the cancer is selected from the group consisting of glioma, bladder cancer, breast cancer, colon cancer, melanoma cancer, liver cancer, lung cancer, ovarian cancer, prostate cancer, renal cell carcinoma, hemangioma and astrocytoma.

In yet another aspect, the promoter is a CAG promoter, an hEF1a-eIF4g promoter, an hEF1 alpha promoter or a mTTR promoter and the vector may further comprise a woodchuck post-transcriptional regulatory element (WPRE) and/or a bovine growth hormone polyadenylation sequence (BGHpA).

Preferred AAV Serotypes Include AAV-6, AAV-7 and AAV-8.

In one embodiment, the method further comprises administering to the subject a standard therapeutic modality typically used to treat the subject cancer, such as administering a chemotherapeutic agent selected from the group consisting of etoposide, vincristine, cisplatin, doxorubicin, camptothecin and (BCNU) carmustine or a COX-2 inhibitor or administering radiation therapy to the subject.

These and other objects and features of the invention will be more fully appreciated when the following detailed description of the invention is read in conjunction with the accompanying drawings.

DESCRIPTION OF THE FIGURES

FIGS. 7A and B are a schematic depiction of the construction of AAV-sTRAIL (FIG. 7B), which has an extracellular domain including amino acids 114–281 of human TRAIL fused to an isoleucine zipper motif and a tPA signal sequence.

FIG. 8A shows the results of PAGE using a 12% non-reducing PAGE gel and FIG. 8B shows the results of PAGE using a 12% reducing gel. Soluble isoleucine zipper modified human TRAIL cDNA (sTRAIL) or full-length human TRAIL (wildtype TRAIL) was cloned into a pORF or pAAV expression plasmid. Conditioned media was harvested from 293 cells that were mock transfected (lane 1), or transiently transfected with pORF-sTRAIL (lane 2), pAAV-sTRAIL (lane 3) or pORF-w.t.-TRAIL (lane 4). Conditioned media was collected 48 hr following transfection, immunoblotted and detected via an anti-human TRAIL antibody. Arrows indicate the monomeric and dimeric forms of soluble TRAIL.

FIGS. 10A–C illustrate the cytotoxicity of sTRAIL on Colo-205 Cancer Cells in a dose-dependent manner. Incubation of cells with sTRAIL/rhTRAIL conditioned medium led to cell death in contrast to the lack of cytotoxicity observed with media from AAV-GFP transduced 293 cells. The results show that sTRAIL/rhTRAIL potently inhibits Colo-205 cell proliferation/viability with sub-nM affinity. FIG. 10A shows viability of human Colo-205 colorectal tumor cells after 24 hr treatment with the indicated amounts of conditioned media from AAV-sTRAIL or AAV-GFP transduced 293 cells. FIG. 10B illustrates growth inhibition of Colo-205 cells upon treatment with the indicated amounts of recombinant human TRAIL after 24, 48 and 72 hr. FIG. 10C illustrates growth inhibition of Colo-205 cells upon incubation with the indicated amounts of AAV-produced sTRAIL after 24, 48 and 72 hr. Cell proliferation was evaluated using a WST-8-based tetrazolium salt viability assay using the formulas: % Viability=[OD (sTRAIL) treated−background]/[OD (GFP) untreated−background]×100 and % Growth Inhibition=[1-(OD treated−background)/OD untreated−background)]×100. The 50% inhibitory concentration for recombinant human TRAIL and AAV-produced sTRAIL is shown for FIGS. 10B and 10C.

FIG. 11A shows an increase in cytoplasmic histone-associated nucleosomes (DNA fragmentation) in human Colo-205 cells upon 6 hr incubation with recombinant human TRAIL in a dose-dependent manner, with no increase in apoptosis observed for untreated cells. FIG. 11B shows a dose-dependent increase in cytoplasmic histone-associated nucleosomes (DNA fragmentation) in human Colo-205 cells following 6 hr incubation with conditioned media from AAV-sTRAIL transduced cells, but not with conditioned media from AAV-GFP control cells. FIG. 11C illustrates the dose-dependent cellular apoptosis of Colo-205 cells following 6 hr incubation with recombinant human TRAIL. The 50% effective dose (ED50) for induction of cellular apoptosis of Colo205 cells by recombinant human TRAIL is approximately 1 ng/ml. FIG. 11D illustrates a dose-response curve for apoptosis in Colo-205 cells following incubation with AAV-generatedsTRAIL after 6, 16 and 24 hr. In this experiment, the observed 50% effective dose (ED50) for induction of Colo205 cell apoptosis by AAV-generated sTRAIL was approximately 10 ng/ml.

FIG. 12A shows dose-dependent induction in both intracellular Caspase-3 or Caspase-8 enzymatic activity in human Colo-205 tumor cells following 4 hr incubation with increasing amounts of AAV-produced sTRAIL.

FIG. 13A illustrates that the induction of DNA fragmentation in Colo-205 cells by AAV-produced sTRAIL, can be specifically inhibited by pre-incubating the cells with increasing amounts of the pan-caspase inhibitor, ZVAD-fmk.

FIGS. 16A–D show augmentation of sTRAIL-induced tumor cell cytotoxicity by chemotherapy sensitization 1 e4 tumor cells were pretreated with genotoxic agents for 24 hr to sensitize, then subsequently treated with sTRAIL for 24 hr. Viability was measured by WST-8 tetrazolium salt assay after 24 hr sTRAIL treatment and % Growth inhibition=[1-(OD treated–background)/(OD untreated–background)× 100]. FIG. 16A shows the results of an experiment utilizing A549 Lung cells+Cisplatin; FIG. 16B shows the results of an experiment utilizing U87MG Glioma+Etoposide; FIG. 16C shows the results of an experiment utilizing MCF-7 Breast+Doxorubicin; and FIG. 16D shows the results of an experiment utilizing PC-3 Prostate+Doxorubicin.

FIG. 17A shows the results of an experiment utilizing HT29 colon cancer cells+doxorubicin; FIG. 17B shows the results of an experiment utilizing HT29 colon cancer cells+cisplatin; and FIG. 17C shows the results of an experiment utilizing HT29 colon cancer cells+camptothecin.

FIGS. 18A–C show augmentation of colon cell cytotoxicity using combination treatment with sTRAIL+COX inhibitors, wherein FIG. 18A shows the results of an experiment utilizing HT29 colon cancer cells; FIG. 18B shows the results of an experiment utilizing HCT-116 cells and FIG. 18C shows the results of an experiment utilizing Colo-205 cells.

FIGS. 19A–D illustrates the cytotoxicity of various human glioma cell lines following AAV-TRAIL infection in vitro, wherein FIG. 19A: illustrates the cytotoxic effect of AAV-TRAIL on T98G cells; FIG. 19B: illustrates the effect on LN18 glioma cells; FIG. 19C: illustrates the effect on U87MG glioma cells and FIG. 19D illustrates the effect on U138MG glioma cells. Human glioma cells were infected with recombinant AAV vectors encoding membrane-bound human TRAIL (mbTRAIL) or soluble TRAIL (sTRAIL) at increasing multiplicities of infections. After 72 hr of infection, cytotoxicity/viability of glioma cells was evaluated using a WST-8-based tetrazolium salt cytotoxicity assay

FIGS. 22A and B illustrate augmented cytotoxicity by TRAIL in presence of chemotherapy. Human U87MG (FIG. 22A) or T98G (FIG. 22B) glioma tumor cells were pre-treated in vitro with subtoxic doses of BCNU (Carmustine), etoposide or vincristine for 24 hr and then incubated with the indicated sub-toxic doses of soluble TRAIL Cytotoxicity/viability of glioma cells was evaluated 48 hr after treatment using a WST-8-based tetrazolium salt cytotoxicity assay

FIG. 33A); sPF4: EMCV IRES: VEGF TRAP (pTR-CAG-sPF4-I-VT; FIG. 33B); VEGF TRAP:F2A:sPF4 (pTR-CAG-VT-F2A-sPF4; FIG. 33C); VEGF TRAP:EMCV IRES:sPF4 (pTR-CAG-VT-I-sPF4; FIG. 33D).

FIGS. 34A–C show expression levels of VEGF-TRAP and sPF4 from plasmids expressing both proteins from a single promoter using F2A and IRES sequences, where FIG. 34A illustrates the level of PF4 produced as analyzed by ELISA (ng/ml); FIG. 34B illustrates the level of VEGF TRAP produced as analyzed by ELISA (ng/ml); and FIG. 34C illustrates the expression level of the GFP transfection control indicated as percent positive.

DETAILED DESCRIPTION OF THE INVENTION

I. Definitions

Figure 1:
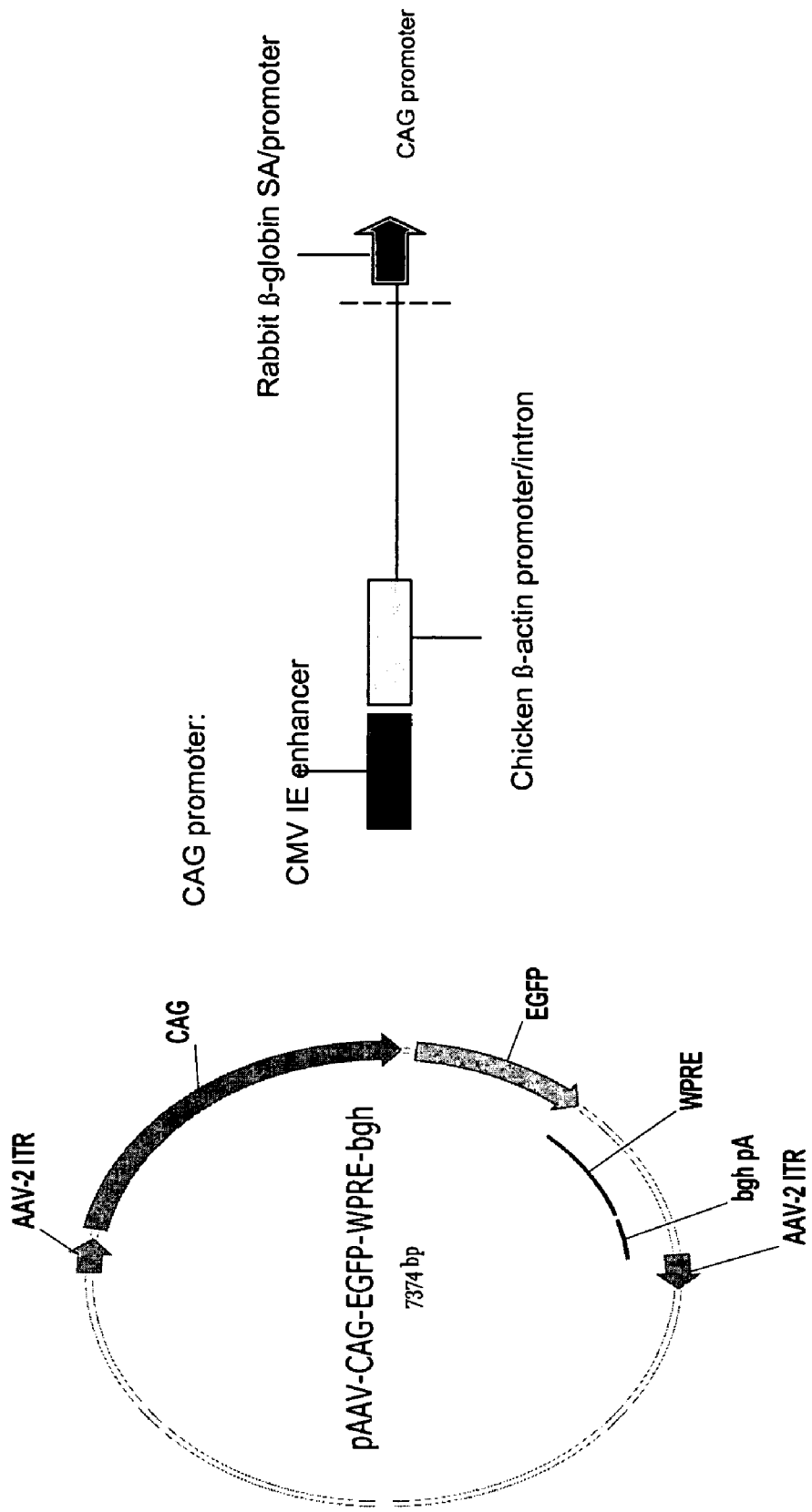
FIG. 1 is a schematic depiction of an AAV expression vector which includes the CAG promoter driving enhanced green fluorescent protein (EGFP) followed by a post-transcriptional regulatory element (WPRE) and polyA sequence (bgh pA).

Unless otherwise indicated, all technical and scientific terms used herein have the same meaning as they would to one skilled in the art of the present invention. Practitioners are particularly directed to Sambrook et al., Molecular Cloning: A Laboratory Manual (Second Edition), Cold Spring Harbor Press, Plainview, N.Y., 1989 and Ausubel F M et al., Current Protocols in Molecular Biology, John Wiley & Sons, New York, N.Y. 1993, for definitions and terms of the art. It is to be understood that this invention is not limited to the particular methodology, protocols, and reagents described, as these may vary.

The publications and other materials including all patents, patent applications, publications (including published patent applications), and database accession numbers referred to in this specification are used herein to illuminate the background of the invention and in particular, cases to provide additional details respecting the practice. The publications and other materials including all patents, patent applications, publications (including published patent applications), and database accession numbers referred to in this specification are incorporated herein by reference to the same extent as if each were specifically and individually indicated to be incorporated by reference in its entirety.

The term "vector", as used herein, refers to a nucleic acid construct designed for transfer between different host cells. An "expression vector" or "gene therapy vector" refers to a vector that has the ability to incorporate and express heterologous DNA fragments in a foreign cell. A cloning or expression vector may comprise additional elements, for example, the expression vector may have two replication systems, thus allowing it to be maintained in two organisms, for example in human cells for expression and in a prokaryotic host for cloning and amplification. The term vector may also be used to describe a recombinant virus, e.g., a virus modified to contain the coding sequence for a therapeutic compound or factor. As used herein, a vector may be of viral or non-viral origin.

The terms "virus," "viral particle," "vector particle," "viral vector particle," and "virion" are used interchangeably and are to be understood broadly as meaning infectious viral particles that are formed when, e.g., a viral vector of the invention is transduced into an appropriate cell or cell line.

Viral particles according to the invention may be utilized for the purpose of transferring DNA into cells either in vitro or in vivo. The terms "vector," "polynucleotide vector," "polynucleotide vector construct," "nucleic acid vector construct," and "vector construct" are used interchangeably herein to mean any nucleic acid construct for gene transfer, as understood by one skilled in the art.

As used herein, the term "viral vector" is used according to its art-recognized meaning. It refers to a nucleic acid vector construct that includes at least one element of viral origin and may be packaged into a viral vector particle. The vector and/or particle may be utilized for the purpose of transferring DNA, RNA or other nucleic acids into cells either in vitro or in vivo. Numerous forms of viral vectors are known in the art.

The term "nucleic acid" refers to deoxyribonucleotides or ribonucleotides and polymers thereof ("polynucleotides") in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid molecule/polynucleotide also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19: 5081 (1991); Ohtsuka et al., J. Biol. Chem. 260: 2605–2608 (1985); Rossolini et al., Mol. Cell. Probes 8: 91–98 (1994)). Nucleotides are indicated by their bases by the following standard abbreviations: adenine (A), cytosine (C), thymine (T), and guanine (G).

The term "replication defective" as used herein relative to a viral gene therapy vector of the invention means the viral vector cannot further replicate and package its genomes. For example, when the cells of a subject are infected with rAAV virions, the heterologous gene is expressed in the patient's cells, however, due to the fact that the patient's cells lack AAV rep and cap genes and the adenovirus accessory function genes necessary to replicate and package rAAV, the rAAV is replication defective and wild-type AAV cannot be formed in the patient's cells.

As used herein, "packaging system" refers to a set of viral constructs comprising genes that encode viral proteins involved in packaging a recombinant virus. Typically, the constructs of the packaging system will ultimately be incorporated into a packaging cell.

The term "operably linked" as used herein relative to a recombinant DNA construct or vector means nucleotide components of the recombinant DNA construct or vector that are directly linked to one another for operative control of a selected coding sequence. Generally, "operably linked" DNA sequences are contiguous, and, in the case of a secretory leader, contiguous and in reading frame. However, enhancers do not have to be contiguous.

As used herein, the term "gene" or "coding sequence" means the nucleic acid sequence which is transcribed (DNA) and translated (mRNA) into a polypeptide in vitro or in vivo when operably linked to appropriate regulatory sequences. The gene may or may not include regions preceding and following the coding region, e.g. 5' untranslated (5' UTR) or "leader" sequences and 3' UTR or "trailer" sequences, as well as intervening sequences (introns) between individual coding segments (exons).

As used herein, "transgene" refers to a polynucleotide that can be expressed, via recombinant techniques, in a non-native environment or heterologous cell under appropriate conditions. The transgene may be derived from the same type of cell in which it is to be expressed, but introduced from an exogenous source, modified as compared to a corresponding native form and/or expressed from a non-native site, or it may be derived from a heterologous cell. "Transgene" is synonymous with "exogenous gene", "foreign gene" and "heterologous gene".

As used herein, a "therapeutic" gene refers to a gene that, when expressed, confers a beneficial effect on the cell or tissue in which it is present, or on a mammal in which the gene is expressed. Examples of beneficial effects include amelioration of a sign or symptom of a condition or disease, prevention or inhibition of a condition or disease, or conferral of a desired characteristic. Therapeutic genes include genes that correct a genetic deficiency in a cell or mammal.

The terms "heterologous" and "exogenous" as used herein with reference to nucleic acid molecules such as promoters and coding sequences, refer to sequences that originate from a source foreign to a particular vector, virus or host cell, or if from the same source, are modified from their original form. Thus, a heterologous gene in a virus or cell includes a gene that is endogenous to the particular virus or cell but has been modified through, for example, codon optimization. The terms also include non-naturally occurring multiple copies of a naturally occurring nucleic acid sequence. Thus, the terms refer to a nucleic acid segment that is foreign or heterologous to the vector, virus or cell, or homologous to the vector, virus or cell but in a position within the vector or cellular genome in which it is not ordinarily found.

The terms "complement" and "complementary" refer to two nucleotide sequences that comprise antiparallel nucleotide sequences capable of pairing with one another upon formation of hydrogen bonds between the complementary base residues in the antiparallel nucleotide sequences.

The term "native" refers to a gene or protein that is present in the genome of the wildtype virus or cell.

The term "naturally occurring" or "wildtype" is used to describe an object that can be found in nature as distinct from being artificially produced by man. For example, a protein or nucleotide sequence present in an organism (including a virus), which can be isolated from a source in nature and which has not been intentionally modified by man in the laboratory, is considered to be "naturally occurring", "wildtype" or "native".

The term "recombinant" as used herein with reference to nucleic acid molecules refers to a combination of nucleic acid molecules that are joined together using recombinant DNA technology into a progeny nucleic acid molecule. As used herein with reference to viruses, cells, and organisms, the terms "recombinant," "transformed," and "transgenic" refer to a host virus, cell, or organism into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Recombinant viruses, cells, and organisms are understood to encompass not only the end product of a transformation process, but also recombinant progeny thereof. A "non-transformed," "non-transgenic," or "non-recombinant" host refers to a wildtype virus, cell, or organism that does not contain the heterologous nucleic acid molecule.

The terms "transcriptional regulatory protein", "transcriptional regulatory factor" and "transcription factor" are used interchangeably herein, and refer to a cytoplasmic or nuclear protein that binds a DNA response element and thereby transcriptionally regulates the expression of an associated gene or genes. Transcriptional regulatory proteins generally bind directly to a DNA response element, however in some cases binding to DNA may be indirect by way of binding to another protein that in turn binds to, or is bound to the DNA response element.

The term "promoter" refers to an untranslated DNA sequence usually located upstream of the coding region that contains the binding site for RNA polymerase II and initiates transcription of the DNA. The promoter region may also include other elements that act as regulators of gene expression. The term "minimal promoter" refers to a promoter element, particularly a TATA element that is inactive or has greatly reduced promoter activity in the absence of upstream activation elements.

The term "enhancer" within the meaning of the invention may be any genetic element, e.g., a nucleotide sequence that increases transcription of a coding sequence operatively linked to a promoter to an extent greater than the transcription activation effected by the promoter itself when operatively linked to the coding sequence, i.e. it increases transcription from the promoter.

A "termination signal sequence" within the meaning of the invention may be any genetic element that causes RNA polymerase to terminate transcription, such as for example a polyadenylation signal sequence. A polyadenylation signal sequence is a recognition region necessary for endonuclease cleavage of an RNA transcript that is followed by the polyadenylation consensus sequence AATAAA. A polyadenylation signal sequence provides a "polyA site", i.e. a site on a RNA transcript to which adenine residues will be added by post-transcriptional polyadenylation.

The term "homologous" as used herein with reference to a nucleic acid molecule refers to a nucleic acid sequence naturally associated with a host virus or cell.

The terms "identical" and percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the sequence comparison algorithms available to those of skill in the art such as those described herein, e.g. the Smith-Waterman algorithm, or by visual inspection.

In the context of the present invention, the term "isolated" refers to a nucleic acid molecule, polypeptide, virus, or cell that, by the hand of man, exists apart from its native environment and is therefore not a product of nature. An isolated nucleic acid molecule or polypeptide may exist in a purified form or may exist in a non-native environment such as, for example, a recombinant host cell. An isolated virus or cell may exist in a purified form, such as in a cell culture, or may exist in a non-native environment such as, for example, a recombinant or xenogeneic organism.

As used herein, a "retroviral transfer vector" refers to an expression vector that comprises a nucleotide sequence that encodes a transgene and that further comprises nucleotide sequences necessary for packaging of the vector. Preferably, the retroviral transfer vector also comprises the necessary sequences for expressing the transgene in cells.

As used herein, a "second generation" lentiviral vector system refers to a lentiviral packaging system that lacks functional accessory genes, such as one from which the accessory genes, vif, vpr, vpu and nef, have been deleted or inactivated. See, e.g., Zufferey et al., 1997, Nat. Biotechnol. 15:871–875.

As used herein, a "third generation" lentiviral vector system refers to a lentiviral packaging system that has the characteristics of a second generation vector system, and that further lacks a functional tat gene, such as one from which the tat gene has been deleted or inactivated. Typically, the gene encoding rev is provided on a separate expression construct. See, e.g., Dull et al., 1998, J. Virol. 72(11): 8463–8471.

As used herein, "pseudotyped" refers to the replacement of a native envelope protein with a heterologous or functionally modified envelope protein. The term "exposing", as used herein means bringing a therapeutic compound-encoding vector in contact with a target cell. Such "exposing", may take place in vitro, ex vivo or in vivo.

As used herein, the terms "stably transformed", "stably transfected" and "transgenic" refer to cells that have a non-native (heterologous) nucleic acid sequence integrated into the genome. Stable transformation is demonstrated by the establishment of cell lines or clones comprised of a population of daughter cells containing the transfecting DNA. In some cases, "transformation" is not stable, i.e., it is transient. In the case of transient transformation, the exogenous or heterologous DNA is expressed, however, the introduced sequence is not integrated into the genome.

The term "expression" refers to the transcription and/or translation of an endogenous gene, transgene or coding region in a cell. In the case of an antisense construct, expression may refer to the transcription of the antisense DNA only.

As used herein, the terms "biological activity" and "biologically active", refer to the activity attributed to a particular protein in a cell line in culture or in vivo. It will be appreciated that the "biological activity" of such a protein may vary somewhat dependent upon in vitro or in vivo conditions and is generally reported as a range of activity. Accordingly, a "biologically inactive" form of a protein refers to a form of the protein that has been modified in a manner that interferes with the activity of the protein as it is found in nature.

The term "angiogenesis", as used herein refers to the sprouting of blood vessels from pre-existing blood vessels, characterized by endothelial cell proliferation and the proliferation and migration of tube forming cells. Angiogenesis can be triggered by certain pathological conditions, such as the growth of solid tumors and metastasis.

The terms "anti-angiogenic compound", "anti-angiogenic factor", "anti-angiogenic polypeptide" and "anti-angiogenic protein", as used herein refer to a compound or factor that inhibits angiogenesis. i.e., the sprouting of blood vessels from pre-existing blood vessels, characterized by endothelial cell proliferation and the proliferation and migration of tube forming cells.

The terms "apoptotic cell death" and "apoptosis", as used herein refer to any cell death that results from, or is related to, the complex cascade of cellular events that occur at specific stages of cellular differentiation and in response to specific stimuli. Apoptotic cell death is characterized by condensation of the cytoplasm and chromatin condensation in the nucleus of dying cells. The process is associated with fragmentation of DNA into multiples of 200 base pairs and degradation of RNA as well as proteolysis in an organized manner without sudden lysis of the cell as in necrotic cell death.

The terms "anti-apoptotic compound", "anti-apoptotic factor", "anti-apoptotic polypeptide" and "anti-apoptotic protein", as used herein refer to a compound or factor that inhibits apoptosis. i.e., cell death that results from, or is related to, the complex cascade of cellular events that occur at specific stages of cellular differentiation and in response to specific stimuli., characterized by fragmentation of DNA into multiples of 200 base pairs and degradation of RNA as well as proteolysis in an organized manner without sudden lysis of the cell as in necrotic cell death.

The term "biologically active form", as used herein relative to a therapeutic compound or factor, i.e. an anti-angiogenic factor or anti-apoptotic factor, means any form of the compound or factor that exhibits anti-cancer activity. Anti-cancer activity may be evaluated using any of a number of assays routinely employed by those of skill in the art, both in the laboratory and in the clinical setting.

The terms "anti-cancer compound", "anti-cancer factor", "therapeutic compound" and "therapeutic factor" may be used interchangeably herein with reference to anti-angiogenic gene products, pro-apoptotic gene products, cytotoxic gene products and anti-invasive gene products, or combinations thereof.

As used herein, the terms "cancer", "cancer cells", "neoplastic cells", "neoplasia", "tumor", and "tumor cells" (used interchangeably) refer to cells that exhibit relatively autonomous growth, so that they exhibit an aberrant growth phenotype or aberrant cell status characterized by a significant loss of control of cell proliferation. Neoplastic cells can be malignant or benign.

The term "administering", as used herein refers to delivering a gene therapy vector encoding a therapeutic compound or factor to the cells of a subject. Such administering may take place in vivo, in vitro or ex vivo.

As used herein, "effective amount" relative to a vector encoding a therapeutic compound or factor refers to the vector administered to a mammalian subject, either as a single dose or as part of a series of doses and which is effective to result in an improved therapeutic outcome of the subject under treatment.

As used herein "treatment" of an individual or a cell is any type of intervention used in an attempt to alter the natural course of the individual or cell. Treatment includes, but is not limited to, administration of e.g., a vector encoding a therapeutic compound or factor, a pharmaceutical composition, alone or in combination with other treatment modalities generally known in the art. The "treatment" may be performed prophylactically, or subsequent to the initiation of a pathologic event.

As used herein, the term "improved therapeutic outcome" relative to a cancer patient refers to a slowing or diminution of the growth of cancer cells or a solid tumor, a reduction in the total number of cancer cells or total tumor burden, or a decrease in or amelioration of adverse symptoms.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. In addition, compositions for specific administration to the CNS are included such as artificial cerebrospinal fluid (see Cunningham et al 2000, Cell Transplantation, Vol. 9, 585–594). Compositions comprising such carriers are formulated by well known conventional methods (see, for example, Remington's Pharmaceutical Sciences, 18th edition, A. Gennaro, ed., Mack Publishing Co., Easton, Pa., 1990).

As used herein, "subject" refers to the recipient of the therapy to be practiced according to the invention. The subject can be any animal, including a vertebrate, but will preferably be a mammal. If a mammal, the subject will preferably be a human, but may also be a domestic livestock, laboratory subject or pet animal.

II. Methods and Compositions for Treatment of Cancer

The current invention provides an alternative approach to treatment of cancer that may be used alone or in combination with traditional treatment modalities. Exemplary cancers that may be tested using the methods and compositions described herein include but are not limited to brain cancer (e.g. glioma), bladder cancer, breast cancer, colon cancer, melanoma, liver cancer, lung cancer (i.e. non-small cell lung carcinoma or bronchoalveolar carcinoma (BAC), ovarian cancer, prostate cancer, myeloma, leukemia, renal cell carcinoma, pancreatic cancer, as further detailed below.

The invention addresses deficiencies in current treatment regimens by providing vector-mediated delivery of genes wherein the expression product of those genes has an anti-cancer effect, in particular an anti-angiogenic or pro-apoptotic effect. The methods and vectors described herein provide the advantage of sustained delivery of the therapeutic protein wherein delivery may be local to the site of a tumor (transduction of tumor tissue), in the general vicinity of the tumor (transduction of healthy tissue surrounding the tumor), or may be systemic (transduction of cells distant from tumor). Such sustained delivery makes possible local administration of vectors expressing therapeutic compounds that might otherwise exhibit systemic toxic side effects or require impractical delivery regimens due to poor stability or short half life of the gene product. Such sustained delivery also allows expression of therapeutic agents such as proteins or antibodies that are difficult/impossible to produce ex vivo and/or purify in high enough quantities to be beneficial to many patients. Furthermore, such delivery leads to a more steady state in vivo level of the anti-cancer agent as compared to bolus injections of recombinant proteins or antibodies which result in fluctuating serum levels of the therapeutic agent.

Use of the methods and compositions of the invention are exemplified in detail herein for treatment of glioma using plasmids or rAAV vectors, however, one of skill in the art will appreciate that the same methods and compositions find general utility in the treatment of cancer using any gene therapy vector system.

In one aspect, the invention provides recombinant adeno-associated virus (rAAV) vectors for expression of one or more anti-cancer compounds, wherein the vectors comprise a promoter capable of expressing a biologically active form of the anti-cancer compound operably linked to one or more structural genes encoding an anti-cancer compound. The compositions and methods of the invention provide vectors comprising the coding sequence for one or more anti-cancer compounds or factors, the expression products of which slow, inhibit or prevent the growth of cancer, e.g., glioma. Exemplary anti-cancer compounds include anti-angiogenic gene products, pro-apoptotic gene products, cytotoxic gene products and anti-invasive gene products, as further described below. In a related aspect, the invention provides one or more vectors comprising the coding sequence for a combination of anti-cancer compounds or factors, i.e. the coding sequence for one or more anti-angiogenic, pro-apoptotic, cytotoxic and/or anti-invasive gene products which are provided to target cells (i.e., glioma cells) and cells transduced with such vectors. The coding sequence for individual components of the combination of anti-cancer compounds may be provided to a cell in a single vector or by way of more than one vectors.

Adeno-associated virus (AAV) is a helper-dependent human parvovirus which because of its non-pathogenic nature, excellent clinical safety profile and ability to direct significant amounts of transgene expression in vivo AAV has significant potential as a human gene therapy vector. Adeno-associated viral (AAV) vectors have been suggested to be suitable for brain cancer gene therapy because the vectors are less immunogenic and less toxic than other viral vectors and lead to efficient transduction of brain. Initial studies using viral vectors, such as adenovirus and retrovirus, for brain cancer have been hampered by the lack of transduction within the CNS. Expression of the therapeutic transgene using these gene delivery systems is typically limited to cells immediately surrounding the injection site. In comparison, AAV vectors, being smaller in size (20 nm) and having different receptor affinities may have the ability to transduce wider areas.

The use of alternative AAV serotypes other than AAV-2 (Davidson et al (2000), PNAS 97(7)3428–32; Passini et al (2003), J. Virol 77(12):7034–40) has demonstrated different cell tropisms and increased transduction capabilities. With respect to brain cancers, the development of novel injection techniques into the brain, specifically convection enhanced delivery (CED; Bobo et al (1994), PNAS 91(6):2076–80; Nguyen et al (2001), Neuroreport 12(9):1961–4), has significantly enhanced the ability to transduce large areas of the brain with an AAV vector which would be required for successful therapy. In one aspect, the present invention is directed to vectors and methods that allow vector-mediated delivery and expression of one or more anti-cancer compounds in a patient with cancer, e.g. brain cancer allowing for efficient transduction of target cells.

Angiogenesis, the formation of blood vessels from pre-existing ones, plays a crucial role in tumor progression. The oxygen and nutrients supplied by the blood vessel to the tumor are crucial for cell function and survival. This limits all cells to reside within approximately 100 μM of a capillary blood vessel. Therefore in order to progress in size tumors must develop angiogenic capability. Given the universal nature of the requirement for angiogenesis in solid tumors, the agents described herein which block the formation of new blood vessels are applicable to a wide range of cancer targets. Those cancers which have a high degree of vascularization are particularly amenable to this type of viral mediated, anti-angiogenic therapy, notably grade IV astrocytomas/glioblastomas, breast cancer, colorectal cancer and renal cell carcinoma. In addition, other neoplasms which would be amenable to treatment with these agents include carcinomas of the lung (i.e. non-small cell lung carcinoma or broncheal aveolar carcinoma (BAC)), esophagus, gastric anatomy, rectum, liver, hepatoblastoma, ovary, cervix, endometrium, thecomas, arrhenoblastomas, endometrial hypoplasia, fibrosarcomas, head and neck carcinoma, nasopharyngeal, hemangioblastoma, Karposi's sarcoma, melanoma, skin carcinoma, pancreas carcinoma, retinoblastoma, Grade 1–3 astrocytoma, schwannoma, oligodendroglioma, medulloblastoma, neuroblastoma, rhabdomyosarcoma, meninginoma, oestoegenic sarcoma, leiomyosarcoma's, urinary tract carcinoma (e.g. bladder cancer), thyroid carcinomas, Wilm's tumor, prostate carcinoma, myeloma and leukemia. In addition other angiogenesis induced pathologies including disease caused by abnormal vascular proliferation, ascites formation, psoriasis, age-related macular degeneration, thyroid hyperplasia, preclampsia, pleural effusion, atherosclerosis, diabetic/other retinopathies and neovascular glaucoma could be treated using these therapies. These diseases listed above are given to exemplify the application of the described technology and in no means limit the scope of the invention.

A. Anti-angiogenic Gene Products

In one aspect, the invention is directed to gene therapy compositions and methods for use in inhibiting angiogenesis. Preferred therapeutic compounds and factors include platelet factor-4 (PF-4), Platelet factor-4 with a DLR mutation in the C-terminus (PF-4 DLR; Hagedom et al 2002, Cancer Research 62(23):6884–90), soluble VEGF receptor 2 chimera (SKDR-Fc); soluble VEGF receptor 1 chimera (SFlt-Fc); soluble VEGF receptor 1, 2 (hybrid) chimera (VEGF-TRAP; Holash J et al 2002, PNAS 99(17):11393–8); and murine anti-VEGF receptor 2 antibodies (aKDRmAb), e.g. DC101 (U.S. Pat. No. 5,955,311, expressly incorporated by reference herein).

With respect to constructs comprising the PF-4 gene, in one approach the naturally occurring signal peptide is included, however, the naturally occurring signal peptide may be replaced with the MCP-1, the IgK or human growth hormone signal peptides to increase secretion in vivo. In another approach, a DLR mutated version of PF-4 is used. See, e.g., Hagedom et al (2002, Cancer Research 62(23): 6884–90), which suggests that domain swapping in the of the COOH-terminal fragment of Platelet factor 4 (PF-4) from a DLQ amino acid motif to DLR or ELR may increase anti-cancer efficacy in vivo.

VEGF-TRAP

VEGF-TRAP consists of the signal sequence and domain 2 of VEGF receptor 1 attached to domain 3 of VEGF receptor 2 and a human IgG Fc region (Holash et al. Proc. Natl. Acad. Sci. USA. 99(17):11393–8, 2002) to generate a soluble VEGF inhibitor with a high binding affinity for VEGF and placental growth factor (P1GF) in vitro and a favorable pharmacokinetic profile in vivo. Preclinical tumor models have demonstrated that protein administration of VEGF-Trap is an effective anti-angiogenic agent reducing tumor burden and prolonging survival in a number of applications including glioma, neuroblastoma (Kim, E S et al. Proc. Nat. Acad. Sci. USA. 99(17):11399–11404, 2002), ovarian cancer (Byrne, A T et al. Clin. Can. Res. 9:5721–5728, 2003) and Wilms tumor (Huang, J et al. Proc. Nat. Acad. Sci. USA. 100(13):7785–7790, 2003) xenograft models. VEGF-TRAP blocks angiogenesis by interfering with the binding of VEGF and P1GF binding to their receptors. Vector-mediated delivery of VEGF-TRAP according to the present invention finds utility in the treatment of cancer alone or in combination with traditional therapeutic modalities such as chemotherapy and radiation therapy.

PF-4(DLR)

Platelet factor-4 (PF-4) is a member of the CXC family of chemokines and has been shown to be a potent in vitro inhibitor of endothelial cell proliferation and an in vivo inhibitor of angiogenesis (Maione, T E et al. Science 237: 77–79, 1990). Furthermore, recombinant PF-4 has been shown to inhibit the growth of B16F10 melanoma and HCT colon carcinoma cells (Sharpe, R L et al. J. Natl. Cancer Inst. 82:848–853, 1990, Kolber et al. J. Natl. Cancer Inst.

87:304–309, 1995). Adenoviral or retroviral delivery of a secreted form of PF-4 (sPF-4) was further shown to inhibit the growth of rat RT2 and human U87MG glioma cells through an angiogenesis-dependent mechanism (Tanaka et al., Nat. Med. 3:437–442, 1997). PF-4 appears to block angiogenesis by interfering with the binding of FGF-2 and VEGF binding to their receptors (Perollet, C. Blood 91:3289–3299, 1998, Gengrinovitch et al., J. Biol. Chem. 270:15059–15065, 1995). In addition, modified COOH-terminal PF-4 peptides containing the sequence DLR (replacing the endogenous DLQ motif), a critical domain present in proangiogenic chemokines, elicits several times greater antiangiogenic potential than the original parental PF-4 protein (Hagedom et al Can. Res. 62(23):6884–90, 2002). This modified PF-4(DLR) protein is capable of inhibiting the action of vascular endothelial growth factor and fibroblast growth factor 2 to endothelial cell receptors, endothelial cell proliferation, migration, and microvessel assembly in the rat aortic ring model and in the differentiated chick chorioallantoic membrane at lower doses than the original PF-4 protein. In an established intracranial glioma model in nude mice, local protein delivery of the modified PF-4 (DLR) protein had a significant increase in efficacy at reduced tumor growth when compared with the same dose of the original PF-4 peptide. Vector-mediated delivery of PF-4 protein and modified versions thereof, e.g., PF-4 (DLR), according to the present invention finds utility in the treatment of cancer alone or in combination with traditional therapeutic modalities such as chemotherapy and radiation therapy.

B. Pro-apoptotic and Cytotoxic Gene Products

In another aspect, the invention is directed to gene therapy compositions and methods comprising pro-apoptotic and/or cytotoxic genes or coding sequences. Preferred pro-apoptotic therapeutic compounds and factors include TRAIL (tumor necrosis factor alpha-related apoptosis-inducing ligand), in particular human TRAIL (hTRAIL) and soluble human TRAIL (TRAIL linked to a secretory tag and trimerization domain; see Wu et al 2001, Molecular Therapy 3(3):368–74), as well as factors involved in signaling pathways that lead to expression/production of these compounds.

Trail (Tumor Necrosis Factor Alpha-Related Apoptosis-Inducing Ligand)

TRAIL (also designated as Apo2L) is a type II transmembrane protein belonging to the tumor necrosis family (TNF) superfamily (1–4). TRAIL selectively induces apoptosis (programmed cell death) in a wide spectrum of cancer and transformed cells, but not in normal cells. TRAIL was originally identified using EST sequence homology searches to other known TNF family members. TRAIL consists of 281 amino acids and has the greatest amino acid identity (28%) to Fas Ligand in its extracellular domain. TRAIL is primarily expressed as a transmembrane protein of 33 kDa, however soluble forms of TRAIL exist by proteolytic cleavage. Like most members of the TNF superfamily, the extracellular domain of TRAIL forms a bell-shaped homotrimer which is stabilized by an internally bound zinc ion. TRAIL induces apoptosis through engagement of two death receptors (DR), DR4 and DR5. Binding of TRAIL to its DR causes receptor trimerization resulting in the recruitment of the death domain-containing adaptor proteins such as FADD/TRADD/RIP. The adaptor molecule complexes link the engagement of the DR to intracellular caspase signaling cascades including caspase-8. In addition, activation of caspase-8 induces cytochrome C release from the mitochondria resulting in the activation of caspase-3.

Caspase activation by TRAIL results in the activation of downstream substrate molecules which culminate into the morphological characteristics of apoptosis including chromatin condensation, cellular shrinkage and fragmentation and internucleosomal DNA fragmentation. A number of observations have been reported regarding the biological activity of TRAIL. See, e.g., Walczak, H. et al., (1999) Nat. Med. 5:157–163; Ashkenazi, A. (2002) Nat. Rev. Cancer 2:420–430; LeBlanc, H. N., and Ashkenazi, A. (2003) Cell Death Different. 10:66–75; and Srivastava, R. K. (2001) Neoplasia 3:535–546. Vector-mediated delivery of TRAIL and modified versions thereof, e.g., LZs TRAIL, according to the present invention finds utility in the treatment of cancer alone or in combination with traditional therapeutic modalities such as chemotherapy and radiation therapy.

Cytotoxic Therapeutic Compounds

Preferred cytotoxic therapeutic compounds and factors include HSV-thymidine kinase (HSV-TK); *E. coli* cytosine deaminase, yeast cytosine deaminase (*E. coli* CD or yeast CD) and yeast CD linked to UPRT (uracil phosphoribosyl transferase). Vector-mediated delivery of cytotoxic therapeutic compounds according to the present invention finds utility in the treatment of cancer alone or in combination with traditional therapeutic modalities such as chemotherapy and radiation therapy.

C. Anti-Invasive Gene Products

In yet another aspect, the invention is directed to gene therapy compositions and methods encoding anti-invasive gene products. Preferred therapeutic compounds and factors include tissue inhibitor of metalloproteinases 1 (TIMP-1); tissue inhibitor of metalloproteinases 2 (TIMP-2); and tissue inhibitor of metalloproteinases 3 (TIMP-3). Vector-mediated delivery of anti-invasive gene products according to the present invention finds utility in the treatment of cancer alone or in combination with traditional therapeutic modalities such as chemotherapy and radiation therapy.

D. Sequence Variants Encoding Anti-Angiogenic Gene Products,

Pro-Apoptotic/Cytotoxic Gene Products And Anti-Invasive Gene Products

Sequence variants of genes encoding native anti-cancer compounds and proteins described herein are included within the scope of the invention.

As used herein, the term "sequence identity" means nucleic acid or amino acid sequence identity in two or more aligned sequences, aligned using a sequence alignment program. The term "% homology" is used interchangeably herein with the term "% identity" herein and refers to the level of nucleic acid or amino acid sequence identity between two or more aligned sequences, when aligned using a sequence alignment program. For example, as used herein, 80% homology means the same thing as 80% sequence identity determined by a defined algorithm, and accordingly a homologue of a given sequence has greater than 80% sequence identity over a length of the given sequence.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), by the BLAST algorithm, Altschul et al., J. Mol. Biol. 215: 403–410 (1990), with software that is publicly available through the National Center for Biotechnology Information (http://www.ncbi.nlm.nih.gov/), or by visual inspection (see generally, Ausubel et al., infra). For purposes of the present invention, optimal alignment of sequences for comparison is most preferably conducted by the local homology algorithm of Smith & Waterman, Adv. Appl. Math. 2: 482 (1981).

In accordance with the present invention, also encompassed are sequence variants of genes encoding native anti-cancer compounds that have 80, 85, 88, 89, 90, 91, 92, 93, 94, 95, 96, 97, 98 or 99% or more sequence identity to the native nucleic acid or amino acid sequence of an anti-cancer compound described herein.

Sequence variants include nucleic acid molecules that encode the same polypeptide as is encoded by the therapeutic compounds or factors described herein. Thus, where the coding frame of the therapeutic gene is known, it will be appreciated that as a result of the degeneracy of the genetic code, a number of coding sequences can be produced. For example, the triplet CGT encodes the amino acid arginine. Arginine is alternatively encoded by CGA, CGC, CGG, AGA, and AGG. Therefore it is appreciated that such substitutions in the coding region fall within the sequence variants that are covered by the present invention.

A nucleic acid sequence is considered to be "selectively hybridizable" to a reference nucleic acid sequence if the two sequences specifically hybridize to one another under moderate to high stringency hybridization and wash conditions (i.e. "stringent hybridization conditions" and "stringent wash conditions). Hybridization conditions are based on the melting temperature ($T_m$) of the nucleic acid binding complex or probe. For example, "maximum stringency" typically occurs at about $T_m$–5° C. (5° below the $T_m$ of the probe); "high stringency" at about 5–10° below the $T_m$; "intermediate stringency" at about 10–20° below the $T_m$ of the probe; and "low stringency" at about 20–25° below the $T_m$. Functionally, maximum stringency conditions may be used to identify sequences having strict identity or near-strict identity with the hybridization probe; while high stringency conditions are used to identify sequences having about 80% or more sequence identity with the probe.

"Stringent hybridization conditions" and "stringent wash conditions" in the context of nucleic acid hybridization experiments such as Southern and Northern hybridizations are sequence dependent, and are different under different environmental parameters. Longer sequences hybridize at higher temperatures. An extensive guide to the hybridization of nucleic acids is found in Tijssen (1993) Laboratory Techniques in Biochemistry and Molecular Biology-Hybridization with Nucleic Acid Probes part 1 chapter 2 "Overview of principles of hybridization and the strategy of nucleic acid probe assays", Elsevier, N.Y. Generally, highly stringent hybridization and wash conditions are selected to be about 5° C. to 20° C. (preferably 5° C.) lower than the thermal melting point ($T_m$) for the specific sequence at a defined ionic strength and pH. Typically, under highly stringent conditions a probe will hybridize to its target subsequence, but to no other unrelated sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids that have more than 100 complementary residues on a filter in a Southern or Northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash conditions for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization.

Sequence variants that encode a polypeptide with the same biological activity as the anti-cancer compounds or factors described herein and hybridize under moderate to high stringency hybridization conditions are considered to be within the scope of the present invention.

It is further appreciated that such sequence variants may or may not hybridize to the parent sequence under conditions of high stringency. This would be possible, for example, when the sequence variant includes a different codon for each of the amino acids encoded by the parent nucleotide. Such variants are, nonetheless, specifically contemplated and encompassed by the present invention.

III. Gene Delivery Vectors

The present invention contemplates the use of any vector for introduction of one or more genes encoding anti-cancer compounds or factors into mammalian cells. Exemplary vectors include but are not limited to, viral and non-viral vectors, such as retroviruses (including lentiviruses), adenovirus (Ad) vectors including replication competent, replication deficient and gutless forms thereof, adeno-associated virus (AAV) vectors, simian virus 40 (SV-40) vectors, bovine papilloma virus vectors, Epstein-Barr virus vectors, herpes virus vectors, vaccinia virus vectors, Moloney murine leukemia virus vectors, Harvey murine sarcoma virus vectors, murine mammary tumor virus vectors, Rous sarcoma virus vectors and nonviral plasmid vectors. In one preferred approach, the vector is a viral vector. Viruses can efficiently transduce cells and introduce their own DNA into a host cell. In generating recombinant viral vectors, non-essential genes are replaced with a gene or coding sequence for a heterologous (or non-native) protein.

In constructing viral vectors, non-essential genes are replaced with one or more genes encoding one or more therapeutic compounds or factors. Typically, the vector comprises an origin of replication and the vector may or may not also comprise a "marker" or "selectable marker" function by which the vector can be identified and selected. While any selectable marker can be used, selectable markers for use in such expression vectors are generally known in the art and the choice of the proper selectable marker will depend on the host cell. Examples of selectable marker genes which encode proteins that confer resistance to antibiotics or other toxins include ampicillin, methotrexate, tetracycline, neomycin (Southern et al., J., J Mol Appl Genet. 1982;1(4):327–41 (1982)), mycophenolic acid (Mulligan et al., Science 209:1422–7 (1980)), puromycin, zeomycin, hygromycin (Sugden et al., Mol Cell Biol. 5(2): 410–3 (1985)) or G418.

Reference to a vector or other DNA sequences as "recombinant" merely acknowledges the operable linkage of DNA sequences which are not typically operably linked as isolated from or found in nature. Regulatory (expression/control) sequences are operatively linked to a nucleic acid coding sequence when the expression/control sequences regulate the transcription and, as appropriate, translation of the nucleic acid sequence. Thus expression/control sequences can include promoters, enhancers, transcription terminators, a start codon (i.e., ATG) in front of the coding sequined, splicing signal for introns and stop codons.

Adenovirus gene therapy vectors are known to exhibit strong expression in vitro, excellent titer, and the ability to transduce dividing and non-dividing cells in vivo (Hitt et al., Adv in Virus Res 55:479–505 (2000)). When used in vivo these vectors lead to strong but transient gene expression due to immune responses elicited to the vector backbone. The recombinant Ad vectors for use in the instant invention comprise: (1) a packaging site enabling the vector to be incorporated into replication-defective Ad virions; and (2) a therapeutic compound coding sequence. Other elements necessary or helpfull for incorporation into infectious virions, include the 5' and 3' Ad ITRs, the E2 and E3 genes, etc.

Replication-defective Ad virions encapsulating the recombinant Ad vectors of the instant invention are made by standard techniques known in the art using Ad packaging cells and packaging technology. Examples of these methods may be found, for example, in U.S. Pat. No. 5,872,005, incorporated herein by reference in its entirety. A therapeutic compound-encoding gene is commonly inserted into adenovirus in the deleted E1A, E1B or E3 region of the virus genome. Preferred adenoviral vectors for use in practicing the invention do not express one or more wild-type Ad gene products, e.g., E1a, E1b, E2, E3, E4. Preferred embodiments are virions that are typically used together with packaging cell lines that complement the functions of E1, E2A, E4 and optionally the E3 gene regions. See, e.g. U.S. Pat. Nos. 5,872,005, 5,994,106, 6,133,028 and 6,127,175, expressly incorporated by reference herein in their entirety. Adenovirus vectors are purified and formulated using standard techniques known in the art.

Recombinant AAV vectors are characterized in that they are capable of directing the expression and the production of the selected transgenic products in targeted cells. Thus, the recombinant vectors comprise at least all of the sequences of AAV essential for encapsidation and the physical structures for infection of target cells.

Recombinant AAV (rAAV) virions for use in practicing the present invention may be produced using standard methodology, known to those of skill in the art and are constructed such that they include, as operatively linked components in the direction of transcription, control sequences including transcriptional initiation and termination sequences, and the coding sequence for a therapeutic compound or biologically active fragment thereof. These components are bounded on the 5' and 3' end by functional AAV ITR sequences. By "functional AAV ITR sequences" is meant that the ITR sequences function as intended for the rescue, replication and packaging of the AAV virion. Hence, AAV ITRs for use in the vectors of the invention need not have a wild-type nucleotide sequence, and may be altered by the insertion, deletion or substitution of nucleotides or the AAV ITRs may be derived from any of several AAV serotypes. An AAV vector is a vector derived from an adeno-associated virus serotype, including without limitation, AAV-1, AAV-2, AAV-3, AAV-4, AAV-5, AAV-6, AAV-7, AAV-8, etc. Preferred AAV vectors have the wild type REP and CAP genes deleted in whole or part, but retain functional flanking ITR sequences. Table 1 illustrates exemplary AAV serotypes for use in gene transfer.

TABLE 1

AAV Serotypes For Use In Gene Transfer.

| Serotype | Origin | Genome Size (bp) | Homology vs AAV2 | Immunity in Human Population |
|---|---|---|---|---|
| AAV-1 | Human Specimen | 4718 | NT: 80% AA: 83% | NAB: 20% |
| AAV-2 | Human Genital Abortion tissue Amnion Fluid | 4681 | NT: 100% AA: 100% | NAB: 27–53% |
| AAV-3 | Human Adenovirus Specimen | 4726 | NT: 82% AA: 88% | cross reactivity with AAV2 NAB |
| AAV-4 | African Green Monkey | 4774 | NT: 66% AA: 60% | Unknown |
| AAV-5 | Human Genital Lesion | 4625 | NT: 65% AA: 56% | ELISA: 45% NAB: 0% |
| AAV-6 | Laboratory isolate | 4683 | NT: 80% AA: 83% | 20% |
| AAV-7 | Isolated from Heart DNA of Rhesus Monkey | 4721 | NT: 78% AA: 82% | NAB: <1:20 (~5%) |

TABLE 1-continued

AAV Serotypes For Use In Gene Transfer.

| Serotype | Origin | Genome Size (bp) | Homology vs AAV2 | Immunity in Human Population |
|---|---|---|---|---|
| AAV-8 | Isolated from Heart DNA of Rhesus Monkey | 4393 | NT: 79% AA: 83% | NAB: <1:20 (~5%) |

Typically, an AAV expression vector is introduced into a producer cell, followed by introduction of an AAV helper construct, where the helper construct includes AAV coding regions capable of being expressed in the producer cell and which complement AAV helper functions absent in the AAV vector. The helper construct may be designed to down regulate the expression of the large REP proteins (Rep78 and Rep68), typically by mutating the start codon following p5 from ATG to ACG, as described in U.S. Pat. No. 6,548,286, expressly incorporated by reference herein. This is followed by introduction of helper virus and/or additional vectors into the producer cell, wherein the helper virus and/or additional vectors provide accessory functions capable of supporting efficient rAAV virus production. The producer cells are then cultured to produce rAAV. These steps are carried out using standard methodology. Replication-defective AAV virions encapsulating the recombinant AAV vectors of the instant invention are made by standard techniques known in the art using AAV packaging cells and packaging technology. Examples of these methods may be found, for example, in U.S. Pat. Nos. 5,436,146; 5,753,500, 6,040,183, 6,093,570 and 6,548,286, expressly incorporated by reference herein in their entirety. Further compositions and methods for packaging are described in Wang et al. (US 2002/0168342), also incorporated by reference herein in its entirety, and include those techniques within the knowledge of those of skill in the art.

Approximately 40 serotypes of AAV are currently known, however, new serotypes and variants of existing serotypes are still being identified today and are considered within the scope of the present invention. See Gao et al (2002), PNAS 99(18):11854–9; Gao et al (2003), PNAS 100(10):6081–6; Bossis and Chiorini (2003), J. Virol. 77(12):6799–810). Different AAV serotypes are used to optimize transduction of particular target cells or to target specific cell types within a particular target tissue, such as the brain. The use of different AAV serotypes may facilitate targeting of malignant tissue. AAV serotypes including 1, 2, 4, 5 and 6 have been shown to transduce brain tissue. See, e.g., Davidson et al (2000), PNAS 97(7)3428–32; Passini et al (2003), J. Virol 77(12):7034–40). Particular AAV serotypes may more efficiently target and/or replicate in target tissue or cells. A single self-complementary AAV vector can be used in practicing the invention in order to increase transduction efficiency and result in faster onset of transgene expression (McCarty et al., Gene Ther. 2001 Aug; 8(16):1248–54).

In practicing the invention, host cells for producing rAAV virions include mammalian cells, insect cells, microorganisms and yeast. Host cells can also be packaging cells in which the AAV REP and CAP genes are stably maintained in the host cell or alternatively host cells can be producer cells in which the AAV vector genome is stably maintained. Exemplary packaging and producer cells are derived from 293, A549 or HeLa cells. AAV vectors are purified and formulated using standard techniques known in the art.

Retroviral vectors are a common tool for gene delivery (Miller, 1992, Nature 357: 455–460). Retroviral vectors and more particularly lentiviral vectors may be used in practicing the present invention. Retroviral vectors have been tested and found to be suitable delivery vehicles for the stable introduction of a variety of genes of interest into the genomic DNA of a broad range of target cells. The ability of retroviral vectors to deliver unrearranged, single copy transgenes into cells makes retroviral vectors well suited for transferring genes into cells. Further, retroviruses enter host cells by the binding of retroviral envelope glycoproteins to specific cell surface receptors on the host cells. Consequently, pseudotyped retroviral vectors in which the encoded native envelope protein is replaced by a heterologous envelope protein that has a different cellular specificity than the native envelope protein (e.g., binds to a different cell-surface receptor as compared to the native envelope protein) may also find utility in practicing the present invention. The ability to direct the delivery of retroviral vectors encoding a transgene to a specific type of target cells is highly desirable for gene therapy applications.

The present invention provides retroviral vectors which include e.g., retroviral transfer vectors comprising one or more transgene sequences and retroviral packaging vectors comprising one or more packaging elements. In particular, the present invention provides pseudotyped retroviral vectors encoding a heterologous or functionally modified envelope protein for producing pseudotyped retrovirus.

The core sequence of the retroviral vectors of the present invention may be readily derived from a wide variety of retroviruses, including for example, B, C, and D type retroviruses as well as spumaviruses and lentiviruses (see RNA Tumor Viruses, Second Edition, Cold Spring Harbor Laboratory, 1985). An example of a retrovirus suitable for use in the compositions and methods of the present invention includes, but is not limited to, lentivirus. Other retroviruses suitable for use in the compositions and methods of the present invention include, but are not limited to, Avian Leukosis Virus, Bovine Leukemia Virus, Murine Leukemia Virus, Mink-Cell Focus-Inducing Virus, Murine Sarcoma Virus, Reticuloendotheliosis virus and Rous Sarcoma Virus. Particularly preferred Murine Leukemia Viruses include 4070A and 1504A (Hartley and Rowe, J. Virol. 19:19–25, 1976), Abelson (ATCC No. VR-999), Friend (ATCC No. VR-245), Graffi, Gross (ATCC No. VR-590), Kirsten, Harvey Sarcoma Virus and Rauscher (ATCC No. VR-998), and Moloney Murine Leukemia Virus (ATCC No. VR-190). Such retroviruses may be readily obtained from depositories or collections such as the American Type Culture Collection ("ATCC"; Rockville, Md.), or isolated from known sources using commonly available techniques.

Preferably, a retroviral vector sequence of the present invention is derived from a lentivirus. A preferred lentivirus is a human immunodeficiency virus, e.g., type 1 or 2 (i.e., HIV-1 or HIV-2, wherein HIV-1 was formerly called lymphadenopathy associated virus 3 (HTLV-III) and acquired immune deficiency syndrome (AIDS)-related virus (ARV)), or another virus related to HIV-1 or HIV-2 that has been identified and associated with AIDS or AIDS-like disease. Other lentivirus vectors include, a sheep Visna/maedi virus, a feline immunodeficiency virus (FIV), a bovine lentivirus, simian immunodeficiency virus (SIV), an equine infectious anemia virus (EIAV), and a caprine arthritis-encephalitis virus (CAEV).

The various genera and strains of retroviruses suitable for use in the compositions and methods are well known in the art (see, e.g., Fields Virology, Third Edition, edited by B. N. Fields et al., Lippincott-Raven Publishers (1996), see e.g., Chapter 58, Retroviridae: The Viruses and Their Replication, Classification, pages 1768–1771, including Table 1, incorporated herein by reference).

The present invention provides retroviral packaging systems for generating producer cells and producer cell lines that produce retroviruses, and methods of making such packaging systems. Accordingly, the present invention also provides producer cells and cell lines generated by introducing a retroviral transfer vector into such packaging systems (e.g., by transfection or infection), and methods of making such packaging cells and cell lines.

The retroviral packaging systems for use in practicing the present invention comprise at least two packaging vectors: a first packaging vector which comprises a first nucleotide sequence comprising a gag, a pol, or gag and pol genes; and a second packaging vector which comprises a second nucleotide sequence comprising a heterologous or functionally modified envelope gene. In a preferred embodiment, the retroviral elements are derived from a lentivirus, such as HIV. Preferably, the vectors lack a functional tat gene and/or functional accessory genes (vif, vpr, vpu, vpx, nef). In another preferred embodiment, the system further comprises a third packaging vector that comprises a nucleotide sequence comprising a rev gene. The packaging system can be provided in the form of a packaging cell that contains the first, second, and, optionally, third nucleotide sequences.

The invention is applicable to a variety of retroviral systems, and those skilled in the art will appreciate the common elements shared across differing groups of retroviruses. The description herein uses lentiviral systems as a representative example. However, all retroviruses share the features of enveloped virions with surface projections and containing one molecule of linear, positive-sense single stranded RNA, a genome consisting of a dimer, and the common proteins gag, pol and env.

Lentiviruses share several structural virion proteins in common, including the envelope glycoproteins SU (gp120) and TM (gp41), which are encoded by the env gene; CA (p24), MA (p17) and NC (p7–11), which are encoded by the gag gene; and RT, PR and IN encoded by the pol gene. HIV-1 and HIV-2 contain accessory and other proteins involved in regulation of synthesis and processing virus RNA and other replicative functions. The accessory proteins, encoded by the vif, vpr, vpu/vpx, and nef genes, can be omitted (or inactivated) from the recombinant system. In addition, tat and rev can be omitted or inactivated, e.g., by mutation or deletion.

First generation lentiviral vector packaging systems provide separate packaging constructs for gag/pol and env, and typically employ a heterologous or functionally modified envelope protein for safety reasons. In second generation lentiviral vector systems, the accessory genes, vif, vpr, vpu and nef, are deleted or inactivated. Third generation lentiviral vector systems are those from which the tat gene has been deleted or otherwise inactivated (e.g., via mutation).

Compensation for the regulation of transcription normally provided by tat can be provided by the use of a strong constitutive promoter, such as the human cytomegalovirus immediate early (HCMV-IE) enhancer/promoter. Other promoters/enhancers can be selected based on strength of constitutive promoter activity, specificity for target tissue (e.g., liver-specific promoter), or other factors relating to desired control over expression, as is understood in the art. For example, in some embodiments, it is desirable to employ an inducible promoter such as tet to achieve controlled expression. The gene encoding rev is preferably provided on a separate expression construct, such that a typical third generation lentiviral vector system will involve four plasmids: one each for gagpol, rev, envelope and the transfer vector. Regardless of the generation of packaging system employed, gag and pol can be provided on a single construct or on separate constructs.

Typically, the packaging vectors are included in a packaging cell, and are introduced into the cell via transfection, transduction or infection. Methods for transfection, transduction or infection are well known by those of skill in the art. A retroviral transfer vector of the present invention can be introduced into a packaging cell line, via transfection, transduction or infection, to generate a producer cell or cell line. The packaging vectors of the present invention can be introduced into human cells or cell lines by standard methods including, e.g., calcium phosphate transfection, lipofection or electroporation. In some embodiments, the packaging vectors are introduced into the cells together with a dominant selectable marker, such as neo, DHFR, Gln synthetase or ADA, followed by selection in the presence of the appropriate drug and isolation of clones. A selectable marker gene can be linked physically to genes encoding by the packaging vector.

Stable cell lines, wherein the packaging functions are configured to be expressed by a suitable packaging cell, are known. For example, see U.S. Pat. No. 5,686,279; and Ory et al., Proc. Natl. Acad. Sci. (1996) 93:11400–11406, which describe packaging cells. Further description of stable cell line production can be found in Dull et al., 1998, J. Virology 72(11):8463–8471; and in Zufferey et al., 1998, J. Virology 72(12):9873–9880

Zufferey et al., 1997, Nature Biotechnology 15:871–875, teach a lentiviral packaging plasmid wherein sequences 3' of pol including the HIV-1 envelope gene are deleted. The construct contains tat and rev sequences and the 3' LTR is replaced with poly A sequences. The 5' LTR and psi sequences are replaced by another promoter, such as one which is inducible. For example, a CMV promoter or derivative thereof can be used.

The packaging vectors of interest may contain additional changes to the packaging functions to enhance lentiviral protein expression and to enhance safety. For example, all of the HIV sequences upstream of gag can be removed. Also, sequences downstream of envelope can be removed. Moreover, steps can be taken to modify the vector to enhance the splicing and translation of the RNA.

Optionally, a conditional packaging system is used, such as that described by Dull et al., 1998, J. Virology 72(11): 8463–8471. Also preferred is the use of a self-inactivating vector (SIN), which improves the biosafety of the vector by deletion of the HIV-1 long terminal repeat (LTR) as described, for example, by Zufferey et al., 1998, J. Virology 72(12):9873–9880. Inducible vectors can also be used, such as through a tet-inducible LTR.

IV. Regulatory Elements

The gene therapy vectors of the invention typically include heterologous control sequences, which include, but are not limited to tumor selective promoters and enhancers, including but not limited to the E2F promoter and the telomerase (hTERT) promoter; the cytomegalovirus enhancer/chicken beta-actin/Rabbit β-globin promoter (CAG promoter; Niwa H. et al. 1991. Gene 108(2):193–9); the elongation factor 1-alpha promoter (EF 1-alpha) promoter (Kim D W et al. 1990. Gene. 91(2):217–23 and Guo ZS et al. 1996. Gene Ther. 3(9):802–10); a glial specific promoter (e.g. glial fibrary acid protein promoter) and a neuron specific promoter (e.g. neuron specific enolase promoter or synapsin promoter).

In some cases constitutive promoters, such as the cytomegalovirus (CMV) immediate early promoter, the RSV LTR, the MoMLV LTR, the CAG promoter, the phosphoglycerate kinase-1 promoter (PGK) or the SV-40 promtoer may be employed.

The gene therapy vectors of the invention may also include enhancers and coding sequences for signal peptides. The vector constructs may or may not include an intron. Neural or glial specific promoters may be included in the vectors of the invention as a means to limit expression to specific cell types in the brain. Thus it will be appreciated that gene therapy vectors of the invention may include any of a number of transgenes, combinations of transgenes and transgene/regulatory element combinations. The specific elements included in exemplary vector constructs for use in practicing the invention and abbreviations therefor are provided in Table 2, below. Exemplary vectors are described in Table 3 and exemplary combinations of vectors for treatment of cancer are described in Table 4.

TABLE 2

Elements Of Vectors For Use In Practicing the Invention.

| Abbreviation | Element |
|---|---|
| CAG | sequence for CMV promoter coupled to intron from chicken globin splice acceptor and rabbit globin splice donor |
| EF1α | human elongation factor 1α gene promoter sequence (with intron) |
| E2F | E2F promoter sequence |
| TERT | telomerase promoter sequence |
| WPRE | sequence for woodchuck hepatitis virus post-transcriptional regulatory element (SEQ ID NO: 25) |
| bGHpolyA | bovine growth hormone polyadenylation signal sequence (SEQ ID NO: 26) |
| HSVtk | sequence encoding herpes simplex virus thymidine kinase |
| codA | sequence encoding bacterial cytosine deaminase |
| fcy | sequence encoding yeast cytosine deaminase |
| fcy::fur | sequence encoding fusion of yeast cytosine deaminase and yeast uracil phosphoribosyl transferase |
| hTRAIL | sequence encoding human TNF-related apoptosis inducing ligand - membrane bound TRAIL (SEQ ID NO: 1) |
| LZsTRAIL | sequence encoding isoleucine modified soluble TRAIL (SEQ ID NO: 3) |
| PF4 | sequence encoding platelet factor 4 (SEQ ID NO: 6) |
| PF-4 DLR | sequence encoding soluble platelet factor-4 with C-terminus DLR mutation (SEQ ID NO: 8) |
| βgb polyA | polyadenylation signal from human β-globin gene |
| sKDRFc | sequence encoding soluble VEGF receptor 2 chimera |
| FltFc | sequence encoding vascular endothelial growth factor (VEGF) receptor 1 chimera |
| VEGF | sequence encoding vascular endothelial growth factor (VEGF) |
| αKDRmAb | sequence encoding anti KDR monoclonal antibody |
| TIMP3 | sequence encoding tissue inhibitor of metalloproteinases 3 |
| VEGFR3Fc | sequence encoding soluble VEGF receptor 3 chimera |
| VEGF-TRAP | sequence encoding VEGF-TRAP (SEQ ID NO: 12) |

TABLE 3

Exemplary Vectors For Treatment Of Cancer.

| | |
|---|---|
| rAAV-CAG-HSVtk-WPRE-bGHpolyA | rAAV-CAG-VEGF-Trap-WPRE-bGHpolyA |
| rAAV-CAG-codA-WPRE-bGHpolyA | rAAV-CAG-αKDRmAb-WPRE-bGHpolyA |
| rAAV-CAG-fcy-WPRE-bGHpolyA | rAAV-CAG-TIMP3-WPRE-bGHpolyA |
| rAAV-CAG-fcy::fur-WPRE-bGHpolyA | rAAV-CAG-sPF4-WPRE-bGHpolyA |
| rAAV-CAG-hTRAIL-WPRE-bGHpolyA | rAAV-EF1α-HSVtk-WPRE-bGHpolyA |
| rAAV-CAG-sTRAIL-WPRE-bGHpolyA | rAAV-EF1α-codA-WPRE-bGHpolyA |
| rAAV-CAG-PF4-WPRE-bGHpolyA | rAAV-EF1α-fcy-WPRE-bGHpolyA |
| rAAV-CAG-sKDRFc-WPRE-bGHpolyA | rAAV-EF1α-fcy::fur-WPRE-bGHpolyA |
| rAAV-CAG-FltFc-WPRE-bGHpolyA | rAAV-EF1α-hTRAIL-WPRE-bGHpolyA |
| rAAV-EF1α-sPF4-WPRE-bGHpolyA | rAAV-EF1α-sPF4-WPRE-bGHpolyA |
| rAAV-EF1α-sTRAIL-WPRE-bGHpolyA | rAAV-EF1α-sTRAIL-WPRE-bGHpolyA |
| rAAV-EF1α-PF4-WPRE-bGHpolyA | rAAV-EF1α-PF4-WPRE-bGHpolyA |
| rAAV-EF1α-sKDRFc-WPRE-bGHpolyA | rAAV-EF1α-sKDRFc-WPRE-bGHpolyA |
| rAAV-EF1α-FltFc-WPRE-bGHpolyA | rAAV-EF1α-FltFc-WPRE-bGHpolyA |
| rAAV-EF1α-VEGF-Trap-WPRE-bGHpolyA | rAAV-EF1α-VEGF-Trap-WPRE-bGHpolyA |
| rAAV-EF1α-αKDRmAb-WPRE-bGHpolyA | rAAV-EF1α-αKDRmAb-WPRE-bGHpolyA |
| rAAV-EF1α-TIMP3-WPRE-bGHpolyA | rAAV-EF1α-TIMP3-WPRE-bGHpolyA |
| rAAV-E2F-HSVTK-WPRE-bGHpolyA | rAAV-E2F-HSVTK-WPRE-bGHpolyA |
| rAAV-E2F-codA-WPRE-bGHpolyA | rAAV-tert-codA-WPRE-bGHpolyA |
| rAAV-E2F-fcy-WPRE-bGHpolyA | rAAV-tert-fcy-WPRE-bGHpolyA |
| rAAV-E2F-fcy::fur-WPRE-bGHpolyA | rAAV-tert-fcy::fur-WPRE-bGHpolyA |
| rAAV-tert-HSVTK-WPRE-bGHpolyA | |

TABLE 4

Exemplary Combinations Of Vectors For Treatment Of Cancer.

| | |
|---|---|
| HSVtk + fcy | fcy + PF4 |
| HSVtk + codA | codA + TRAIL |
| HSVtk + fcy::fur | codA + PF4 |
| TRAIL + TIMP-3 | PF-4 + TIMP-3 |
| HSVtk + TRAIL | fcy::fur + TRAIL |
| HSVtk + PF4 | fcy::fur + PF4 |
| fcy + TRAIL | TRAIL + PF4 |
| VEGF-Trap + PF-4 | |

The vector components and combinations provided above are for purposes of illustration. It will be appreciated that any combination of the anti-cancer factos coding sequences, promoters and vectors described herein are considered to be within the scope of the invention. In one preferred embodiment, a vector encoding a suicide gene under the control of a tumor-specific promoter and a pro-apoptotic or anti-angiogenic gene under the control of a ubiquitous promoter is provided. While the mechanism is not part of the invention, in this sort of vector, both the suicide gene and the pro-apoptotic or anti-angiogenic gene would be expressed in malignant cells. Suicide gene expression would result in death of transduced cells following pro-drug treatment. Normal cells surrounding the tumor, however, would only express the pro-apoptotic or anti-angiogenic gene resulting in long-term expression.

Expression of a combination or more than one transgene from a single promoter can be facilitated using an IRES (ECMV, eIF4, etc.) or two promoters. Alternatively, a self processing cleavage site such as the foot-and-mouth disease virus 2A protein "cleavage" site can be used to express multiple proteins from a single mRNA message. (See, e.g., Furler et al (2001), Gene Therapy 8(11):864–73 and U.S. Ser. No. 10/831,304).

V. Regulated expression

The present invention contemplates the inclusion of a gene regulation system for the controlled expression of one or more anti-cancer compounds or factors. Gene regulation systems are useful in the modulated expression of a particular gene or genes. In one exemplary approach, a gene regulation system or switch includes a chimeric transcription factor that has a ligand binding domain, a transcriptional activation domain and a DNA binding domain. The domains may be obtained from virtually any source and may be combined in any of a number of ways to obtain a novel protein. A regulatable gene system also includes a DNA response element which interacts with the chimeric transcription factor. This element is located adjacent the gene to be regulated.

Exemplary gene regulation systems that may be employed in practicing the present invention include, the *Drosophila* ecdysone system (Yao and Evans, 1996, Proc. Nat. Acad. Sci., 93:3346), the *Bombyx* ecdysone system (Suhr et al., 1998, Proc. Nat. Acad. Sci., 95:7999), the Valentis GeneSwitch® synthetic progesterone receptor system which employs RU-486 as the inducer (Osterwalder et al., 2001, Proc Natl Acad Sci 98(22):12596–601); the Tet™ & RevTet™ Systems (BD Biosciences Clontech), which employ small molecules, such as tetracycline (Tc) or analogues, e.g. doxycycline, to regulate (turn on or off) transcription of the target (Knott A et al., Biotechniques 2002, 32(4):796, 798, 800); and ARIAD Regulation Technology which is based on the use of a small molecule to bring together two intracellular molecules, each of which is linked to either a transcriptional activator or a DNA binding protein. When these components come together, transcription of the gene of interest is activated. Two major systems which employ the ARIAD technology include a system based on homodimerization and a system based on heterodimerization (Rivera et al., 1996, Nature Med, 2(9): 1028–1032; Ye et al., 2000, Science 283: 88–91).

Preferred gene regulation systems for use in practicing the present invention are the ARIAD Regulation Technology and the Tet™ & RevTet™ Systems.

VI. Introduction of Gene Therapy Vectors into cells

In Vitro or Ex Vivo

The gene therapy vectors and constructs described above may be introduced into cells using standard methodology known in the art. Such techniques include transfection using calcium phosphate, micro-injection into cultured cells (Capecchi, Cell 22:479–488 [1980]), electroporation (Shigekawa et al., BioTechn., 6:742–751 [1988]), liposome-mediated gene transfer (Mannino et al., BioTechn., 6:682–690 [1988]), lipid-mediated transduction (Felgner et al., Proc. Natl. Acad. Sci. USA 84:7413–7417 [1987]), and nucleic acid delivery using high-velocity microprojectiles (Klein et al., Nature 327:70–73 [1987]).

Exemplary assays for in vitro evaluation of the efficacy of various vectors and vector combinations include the following: a determination of transduction efficiency in cancer cell lines and in normal cell lines derived from corresponding tissue types; evaluation as to whether the particular AAV serotypes exhibit target sell specificity, e.g., the relative selectivity of AAV5 as it relates to a 2,3-sialic acid moiety and/or PDGFR-α (platelet derived growth factor receptor-α) overabundance on glioma cells; an in vitro evaluation of cytotoxicity, e.g., a comparison of genes (including a comparison of TK, CD, and dCK) and other pro-apoptotic genes performed using direct tumor cell transduction or conditioned media from transduced cells and an in vitro proliferation assay, such as an assay using MTT or a WST-8-based tetrazolium cytotoxicity assay; annexin staining for apoptotic response; tunel assays; assays for prodrug activation (such as thymidine phosphorylation and cytosine deamination); evaluation of transgene expression using for example ELISA or Western blot; enzymatic activity assay using a SCX column for CD, and a DE-81 filter for TK, an in vitro proliferation assay (for anti-angiogenic genes such as PF4) by direct endothelial cell (EC) transduction and/or transduction of bystander cells co-cultured with ECs.

A preliminary study involved examination of AAV serotype transduction in vitro using the rAAV vector construct shown in FIG. 1. The vector was used to evaluate transduction of CNS-derived primary cells and glioma cell lines in vitro 48 hours post-infection based on transduction with AAV2, AAV5, AAV6, AAV7 and AAV8 each of which expressed GFP as a reporter gene. The greatest level of transduction, evaluated by counting GFP positive cells, was observed with AAV2 and AAV6 for LN-18, astrocytes, U87MG and C6 cells (data not shown).

In Vivo

Exemplary assays for in vivo evaluation of the efficacy of various vectors and vector combinations include the various studies in animal models, such as delivery to normal and tumor-bearing animals, wherein anti-angiogenic, pro-apoptotic and other cytotoxic genes (e.g., TK, CD, dCK) are compared. In application of the methods and compositions of the invention to brain cancer, the parameters evaluated may further include convection enhanced delivery (CED)

vs. stereotactic injection in non-human primates and dogs; evaluation of the effect of heparin on AAV-2 transduction in the CNS; use of orthotopic brain tumor models in rodents employing glioma cell lines such as the U87, 4C8 and U251, wherein exemplary studies are carried out using an orthotopic model of glioma in rats. In such cases, experiments are designed to look at tumor size and survival and the use of subcutaneous models for glioma in mice with measurement of transgene expression, assays for tumor cell death and evaluation of a combination of vectors.

Initial in vivo studies are typically directed to select the best suited serotype of AAV for efficient transduction of a selected target tissue and the expression of one or more transgenes. Such studies rely on a number of in vitro and in vivo assays including, but not limited to, in vivo evaluation of recombinant AAV vectors encoding TK, CD, CD::UPRT and TRAIL in the treatment of subcutaneous U87 human glioma tumors (Example 2), hydrodynamic gene transfer of anti-angiogenic compounds such as PF-4, PF-4DLR (Example 3), TRAIL (Examples 4 and 5), VEGF-TRAP (Examples 7, 8 and 9), and VEGF-TRAP plus PF4 (Example 10).

VII. Evaluation of the Expression of Anti-Angiogenic Factors

The effectiveness of a given vector encoding an anti-angiogenic compound or factor may be evaluated in vitro using any of a number of methods known in the art. Exemplary in vitro angiogenesis assays include, but are not limited to, an endothelial cell migration assay, a Matrigel tube formation assay, endothelial and tumor cell proliferation assays, apoptosis assays, aortic ring assays and CAM assays.

The rate of endothelial cell migration is evaluated using human umbilical vein endothelial cells (HUVEC) using a modified Boyden chamber assay as described by Clyman et al., 1994, Cell Adhes Commun. 1(4):333–42 and Lin, P et al., 1998, Cell Growth Differ. 9(1):49–58. A matrigel tube formation assay is used to demonstrate differentiation of endothelial cells. In carrying out the assay, endothelial cells are layered on top of an extracellular matrix (Matrigel), Cell. 1994, 79(2):315–28 and Lucas et al., 1998, Blood 92(12): 4730–41. Endothelial and tumor cell proliferation assays may be used to demonstrate the inhibitory effects of vector produced anti-angiogenic factors on cell proliferation. An aortic ring assay has been used to demonstrate the inhibition of microvessel outgrowth of rat aorta rings by virally produced angiostatin and endostatin (Kruger, E. A. et al., 2000, Biophys. Res. Comm. 268, 183–191). Tumor cell apoptosis may also be evaluated as a further indicator of anti-angiogenic activity.

Exemplary in vivo angiogenesis models include, but are not limited to, in a B16 B1/6 Mouse melanoma metastasis model (described below); a B16F10-luc metastasis model with Xenogen Imaging (described below); a Lewis Lung Carcinoma (LLC) Xenograft Resection Model (O'Reilly et al, 1994, Cell. 79(2):315–28); a LLC-luc metastasis model/Xenogen Imaging; a LLC-luc SC resection model/Xenogen Imaging; a RIP-Tag pancreatic islet carcinoma transgenic model (Hanahan et al., Nature, 315(6015):115–122, 1985 and Bergers et al., Science, 284:808–811, 1999); an orthotopic breast cancer model MDA-231 (Hiraga T. et al., 2001, Cancer Res. 61(11):4418–24); a C6 glioma model (Griscelli F, et al., 1998, Proc Natl Acad Sci USA. 95(11):6367–72); an LnCP prostate cancer model (Horoszewicz J S et al., Cancer Res. 43(4):1809–18, 1983); and a PC-3 Xenograft pancreatic tumor model (Donaldson J T et al., 1990, Int J Cancer. 46(2):238–44).

VIII. Evaluation of the Expression of Pro-Apoptotic Factors

The effectiveness of a given vector encoding a pro-apoptotic compound or factor may be evaluated in vitro using any of a number of methods known in the art. Exemplary in vitro apoptosis assays include, but are not limited to, DNA fragmentation assays and caspase assays, as further described below.

Exemplary in vivo models for evaluation of pro-apoptotic factors include, but are not limited to those described above for anti-angiogenic compounds or factors.

IX. Therapeutic Applications of Anti-Cancer Gene Therapy

The invention contemplates administration of the recombinant vectors to a patient with cancer in order to slow or completely halt the growth of cancer cellsr. Administration to the patient may be by any known method, including both in vivo and ex vivo modes of administration.

In vivo delivery involves delivery of a gene therapy vector of the invention directly to a patient. In some cases, the vector is delivered to a depot organ, e.g., liver or muscle, by intraportal (IP) or intramuscular (IM) injection, respectively that generates and secretes the transgene product of interest. In other approaches, the vector is delivered intravenously (IV). Such delivery may also be by the intraperitoneal route or by delivery directly to the tumor site. Convection-enhanced delivery to the brain is also contemplated. Non-invasive methods, such as oral delivery, are also contemplated. In some cases, delivery may be accomplished by an ex vivo route. Ex vivo delivery involves ex vivo (outside the body) transduction of cells by the recombinant vectors, followed by administration of the transduced cells to the patient.

The gene therapy vectors of the invention are delivered in an amount effective yield to a therapeutic level of the therapeutic factor or factors encoded by the vector(s) in the vicinity of cancer cells or a tumor.

The present invention contemplates treatment regimens that include the use of gene therapy vectors that encode an anti-cancer compound, alone or in combination with one or more additional anti-cancer compounds and may further include any of a number of modes of therapeutic intervention typically employed by those of skill in the art to treat the type of cancer under therapy. In general standard therapeutic regimens for cancer treatment may be employed, including surgery, chemotherapy, radiation therapy and immunotherapy. Chemotherapeutic agents for use in practicing the invention include any agents with established use in treatment of cancer.

Accordingly, the present invention includes improved cancer treatment regimens that involve the use of gene therapy vectors that encode one or more anti-cancer compounds, in combination with one or more of chemotherapy, radiation therapy and immunotherapy methods.

All patent and literature references cited in the present specification are hereby incorporated by reference in their entirety.

X. Materials and Methods

Immunoprecipitation

Western blots of virus produced anti-cancer compounds are carried out using standard methodologies routinely employed by those of skill in the art.

Cultured Cells

Human umbilical vein endothelial cells (HUVEC), and Human Microvascular Endothelial cells (HMVEC) are obtained from Clonetics (Walkersville, Md.). Primary endothelial cells are cultured in EGM-2 (Clonetics) supplemented with 20% of fetal calf serum, 1 mM glutamine, 1 mg/ml hydrocortisone, and 10 ng/ml epithelium growth factor, and infection is performed in the same medium but in 2% fetal calf serum and 3 ng/ml recombinant human basic fibroblast growth factor (R&D Systems). The multiplicity of infection (MOI) is chosen to obtain between 80% and 100% infected cells as judged by 5-bromo-4-chloro-3-indolyl β-D-galactoside staining after infection with Ad CMV β-gal.

Endothelial Cell Migration Assay (Modified Boyden Chamber Migration Assay)

Briefly, a 24-well polycarbonate filter wells (Costar Transwell with an 8 um pore size) are coated with 2% gelatin in PBS for 2–4 hours at room temperature in the cell culture hood, then subsequently incubated at 37 C for 1 h with DMEM containing 0.1% BSA. HUVEC cells are trypsinized, pelleted by centrifugation, washed and resuspended in fresh DMEM/BSA to a final concentration of $2 \times 10^6$ cells/ml. Aliquots of cells $2 \times 10^5$ cells are applied to the upper chamber of the filter wells. The filter inserts with cells are placed in wells of a 24-well culture plate containing either media alone as a control, or media plus human recombinant VEGF or bFGF at 10 ng/ml preincubated for 30 min with conditioned media transduced with adenovirus vectors encoding angiostatin or GFP/lacZ at an MOI of 1–10 and diluted to contain approximately 300 ng/ml of control protein. After a 6 hour incubation at 37 C, the cells that have migrated to the lower surface of the filter inserts are fixed with Diff-Quik (Dade International), fixed for 2 min; solution I for 2 min and solution II for 3 min. Filter inserts are examined under a microscope at 200× magnification.

Matrigel Tube Formation Assay

Matrigel (Beckton Dickinson) is coated onto 24-well cell culture plates on ice, and incubated at 37 C for 30 min. Conditioned medium from transduced cells is collected and assayed for production of an anti-angiogenic protein. Conditioned medium is then titrated to contain 300 ng/ml of control protein and used to layer on top of the matrigel coated plates. $5 \times 10^5$ HUVEC cells are added on top of the conditioned media. Plates are incubated for 12 hours at 37 C, and plates are scored by the total number of junctions formed by the endothelial cells from 5 fields under the microscope. The results are typically reported as the average of 5 fields.

Endothelial and Tumor Cell Proliferation Assays

HUVEC cells are infected with candidate viral vectors at an MOI of 0.1, 1, 10, 100 and collected with 1 mM EDTA, washed twice with PBS, and resuspended. They are seeded into 96-well cell culture plates at 5000 cells/well and cultured for 12 hr, followed by addition of BrdU. DNA synthesis is measured by BrdU incorporation into the cells with a BrdU incorporation assay kit (Roche, Mannheim, Germany).

Cell Cycle Analysis

HUVEC cells are infected with viral vectors at an MOI of 0.1–100 and incubated at 37° C. Cells are harvested after 12–72 hrs by treatment with cell detachment buffer (Sigma) for 2 min and subsequent washes/spins for 2 times. Cells are resuspended into EGM-2 media and treated with propidium iodide in solubilization buffer (Triton, RNAse, etc.) and DNA content is analyzed by FACS analysis (Becton Dickinson).

Aortic Ring Assay 12-well tissue culture plates are covered with Matrigel (Becton-Dickinson, Bedford, Mass.) and allowed to solidify for 1 hours at 37 C incubator. Thoracic aortas are excised from 4–6 week old male Sprague-Dawley rats and the fibroadipose tissue was removed. Aortas are sectioned into 1.2 mm long cross sections. Rinsed numerous times with EGM-2 (Clonetics Inc.), placed on Matrigel coated wells, and covered with additional Matrigel, then allowed to solidify at 37° C. for another hour. The rings are cultured overnight in 2 ml of EGM-2, the next day the media is removed, and the rings are cultured with bFGF and virally produced anti-angiogenic proteins for 4 days.

Apoptosis Assays

HUVEC cells are infected with viral vectors encoding an anti-cancer compound (i.e. a pro-apoptotic gene product) or a marker gene at an MOI of 0.1, 1, 10, 100 and collected with 1 mM EDTA, washed twice with PBS, and resuspended. They are seeded into 96-well cell culture plates at 5000 cells/well and cultured at 37 C. Apoptosis assays are performed on the supernatant of these cells by using the Cell Death Detection ELISAplus kit from Roche (Mannheim, Germany) which is a photometric enzyme-immunoassay that measures cytoplasmic histone-associated-DNA-fragments after induced cell death.

B16 B1/6 Mouse Melanoma Metastasis Model

Female C57B1/6 mice are obtained from Taconic and mice were at 6–8 weeks old at the start of each experiment. Mice are injected with $5 \times 10e4$ B16B1/6 cells on day 0 via tail vein with a 27-gauge needle. After 14–21 days, mice are sacrificed and their tumor burden assessed by harvesting the mice lungs and counting the surface tumor metastasis and measuring the weight of the lung. Experiments typically employ 6–10 animals per group. Statistical significance is evaluated using the Student's t-test.

Xenogen Imaging of Tumor Models

In vivo luminescence of tumor bearing mice is monitored biweekly in B16F10-luciferase (Xenogen Inc.) injected mice. Balb/c nu/nu mice are injected with $5 \times 10e4$ or $2 \times 10e5$ cells of B16F10-luc cells via tail vein on day 0. Mice are monitored for tumor burden when necessary by intra-peritoneal injection of excess luciferin substrate at 1.5 mg/g mice weight. Twenty minutes after substrate injection, mice are anesthesized and monitored for in vivo luminescence with Xenogen IVIS Imaging System (Xenogen Inc.) luminescence sensitive CCD camera by dorsal or ventral position. Data is collected and analyzed by Living Image 2.11 software. CCD photon counts are analyzed by Living Image 2.11 and an Excel spreadsheet.

Chick Chorioallantoic Membrane (CAM) Assays

Hydrocortisone-containing filter discs are soaked with 25 ng Vascular Endothelium Growth Factor (VEGF) (R&D Systems, Minneapolis, Minn.) together with the indicated doses of conditioned media from control or vector transduced cells, and aseptically placed on top of the chorioallantoic membranes of 11 day old chick embryos. After 72 hr incubation, the CAMs are surgically removed, fixed and the discs are analyzed for VEGF-induced angiogenesis by stereomicroscopy. The mean number (+/−SEM) of branch points occurring in the new blood vessel sprouts beneath the applied filter disc from the treated CAMs is enumerated from multiple (n=8–10) samples.

Cytotoxicity/Viability Assays:

Briefly, 1e4 tumor cells (ATCC), or normal primary cells (BioWhittaker), are seeded in one well of a 96-well titer plate and incubated overnight at 37° C. Cells are then treated with the test or control agents for 24, 48 or 72 hr. Following treatment, cell viability is evaluated using a tetrazolium-salt (WST-8) based proliferation assay (Cell Counting Kit-8, Dojindo Laboratories, Japan) according to the manufacturer's recommendations. % Cytotoxicity/Growth inhibition is defined as [1-(OD treated−background)/(OD untreated−background)×100].

DNA Fragmentation (Apoptosis) Assays:

DNA fragmentation is quantitated by a photometric enzyme-immunoassay (Cell Death Detection ELISA Assay, Roche) for measuring cytoplasmic histone-associated nucleosomes according to the manufacturer's protocols. % Apoptosis is defined as relative increase in DNA fragmentation in treated vs. control cells calculated by [O.D. Treated−background]/[Maximal O.D.−Background].

Caspase Assays:

Caspase 3 and Caspase 8 enzymatic activity is quantitated from lysates of treated/untreated tumor cells using commercially available colorimetric assays using the substrate peptides, DEVD-pNA (for Caspase 3) or IETD-pNA (for Caspase 8) (RnD Systems) according to the manufacturer's recommendations. In certain assays, cells are pre-treated with 20 uM of the pan-caspase inhibitor, ZVAD-fmk (RnD Systems), 1 hr prior to stimulation with TRAIL or control agents. The results are reported as relative fold increase of caspase activity in treated cells (minus background) over untreated cells (minus background).

Chemosensitization of Tumor Cells:

Tumor cells are plated at 1e4 cells per well in 96-well plates and incubated overnight at 37 C after which time the cells are left untreated or treated with the indicated sub-toxic doses of chemotherapeutic agents. After 24 hr, the cells are left untreated, or treated with sub-toxic doses of recombinant human TRAIL or AAV-produced TRAIL for an additional 24, 48 or 72 hr. Cell viability is evaluated using a tetrazolium-salt (WST-8) based proliferation assay (Cell Counting Kit-8, Dojindo Laboratories, Japan) according to the manufacturer's recommendations. % Cytotoxicity/Growth Inhibition was defined as [1-(OD treated−background)/(OD untreated−background)×100].

Cells

Human Aortic Endothelial Cells (HAEC), Human Umbilical Vein Endothelial Cells (HUVEC), HumanDermal Microvascular Endothelial Cells (HMVEC), Normal Human Lung Fibroblasts (NHLF), Human Smooth Muscle Cells (CoSMC) and Human Hepatocytes are purchased from BioWhittaker/Clonetics (Walkersville, Md.) and cultured according to the specifications provided by the manufacturer. Tumor cells are purchased from ATCC and cultured under standard conditions in Dulbecco's Modified Media (DMEM) supplemented with 10% Fetal Bovine Serum.

Detection of TRAIL by Immunoblotting and ELISA:

Aliquots of conditioned media containing AAV-generated sTRAIL, or recombinant human TRAIL (RnD Systems), are resolved by 12% PAGE and immunoblotted onto nitrocellulose. Membranes are probed with a goat anti-human TRAIL polyclonal antibody (RnD Systems) as a primary antibody, followed by incubation with HRP-conjugated anti-goat IgG as a secondary antibody. The blots are visualized by enhanced chemoluminescence using the SuperSignal peroxidase substrate (Pierce Chemical Co.). For quantification of sTRAIL using a sandwich ELISA, 96-well microtiter plates are coated with mouse anti-human TRAIL monoclonal antibody (BioSource) in 0.1M carbonate pH 9.6 buffer and incubated overnight at 4° C. The plates are washed extensively with PBS-0.05% Tween-20, and blocked with PBS-1% BSA-0.05% Tween-20 buffer for 1 hr.

Recombinant human TRAIL protein (RnD Systems, Minneapolis, Minn.) is used for standard curves after serial dilutions. Samples and the standard are incubated in the wells for 1 hr, washed extensively, and incubated with goat anti-human TRAIL polyclonal antibody (RnD Systems, Minneapolis, Minn.) for 1 hr. After extensive washing, the samples are incubated with HRP-conjugated anti-goat IgG antibody (Sigma Chemical Co.) for 1 hr, washed again, and then detected using Sure Blue TMB substrate (KPL, Gaithersburg, Md.) at 450/650 nm optical density. The following examples illustrate but are not intended in any way to limit the invention:

EXAMPLE 1

Construction of Recombinant AAV Vectors

AAV vectors are prepared according to Snyder et al., 1997, Nature Genetics 16(3):270–6. Briefly, subconfluent 293 cells are cotransfected with a vector plasmid and the helper plasmids pUC-ACG using the calcium phosphate method. Cells are infected with adenovirus Ad5 d1312 (an E1A-mutant) at an MOI of 2–5 and the infection is allowed to proceed for 72 hr. Cells are harvested and lysed by three freeze/thaw cycles. Lysates are treated with benzonase (Sigma) and then centrifuged to remove the cellular debris. The cleared cell lysate is fractionated by ammonium sulfate precipitation and the rAAV virions are isolated on two sequential CsCl gradients. The gradient fractions containing rAAV are dialyzed against sterile PBS containing 0.9 mM $CaCl_2$ and 0.5 mM $MgCl_2$, heated for 30 min at 56° C. to inactivate any residual adenovirus. Viral titers are determined by dot-blot analysis and represent DNAse resistant genome equivalents per ml. Vector preparations are typically $10^{12}$ vp/ml.

EXAMPLE 2

In Vivo Evaluation of Recombinant AAV-CD In Treatment of Subcutaneous U87 Human Glioma Tumors In one initial experiment, human U87 glioma tumor cells were implanted subcutaneously (s.c.) in mice and the mice were treated with three vectors expressing different types of cytosine deaminase (CD). Bacterial cytosine deaminase, yeast cytosine deaminase and a fusion gene encoding yeast cytosine deaminase and yeast uracil phoshoribosyl transferase (UPRT) were compared to an AAV vector encoding thymidine kinase. Mice were implanted with tumor cells on day 0. Seven days later, AAV vectors were injected directly into the tumor. On days 14–25 animals were given a treatment regimen with 5-flourocytosine (5-FC) at a dose of 500 mg/kg/day. Animals injected with AAV-TK were treated with gangcyclovir (100 mg/kg/day). Efficacy of AAV treatment was assessed by the rate of tumor growth over the course of the experiment.

TABLE 5

| | Tumor Type |
|---|---|
| Tumor Type | U87 human glioma |
| Source | Cultured cells grown under standard conditions |
| Preparation | Trypsinized, washed in media, spun down and resuspended in media at 50 million cells/ml and mixed with an equal vol. of matrigel ®. 0.2 ml are injected per mouse (5 × $10^6$ cells). 90 mice are injected with tumors but only 80 mice are used in a given study. |

TABLE 5-continued

Tumor Type

| | |
|---|---|
| Tumor Type | U87 human glioma |
| Hormonal | No hormones are required for this cell line |
| Extracellular matrix | Matrigel ® |

TABLE 6

Animals

| | |
|---|---|
| Identification | 101–810 |
| Species | Mice |
| Strain | NCR.nu/nu homozygous |
| Source | Taconic |
| Gender | Female |
| Total number | 90 mice |

TABLE 7

Active Agent(s) and Dosing Schedule

| Animal ID | n | Agent | Dose (μl) | 5-FC/GCV Regime Days 14–25 |
|---|---|---|---|---|
| 101-110 | 10 | rAAV-CAG-bCD | 50 | 5-FC 500 mg/kg/day IP |
| 201-210 | 10 | rAAV-CAG-yCD | 50 | 5-FC 500 mg/kg/day IP |
| 301-310 | 10 | rAAV-CAG-yCD::UPRT | 50 | 5-FC 500 mg/kg/day IP |
| 401-410 | 10 | rAAV-CAG-GFP | 50 | 5-FC 500 mg/kg/day IP |
| 501-510 | 10 | rAAV-CAG-bCD | 50 | none |
| 601-610 | 10 | rAAV-CAG-yCD::UPRT | 50 | none |
| 701-710 | 10 | rAAV-CAG-TK | 50 | GCV 100 mg/kg/day IP |
| 801-810 | 10 | rAAV-CAG-GFP | 50 | none |
| 901-908 | 8 | rAAV-CAG-TRAIL | 50 | none |

TABLE 8

Monitoring

| Parameter | Monitoring Frequency |
|---|---|
| Body weight/body condition | Twice weekly |
| Clinical Observations | Daily |
| Tumor Measurements | Twice weekly |

TABLE 9

Study Endpoints: Indications that animal should be euthanized.

| Parameter | Endpoint Values |
|---|---|
| Tumor Vol. | >2500 mm$^3$ - Euthanize immediately |
| Weight loss | 15% or greater - Euthanize immediately |
| Duration of study | Approximately 5–7 weeks |
| Harvest date | 6 months or earlier if tumor growth allows |
| Other parameters | None |
| Specific Behavioral Parameters | Limits on survivability |

Tumor volumes are calculated as 0.5×L×W×H. Tumor lag time is defined as time from inoculation to progressive tumor growth or the experiment day when two successive tumor measurements showed increased tumor volume. Tumor growth rate was calculated as the slope of tumor volume over time in days. CD+5-FC test groups were compared to each other and to CD−5-FC, TK+GCV and GFP test groups to determine efficacy. The results of an initial study are provided in Table 10.

TABLE 10

Tumor Volume (mm$^3$) After Treatment with AAV Vectors Encoding Cytotoxic or Pro-Apoptotic Genes.

| TREATMENT | Day 0 | Day 4 | Day 10 | Day 15 | Day 18 | Day 22 | Day 25 | Day 29 | Day 31 | Day 35 |
|---|---|---|---|---|---|---|---|---|---|---|
| 100 rAAV-CAG-bCD + 5-FC | 0 | 107.7 | 159.4 | 150 | 123 | 116.2 | 103.4 | 162.1 | 180.5 | 334.5 |
| 100 rAAV-CAG-bCD + 5-FC STDEV | 0 | | 44 | 44.2 | 45.8 | 46.6 | 73.2 | 180.83 | 213.9 | 424.4 |
| 200 rAAV-CAG-yCD + 5-FC | 0 | 84.6 | 151.8 | 121.4 | 119.8 | 98.8 | 89 | 97.5 | 121.06 | 176.9 |
| 200 rAAV-CAG-yCD + 5-FC STDEV | 0 | | 99.5 | 51.7 | 61.32 | 57 | 61.37 | 82.64 | 98.3 | 200.3 |
| 300 rAAV-CAG-yCD::UPRT + 5-FC | 0 | 76.5 | 140.7 | 124 | 118 | 86.505 | 66.8 | 67.6 | 62.12 | 76.22 |
| 300 rAAV-CAG-yCD::UPRT + 5-FC STDEV | 0 | | 42.7 | 34.1 | 36.3 | 36.4 | 37.6 | 45.25 | 38.6 | 59.23 |
| 400 rAAV-CAG-GFP + 5-FC | 0 | 87.5 | 135.3 | 136.2 | 139 | 112.91 | 139 | 199 | 235.2 | 414.1 |
| 400 rAAV-CAG-GFP + 5-FC STDEV | 0 | | 49.2 | 40.6 | 58.7 | 62.5 | 99.6 | 179.5 | 235.5 | 627.9 |
| 500 rAAV-CAG-bCD − 5-FC | 0 | 97.4 | 139.9 | 140.6 | 122.6 | 103.87 | 120.7 | 219.6 | 243.6 | 381.6 |
| 500 rAAV-CAG-bCD − 5-FC STDEV | 0 | | 48.8 | 33.8 | 36.31 | 46.42 | 72.7 | 203.1 | 272.2 | 471.3 |
| 600 rAAV-CAG-yCD::UPRT − 5-FC | 0 | 88.9 | 99.7 | 92.2 | 87.34 | 71.92 | 57.23 | 46.6 | 46.7 | 56.01 |
| 600 rAAV-CAG-yCD::UPRT − 5-FC STDEV | 0 | | 48.8 | 31.8 | 21.655 | 34.94 | 33.35 | 38.2 | 43.12 | 78.6 |
| 700 rAAV-CAG-TK + GCV | 0 | 85.7 | 121.8 | 145.5 | 105.6 | 75.15 | 57.018 | 56.4 | 41 | 49.5 |
| 700 rAAV-CAG-TK + GCV STDEV | 0 | | 42.1 | 49.7 | 24.8 | 21.47 | 14.52 | 17.9 | 17.404 | 33.96 |
| 800 rAAV-CAG-GFP − 5-FC | 0 | 93.1 | 136.6 | 143.5 | 144.8 | 117.8 | 140.87 | 162.2 | 183.1 | 377.7 |
| 800 rAAV-CAG-GFP − 5-FC STDEV | 0 | | 23.9 | 38.6 | 38.3 | 18.6 | 86.17 | 192.6 | 204.56 | 497.7 |
| 900 rAAV-CAG-TRAIL | 0 | 70.2 | 135.7 | 154.3 | 142.35 | 99 | 105.6 | 118.02 | 137.47 | 234 |
| 900 rAAV-CAG-TRAIL STDEV | 0 | | 43.3 | 39.5 | 59.3 | 58 | 96 | 121.3 | 158.66 | 268.3 |

EXAMPLE 3

In Vivo Evaluation of Recombinant AAV Encoded Platelet Factor in the Treatment of Subcutaneous U87 Human Glioma A subcutaneous human U87 glioma tumor model was used for evaluation of the effect of direct intra-tumoral injection of AAV-6 encoded PF-4 and PF-4(DLR). In a typical experiment, on Days 0—mice are injected with U87 tumors. On Day 7 post-injection, animals were selected based on tumor size and tumors injected directly with AAV-6 vectors encoding PF-4 and PF-4(DLR). The nucleic acid sequnce encoding PF-4 and PF-4(DLR) are presented as SEQ ID NO:6 and SEQ ID NO:6, respectively. Efficacy of PF-4 and PF-4(DLR) by AAV mediated gene delivery was assessed by the rate of tumor growth over the course of the experiment in comparison to a pAAV-null injected control group. The U87 glioma tumor model relies on U87 human glioma cells cultured under standard conditions, cells/ml, then mixed with an equal vol. of Matrigel®. 0.2 ml are injected into each mouse (5×106 cells/mouse). In one exemplary study female NCR.nu/nu homozygous mice (Taconic) were dosed intratumorally (IT) with 2×10e11 viral genomes of rAAV-CAG-PF-4, rAAV-CAG-PF-4(DLR) or rAAV-EF1a-Null. Studies are typically carried out for 7 to 10 weeks and mice are monitored by daily observation (following tumor implantation), twice weekly tumor measurements are taken and body weight/body conditions evaluated. Studies are typically terminated 3 months or earlier if possible. The study endpoints include tumor volume and weight loss with mice immediately euthanized if tumor volume exceeds 2000 mm$^3$ or weight loss is 15% or greater. rAAV plasmids expressing platelet factor-4 (PF-4) and PF-4 with the DLR mutation were constructed.

Figure 2:
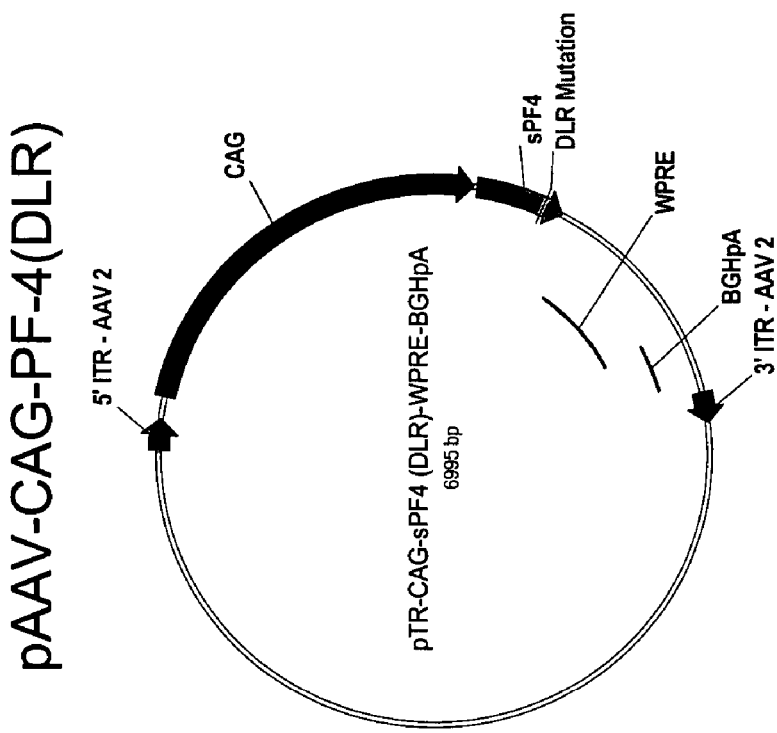
FIG. 2 is a schematic depiction of an AAV plasmid vector that expresses the human platelet factor-4 gene containing the DLR mutation from the CAG promoter. The PF-4 coding region is adjacent to the woodchuck post-transcriptional regulatory element (WPRE) and bovine growth hormone polyadenylation sequence (BGHpA). The PF-4 expression cassette is flanked on either side by the AAV-2 ITR sequences.
Figure 3:
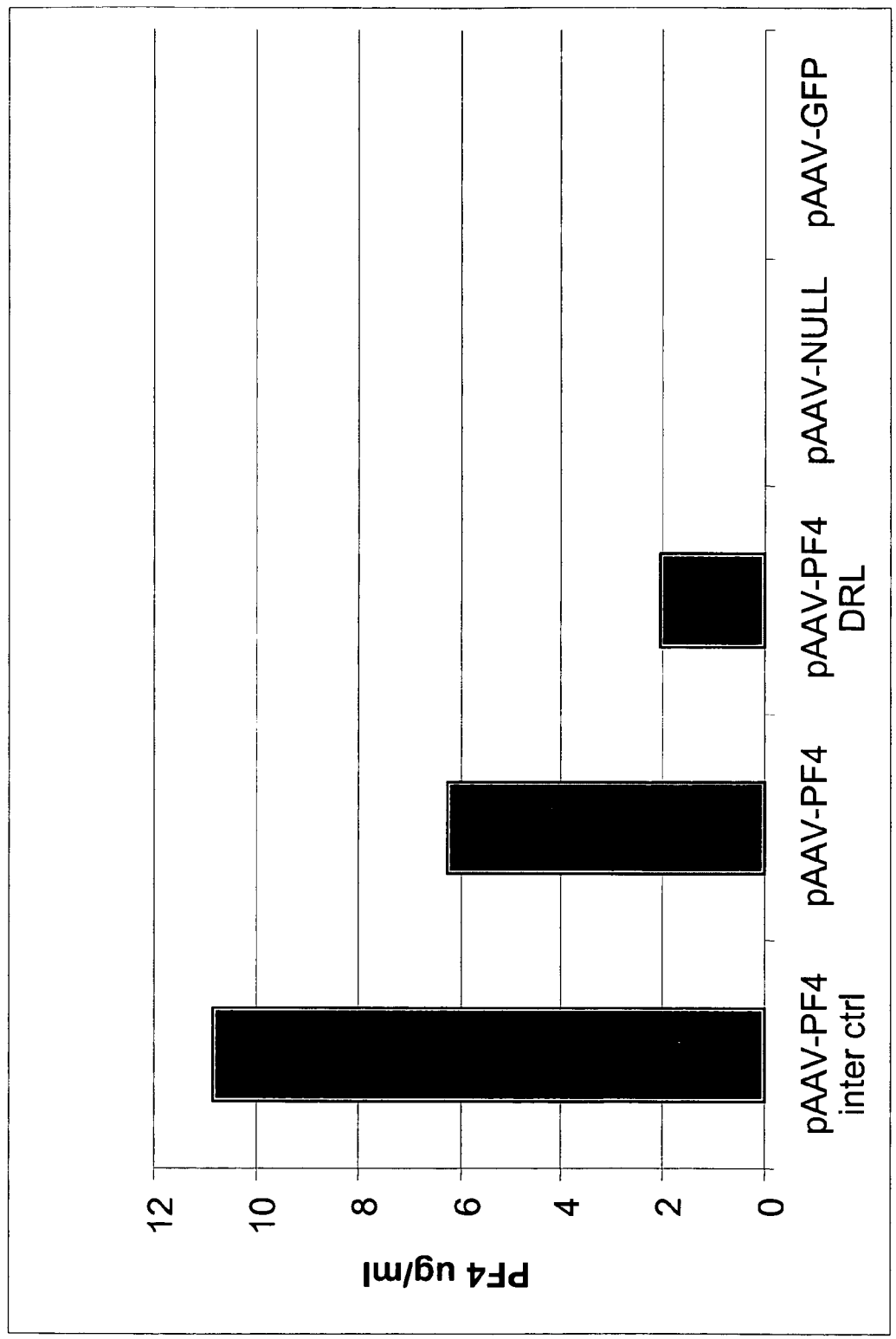
FIG. 3 illustrates the results of an ELISA for PF-4 following the transfection of 293 cells with AAV vector plasmids encoding PF-4 or PF-4 (DLR). 293 cells in 5% FBS/DMEM were transfected using FuGene 6 with the appropriate vector constructs and 48 hours post-transfection PF-4 levels determined by PF-4 ELISA following 1:100 dilution of supernatants. Levels of PF-4 expression were compared against an internal pAAV-PF-4 control supernatant, in addition to pAAV-Null and pAAV-GFP vector constructs.
Figure 4:
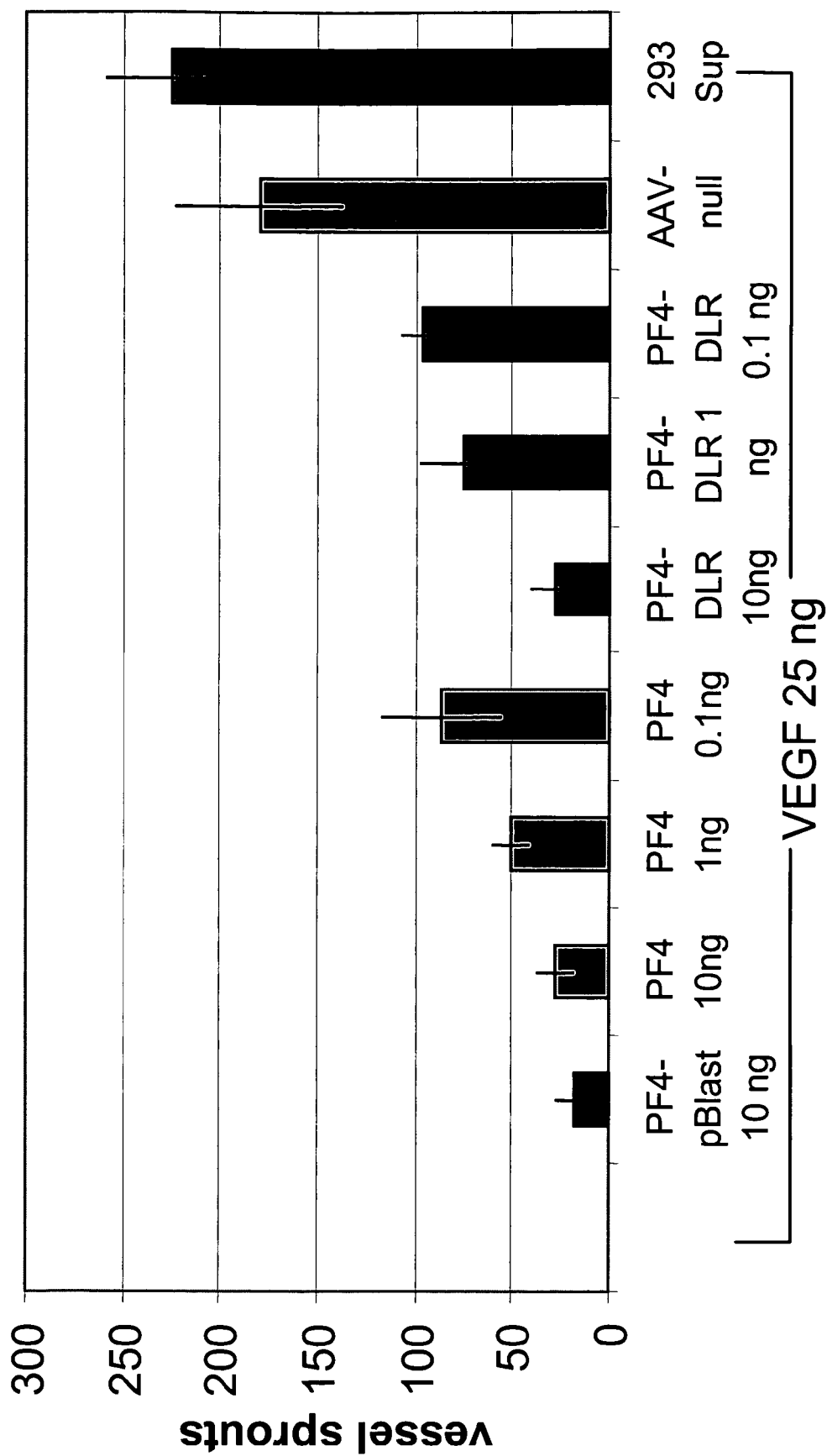
FIG. 4 illustrates the results of experiments that show PF4 and PF4(DLR) reduce VEGF stimulated angiogenesis in the chick chorioallantoic membrane (CAM) assay. Hyrdocortisone-containing filter disks were soaked with 25 ng of VEGF together with 0.1 ng, 1 ng and 10 ng of PF-4 or PF-4(DLR) derived from conditioned media. AAV-null, 293 cell supernatant and an internal PF-4 protein standard, PF4-Blast, were included in the assay as separate controls. Filter disks were aseptically placed on top of the chorioallantoic membranes of 11 day chick embryos. 72 hours after incubation the CAMs were surgically removed, fixed and the number of vessel sprouts determined by stereomicroscopy.

Briefly, base pair 2197 of pBLAST-sPF4 (Invivogen, San Diego, Calif.) was mutated from A to G using the QuickChange Site-Directed Mutagenesis Kit (Stratagene, La Jolla, Calif.) to create the plasmid pBLAST-sPF4(DLR). Primers used were sPF4(DLR) Forward (SEQ ID NO:10) and sPF4 (DLR) Reverse (SEQ ID NO:11). Sequences were confirmed using the ABI Prism 3100-Avant Genetic Analyzer (Applied Biosystems, Foster City, Calif.). pBLAST-sPF-4 and pBLAST-sPF4(DLR) were then digested with Pvu II and Nhe I and the resulting 363 bp fragments isolated using QIAquick Gel Extraction Kit (Qiagen, Hilden, Germany) and blunted using T4 DNA Polymerase (Invitrogen Corp., Carlsbad, Calif.). Fragments were then separately ligated into our pTR-CAG-Polyclone-WPRE-BGHpA backbone that had been Stu I digested using the Rapid DNA Ligation Kit (Roche Pharmaceuticals, Basel, Switzerland). This created the plasmid constructs pTR-CAG-sPF-4-WPRE-BGHpA and pTR-CAG-sPF-4 (DLR)-WPRE-BGHpA, respectively (FIG. 2). To confirm expression of PF-4 and PF-4(DLR), pTR-CAG-sPF-4-WPRE-BGHpA and pTR-CAG-sPF-4 (DLR)-WPRE-BGHpA were transfected using Fugene 6 into 293 cells and PF-4 expression verified in the cell supernatant using ELISA (FIG. 3). In addition, the anti-angiogenic properties of PF-4 and PF-4(DLR) were demonstrated in the chick CAM model by blockage of VEGF induced vessel sprouting at different concentrations of the inhibitors (FIG. 4). AAV-6 vectors encoding PF-4 (DLR) were prepared and purified according to Snyder et al., 1997, Nature Genetics 16(3):270–6 using the AAV-6 packaging plasmid pRepCap6 (Halbert Cl et al., 2000, Journal of Virology 74(3):1524–32).

In one study, the murine subcutaneous human U87 glioma tumor model was used for evaluation of the effect of direct intra-tumoral injection of 3×1011 AAV-6 encoded PF-4 (DLR); rRAAV6-CAG-PF-4(DLR) or rAAV-KONG vector genomes. On Day 0, mice were implanted with s.c. human U87 tumors. On Days 7, 14 and 21 following U87 tumor cell injection, animals were directly injected intra-tumorallly with AAV-6 vectors encoding PF-4(DLR) or a control vector that expresses no transgene.

Figure 5:
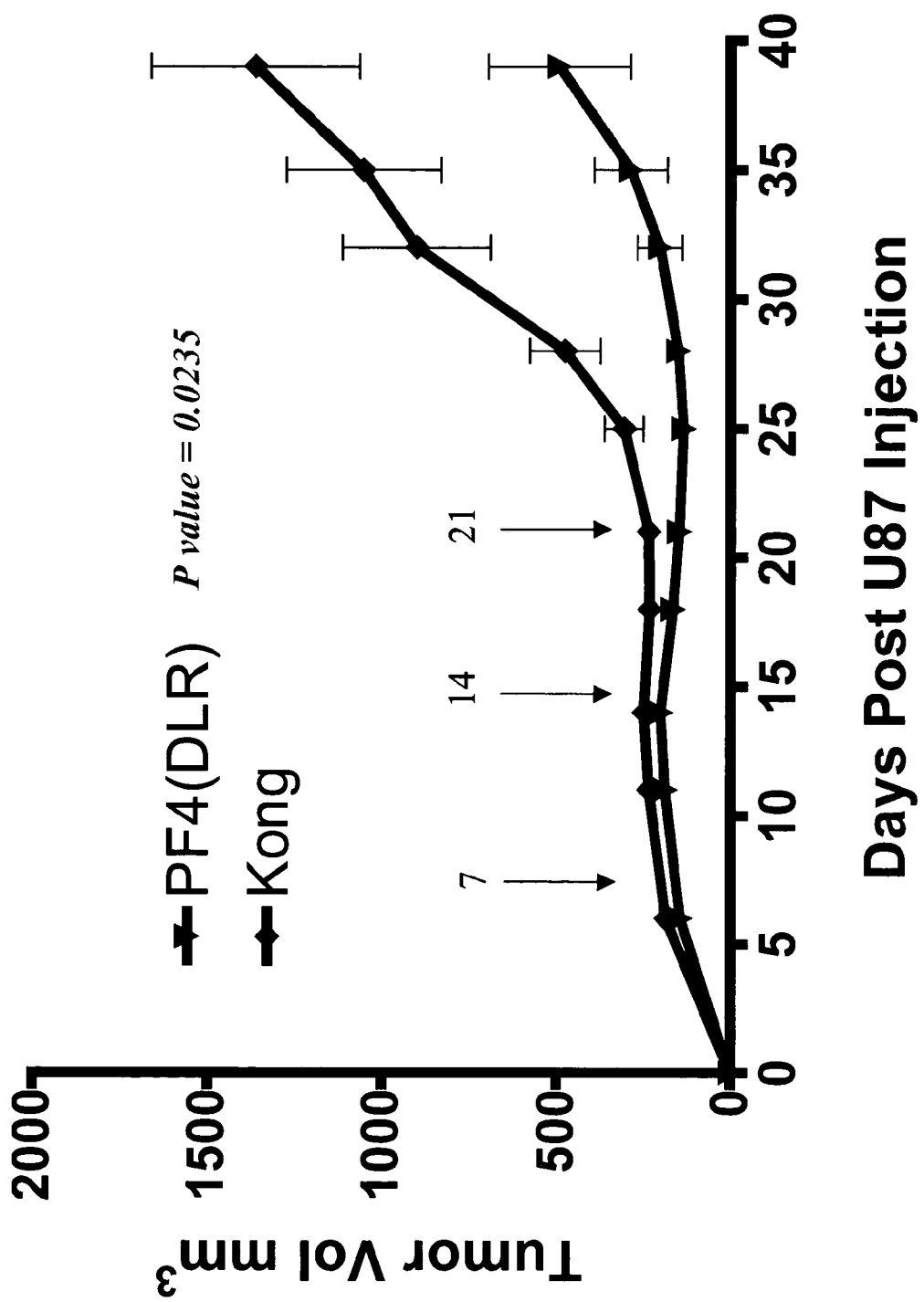
FIG. 5 shows that AAV-mediated PF-4 (DLR) expression reduces U87 sub-cutaneous (s.c.) tumor growth following intratumoral injection. NCRnu.nu mice were sub-cutaneously (s.c.) implanted with U87 tumors on day 0. On days 7, 14 and 21 post-implantation, 1×10e11 vector genomes of AAV serotype 6 vector encoding PF-4(DLR) or a null (KONG) control were administered directly to the tumor by means of a minipump as indicated in the figure by arrows. Following vector administration, tumor size was evaluated for 40 days. Error bars represent +/−SEM. Solid line with triangle symbols: AAV-CAG-PF4(DLR) injected, solid line with diamonds: AAV-KONG (null) control injected.
Figure 6:
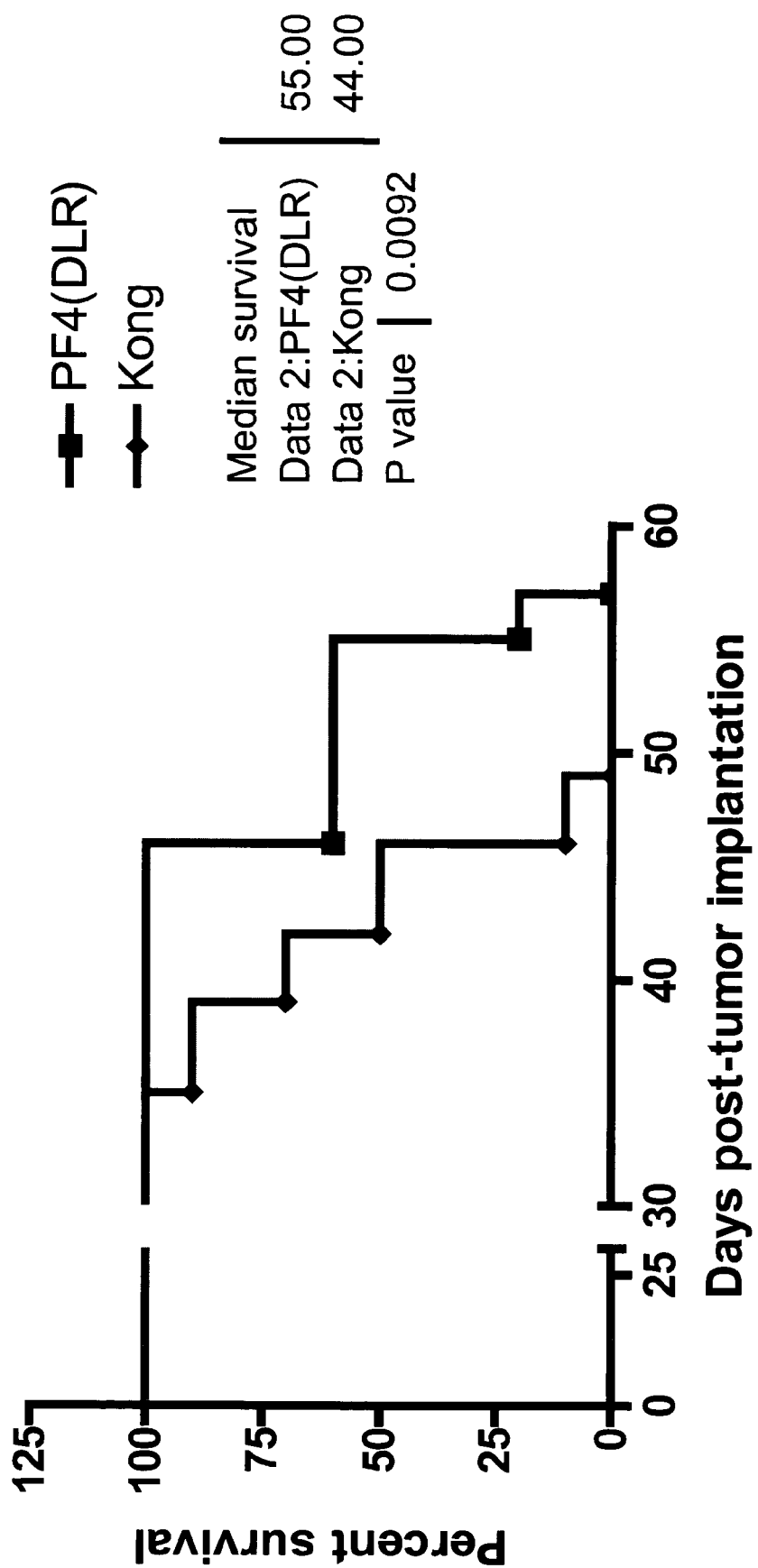
FIG. 6 shows that AAV-mediated PF-4 (DLR) expression improves survival in the U87 sub-cutaneous (s.c.) tumor model following intratumoral injection. NCRnu.nu mice were sub-cutaneously implanted with U87 tumors on day 0. On days 7, 14 and 21 post-implantation, 1×10e10 vector genomes of AAV serotype 6 vector encoding PF-4(DLR) or a null (KONG) control were administered directly to the tumor by means of a minipump. Following vector administration animal survival was assessed up to 60 days. Solid line with square symbols: AAV-CAG-PF4(DLR) injected, solid line with diamonds: AAV-KONG (null) control injected.

Tumor volumes are calculated as 0.5×L×W×H. Tumor lag time is defined as time from inoculation to progressive tumor growth or the experiment day when two successive tumor measurements showed increased tumor volume. Efficacy of PF-4(DLR) by AAV mediated gene delivery was assessed by the rate of tumor growth over the course of the experiment in comparison to a Null injected control group (FIG. 5). The decrease in U87 tumor growth also correlated with a significant survival advantage to the animals as assessed from Kaplan Meier curves (FIG. 6).

EXAMPLE 4

Biochemical and Biological Anti-tumor Activity of AAV produced TRAIL

An expression plasmid encoding full-length (amino-acids 1–281; SEQ ID NO:2) membrane bound human TRAIL (SEQ ID NO:1), pORF-hTRAIL, was purchased from Invivogen (San Diego, Calif.). An isoluecine zipper modified variant soluble version of human TRAIL (LZsTRAIL; SEQ ID NO:4) was constructed by placing a tPA signal sequence (Invivogen) and a modified isoleucine zipper motif, MKQIEDKIEEILSKIYHIENEIARIKKLIGERE (SEQ ID NO:5; Harbury et al 1993, Science 262:1401–1407; Wu et al 2001 Molecular Therapy 3:368–374) in-frame to the extracellular portion (amino-acids 114–281) of human TRAIL (FIG. 7B) and cloned into the pORF expression plasmid (Invivogen).). The nucleic acid sequnce encoding LZsTRAIL is presented as SEQ ID NO:3.

Figure 8B:
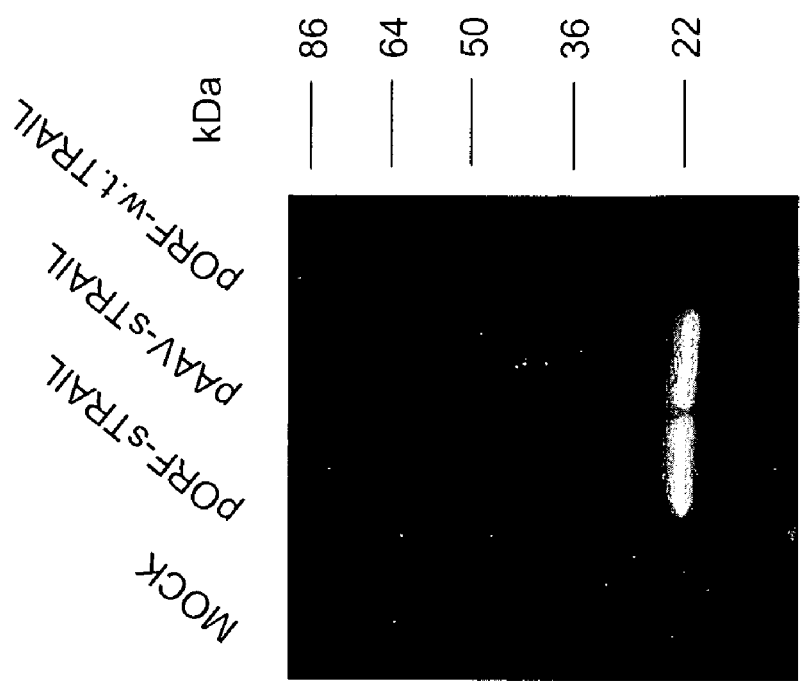
Figure 8A:
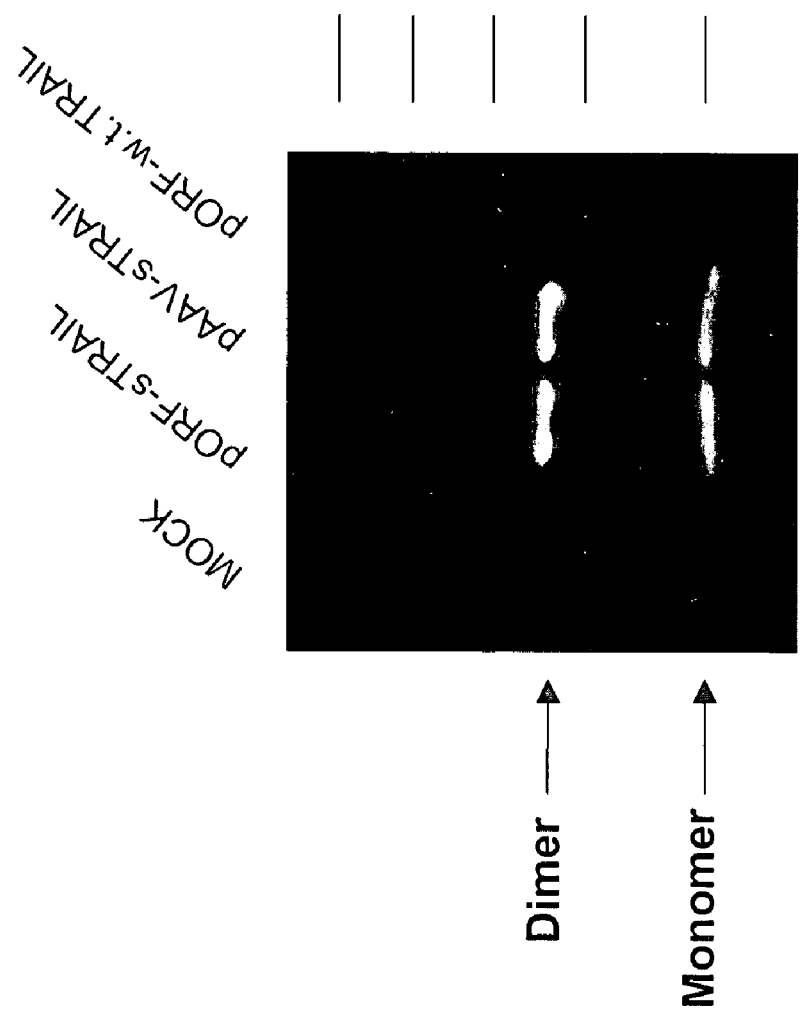
FIGS. 8A and B illustrate detection of soluble TRAIL by Western immunoblotting analysis.
Figure 9:
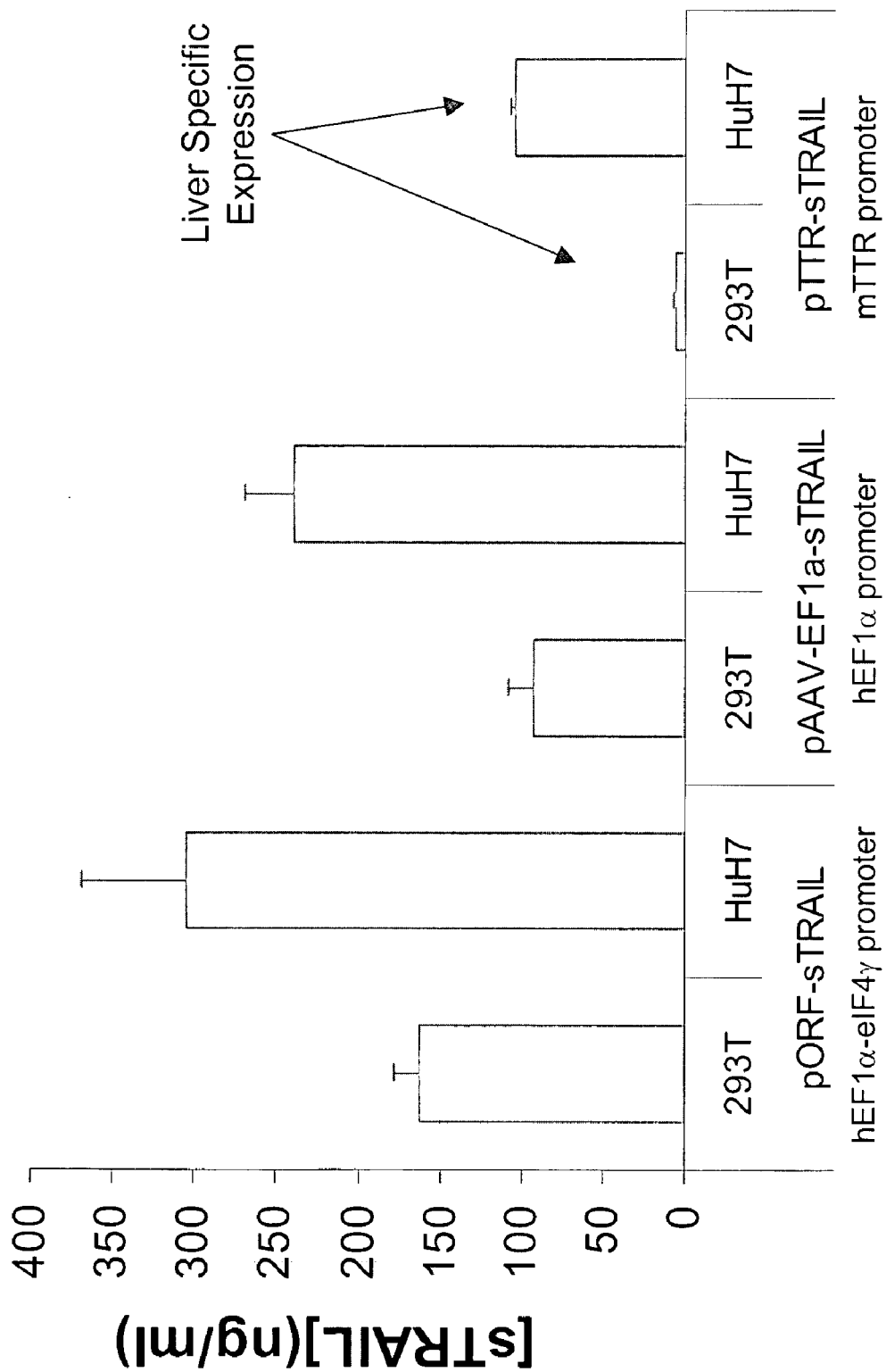
FIG. 9 illustrates expression of sTRAIL from expression constructs driving the transgene from different promoters including a human elongation factor 1-alpha/eIF4 alpha initiation factor hybrid promoter (EF1 alpha-eIF4 alpha), the human elongation factor 1-alpha (EF1 alpha) promoter, or the liver-specific mouse transthyretin (mTTR) promoter. Human 293 embryonic kidney cells or HuH7 hepatocytes were transiently transfected with the indicated expression plasmids encoding sTRAIL. Conditioned media was collected 48 hr later and assayed for sTRAIL expression using a sandwich ELISA.

Both membrane-bound and soluble TRAIL constructs were further cloned into AAV2 expression plasmids under the control of the human EF-1 alpha, CAG or mouse transthyretin (mTTR) promoters. To verify expression of TRAIL from these constructs, 293 cells were transiently transfected with TRAIL expression plasmids and conditioned media was harvested after 48 hr. As shown in FIGS. 8A and 8B, monomeric and dimeric forms of soluble TRAIL were detected in the conditioned media of cells transfected with sTRAIL expression plasmids, but not from cells that were MOCK transfected or transfected with membrane-bound TRAIL plasmids. To quantitate the expression of soluble TRAIL, AAV or pORF expression plasmids encoding soluble TRAIL under the expression of different promoters were transiently transfected in 293 or HuH7 for 48 hr. As shown in FIG. 9, modest amounts of soluble TRAIL was detected in the conditioned medium of transfected 293 and HuH7 cells. Moreover, liver-specific expression of sTRAIL was detected in HuH7 hepatocytes compared to 293 kidney cells when soluble TRAIL was expressed under the control of the mTTR liver-specific promoter (FIG. 9).

Figure 11C:
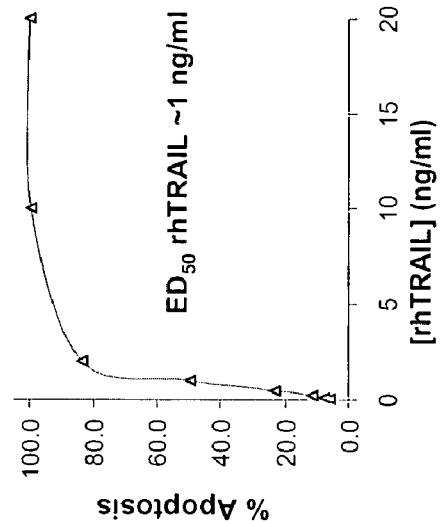
FIGS. 11A–D illustrate time and dose-dependent induction of DNA fragmentation/apoptosis in Colo-205 cells by sTRAIL, wherein apoptosis is measured by cytoplasmic histone-associated nucleosomes (DNA Fragmentation) by ELISA. % Apoptosis=[O.D. Treated−background]/[Maximal O.D.
Figure 11D:
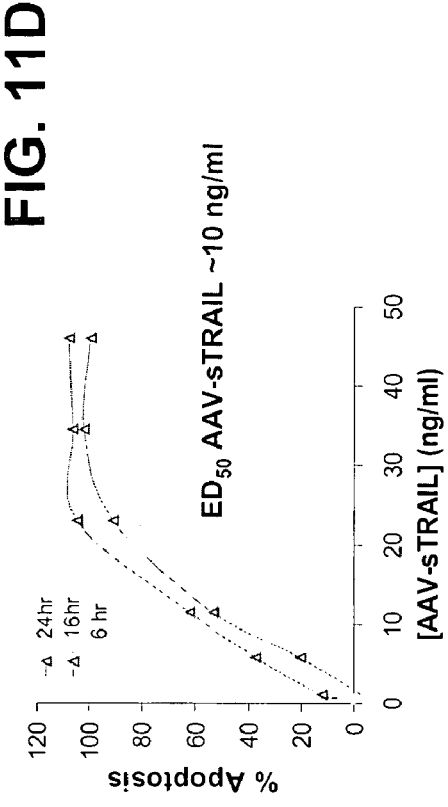
Figure 11A:
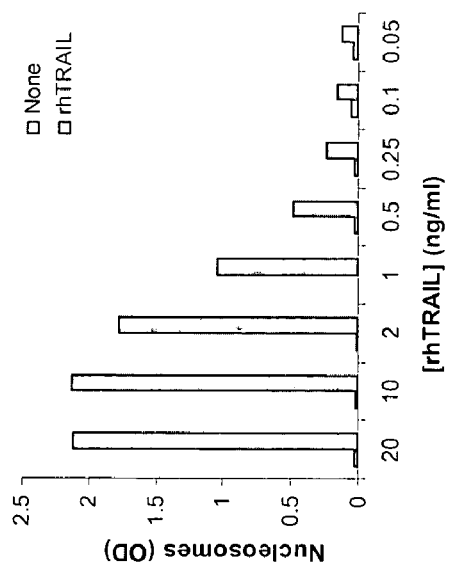
Figure 11B:
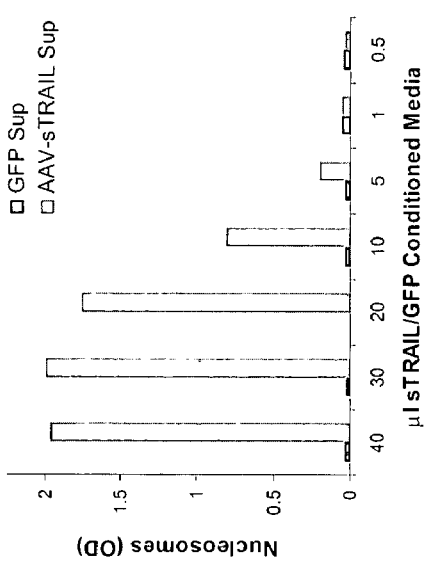
Figures 12A, 12B:
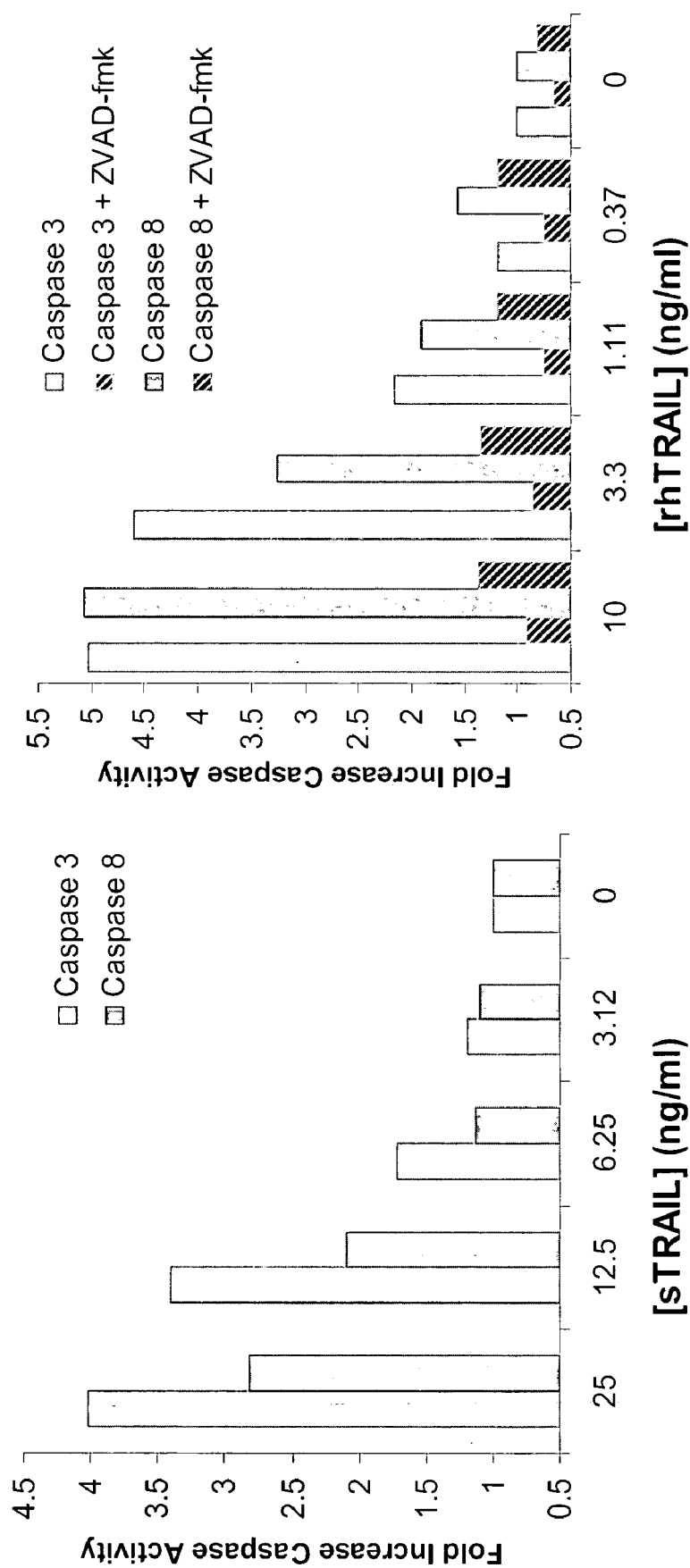
FIGS. 12A and B illustrate dose-dependent induction of caspase protease activity in Colo-205 cells following incubation with sTRAIL, where caspase protease activity is quantitated spectrophotometrically from 4 hr sTRAIL treated cell lysates using chromogenic bound Caspase 3 (DEVD-pNA) and Caspase 8 (IETD-pNA). Substrates and cells pre-incubated with (20 mM) pan-Caspase inhibitor, ZVAD-fmk, showed blocking of TRAIL-induced caspase protease activity.
FIG. 12B shows that dose-dependent induction of Caspase-3 or Caspase-8 activity by recombinant TRAIL can be blocked by pre-incubating the cells with 20 uM pan-caspase inhibitor, zVAD-fmk.
Figure 13B:
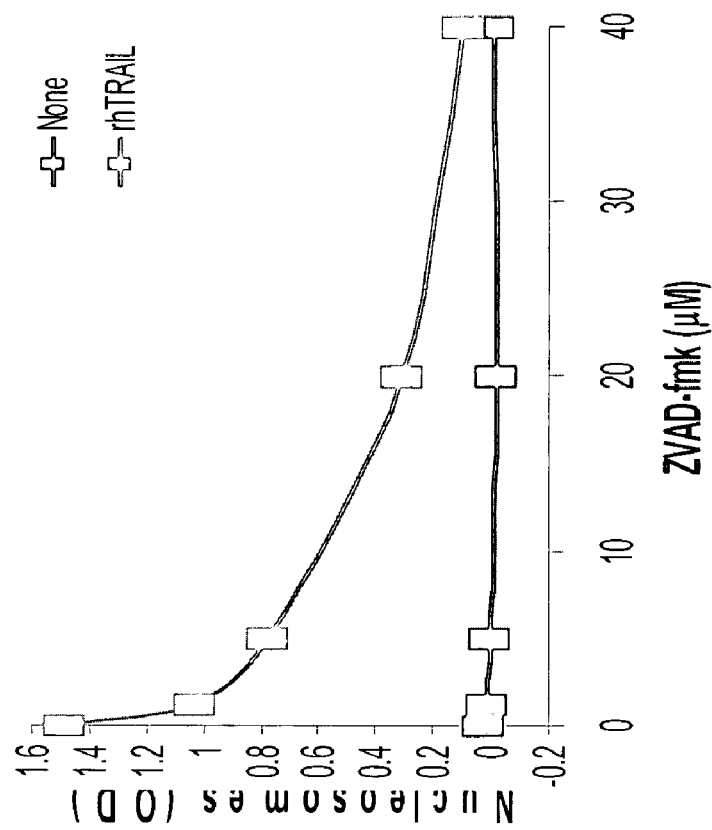
FIG. 13B illustrates that the induction of DNA fragmentation in Colo-205 cells by recombinant TRAIL, can be specifically inhibited by pre-incubating the cells with increasing amounts of the pan-caspase inhibitor, ZVAD-fmk. Apoptosis, e.g. DNA fragmentation, was measured by histone-associated nucleosome (DNA Fragmentation) ELISA 6 hr after sTRAIL treatment.
Figure 13A:
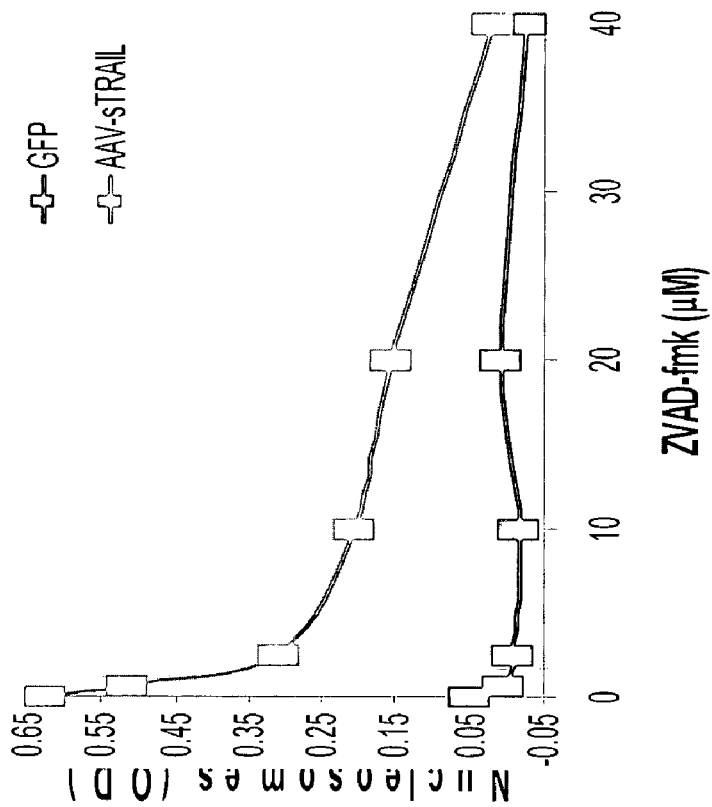
FIGS. 13A and B show that sTRAIL induces apoptosis in Colo-205 Cells in a caspase-dependent manner, as indicated by an experiment where pre-incubation of Colo-205 cells with the pan-Caspase inhibitor, ZVAD-fmk, prevents sTRAIL induced DNA fragmentation in a dose-dependent manner.

The biological activity of sTRAIL-induced cytotoxicity was verified in human Colo-205 tumor cells in vitro. As shown in FIGS. 10A and 10C, dose-dependent inhibition of Colo-205 cell viability was observed following treatment with conditioned media containing AAV-produced sTRAIL after 24, 48 and 72 hr. The 50% effective dose of Colo-205 growth inhibition by AAV-produced sTRAIL was approximately 5 ng/ml (FIG. 10C). The 50% effective dose of Colo-205 growth inhibition by recombinant human TRAIL purchased from a commercial vendor (RnD Systems) was approximately 0.5 ng/ml (FIG. 10B). To demonstrate sTRAIL-induced apoptosis, DNA fragmentation in Colo2-5 cells was quantitated following treatment with recombinant human TRAIL and AAV-produced sTRAIL (FIG. 11). Dose-dependent induction of DNA fragmentation was observed in Colo-205 cells that were treated with recombinant human TRAIL protein, but not in untreated cells, with a 50% effective dose (ED50) of approximately 1 ng/ml (FIGS. 11A and 11C). Similarly, Dose-dependent induction of apoptosis (DNA fragmentation) was observed in Colo-205 cells that were treated with AAV-produced sTRAIL, but not in control-treated cells, with a 50% effective dose (ED50) of approximately 10 ng/ml (FIGS. 11B and 11D). To demonstrate that the apoptosis-induction by sTRAIL was mediated by caspases, lysates from treated or untreated Colo-205 cells were measured for caspase 3 or caspase 8 enzymatic protease activity (FIG. 12). Dose-dependent induction of caspase 3 and caspase 8 protease activity was observed in Colo-205 cells that were treated with AAV-produced sTRAIL (FIG. 12A) or recombinant human TRAIL protein (FIG. 12B) with similar kinetics. The induction of TRAIL-induced caspase and DNA fragmentation activity could be blocked by pre-incubating the cells with a pan-caspase inhibitor, ZVAD-fmk (FIG. 12B), indicating that sTRAIL specifically mediates its activity via caspase mediated apoptosis (FIGS. 12 and 13).

Figure 14:
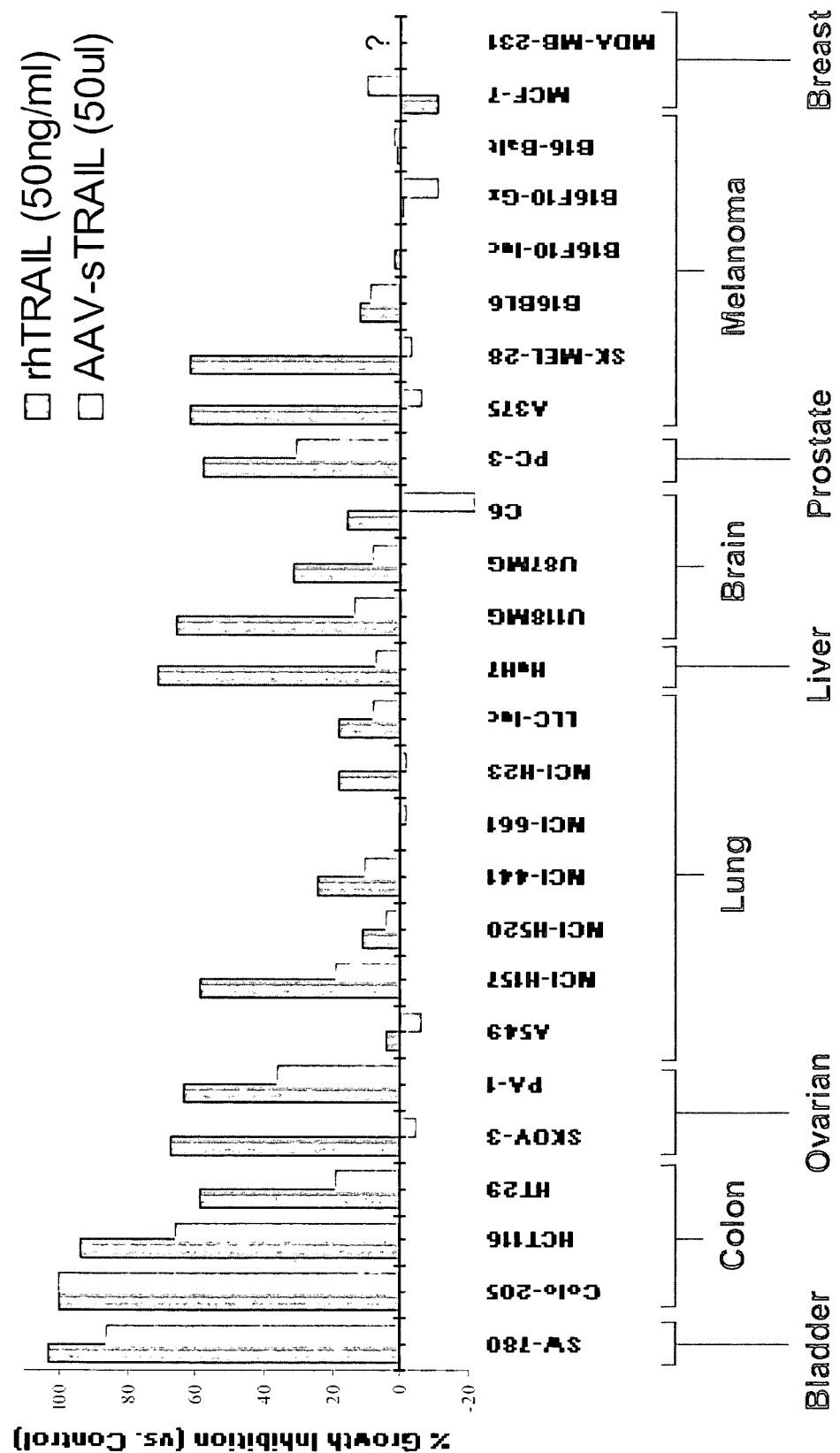
FIG. 14 shows the sensitivity of tumor cell lines to sTRAIL induced apoptosis. 1 e4 tumor cells cultured in 96 well plates were treated with AAV-produced sTRAIL or recombinant human TRAIL for 24 hr and cell viability was measured using a WST-8-based tetrazolium cytotoxicity assay. % Growth inhibition is defined as [1-(OD treated–background)/(OD untreated–background)×100.
Figure 15:
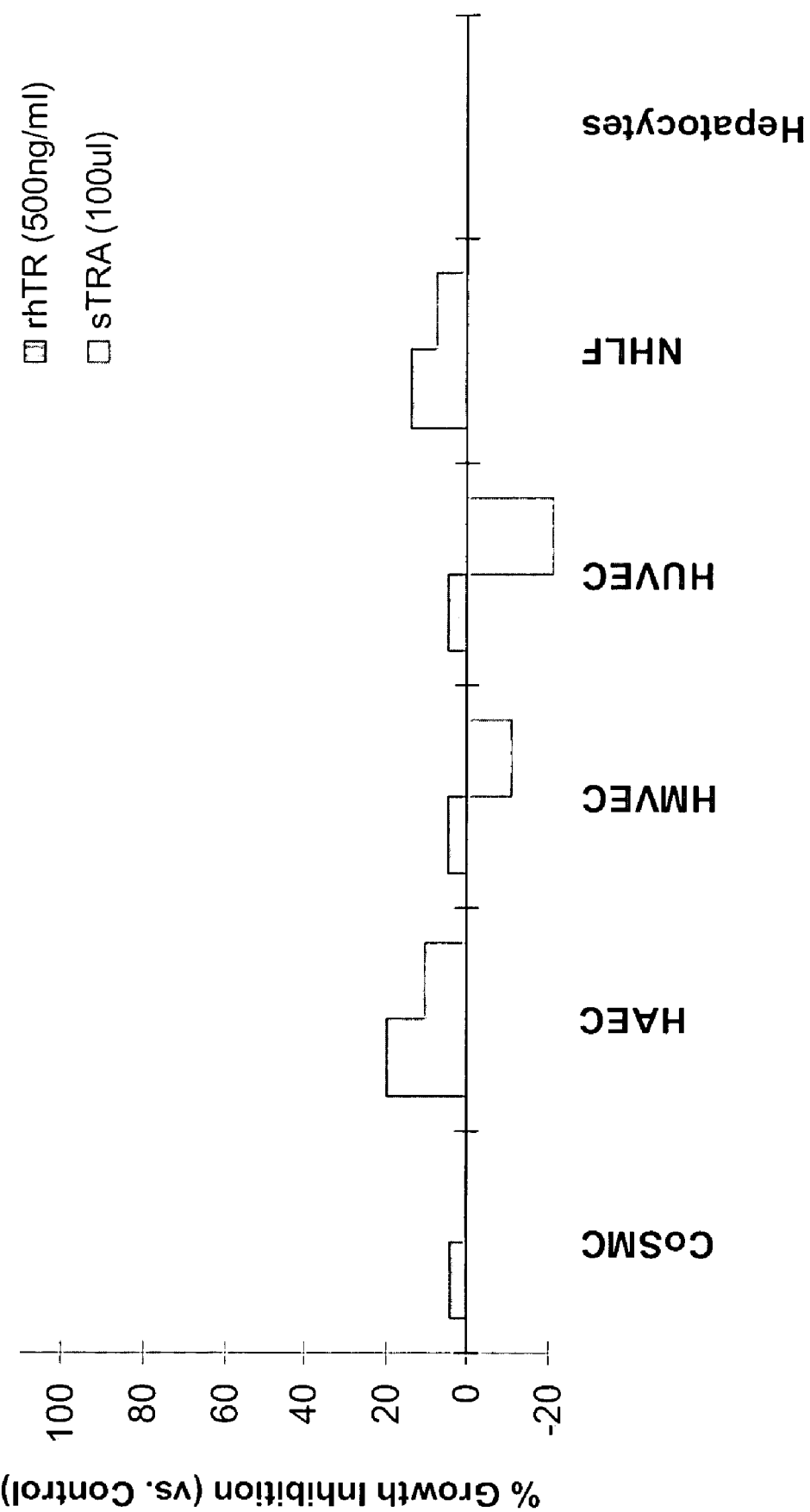
FIG. 15 shows that normal human primary cells are relatively insensitive to sTRAIL mediated cytotoxicity, as indicated by the effect of sTRAIL on CoSMC: Colo Smooth Muscle Cells; HAEC: human aortic endothelial cells; HMVEC: human microvascular endothelial cells; HUVEC: human umbilical vein endothelial cells; and NHLF: normal human lung fibroblast cells.
Figure 17C:
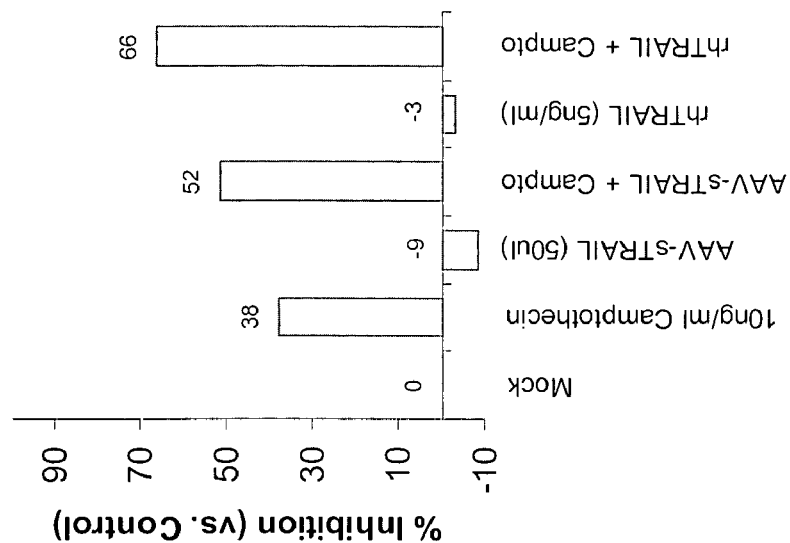
FIGS. 17A–C show augmentation of sTRAIL-induced HT29 colon cancer cytotoxicity by chemotherapy sensitization.
Figure 17B:
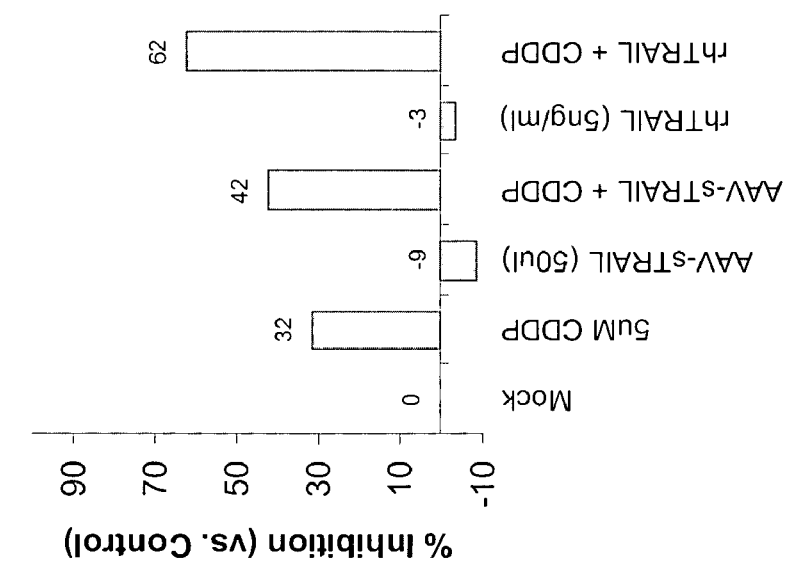
Figure 17A:
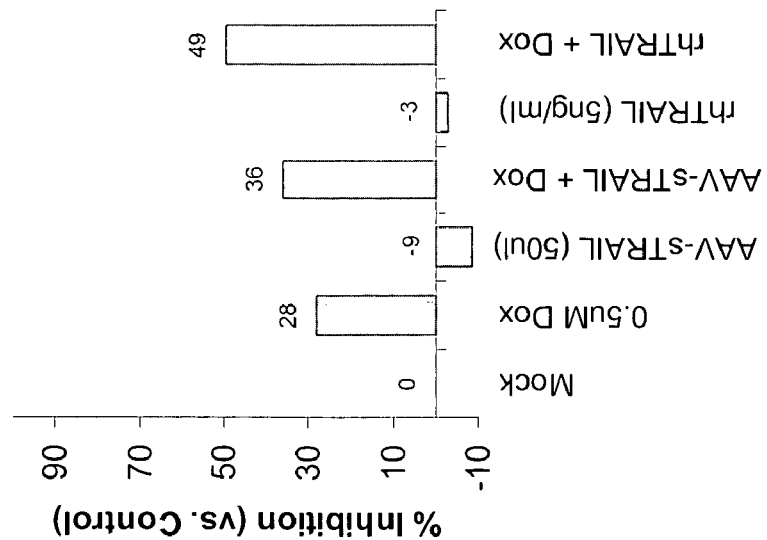
Figure 18C:
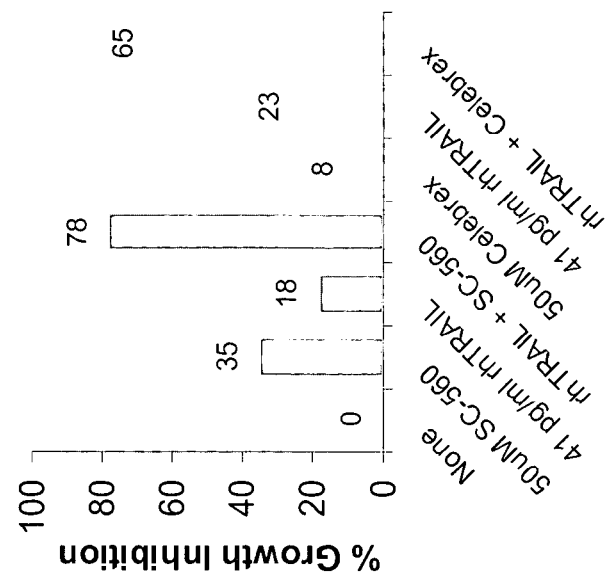
Figure 18B:
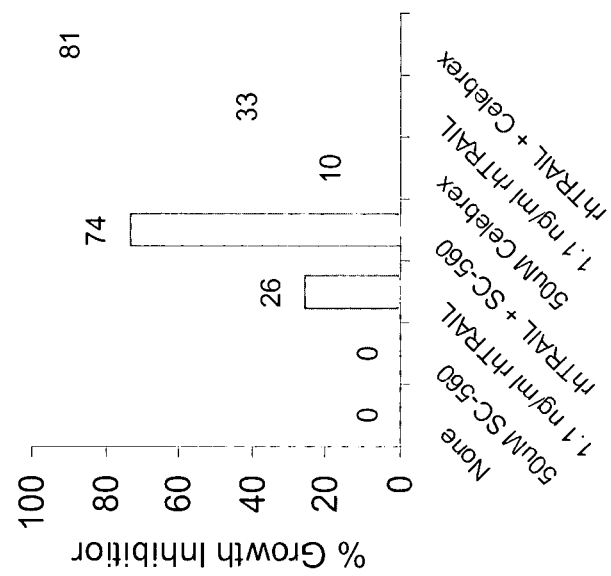
Figure 18A:
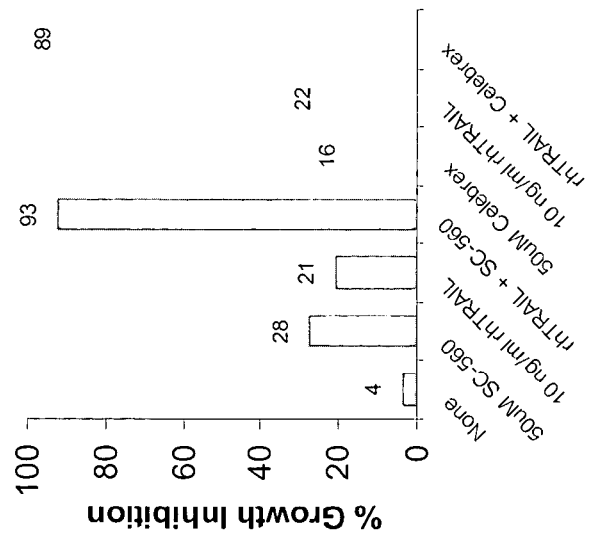

The specificity of TRAIL-induced cell death was tested in a variety of tumor and normal cells. As shown in FIG. 14, cytotoxicity was observed in a wide spectrum of human tumor cell lines from diverse tissues after treatment with recombinant human TRAIL or AAV-produced sTRAIL. In contrast, sTRAIL does not appear to induce cytotoxicity in normal human primary cells such as HAEC, HMVEC, HUVEC, NHLF, or CoSMC (FIG. 15). The combinatorial cytotoxic effects of TRAIL and chemotherapy were tested in a panel of tumor cells. As shown in FIGS. 16A–16D, a variety of tumor cell lines (A549 lung carcinoma, U87MG glioma, MCF7 breast carcinoma, PC-3 prostate carcinoma), when pre-treated with sub-toxic doses of anti-neoplastic agents (doxorubicin, etoposide, cisplatin), had an augmented cytotoxic effect when combined with treatment with AAV-produced sTRAIL or with recombinant human TRAIL protein. HT29 colorectal tumor cells appear to be refractory to cell death when treated at sub-optimal doses of TRAIL (FIG. 17). However, there was a synergistic cytotoxic effect when TRAIL was combined with sub-toxic doses of doxorubicin (FIG. 17A), cisplatin (FIG. 17B), or camptothecin (FIG. 17C) in HT29 colorectal tumor cells. In addition, synergistic cytotoxic activity was also demonstrated when TRAIL was combined with high doses of anti-inflammatory agents such as the cyclo-oxygenase-2 inhibitors, SC-560 and Celebrex in a panel of colorectal tumor cell lines (FIG. 18A–18C).

EXAMPLE 5

Anti-Glioma Activity of AAV-TRAIL Gene Transfer

Figure 20:
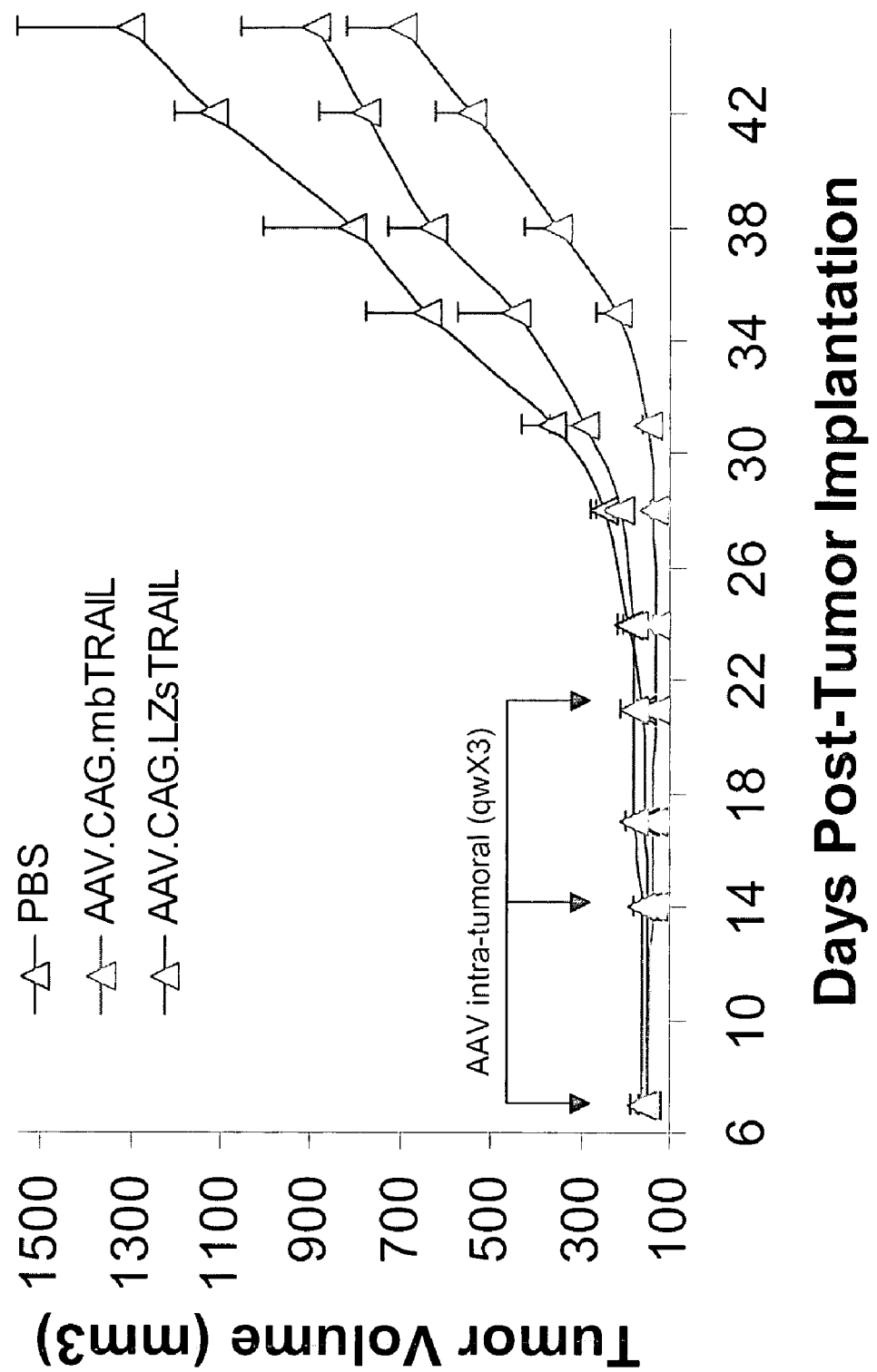
FIG. 20 shows that AAV-TRAIL gene therapy delays growth of human U87 glioma tumors in vivo. Immunodeficient mice bearing pre-established U87MG s.c. tumors were injected intratumorally (IT) with 2e5 or 5e10 vp of recombinant AAV-2 vectors encoding membrane-bound human TRAIL (mbTRAIL) or soluble TRAIL (LZsTRAIL). Tumor volume was monitored over time, as illustrated in the figure.
Figure 21:
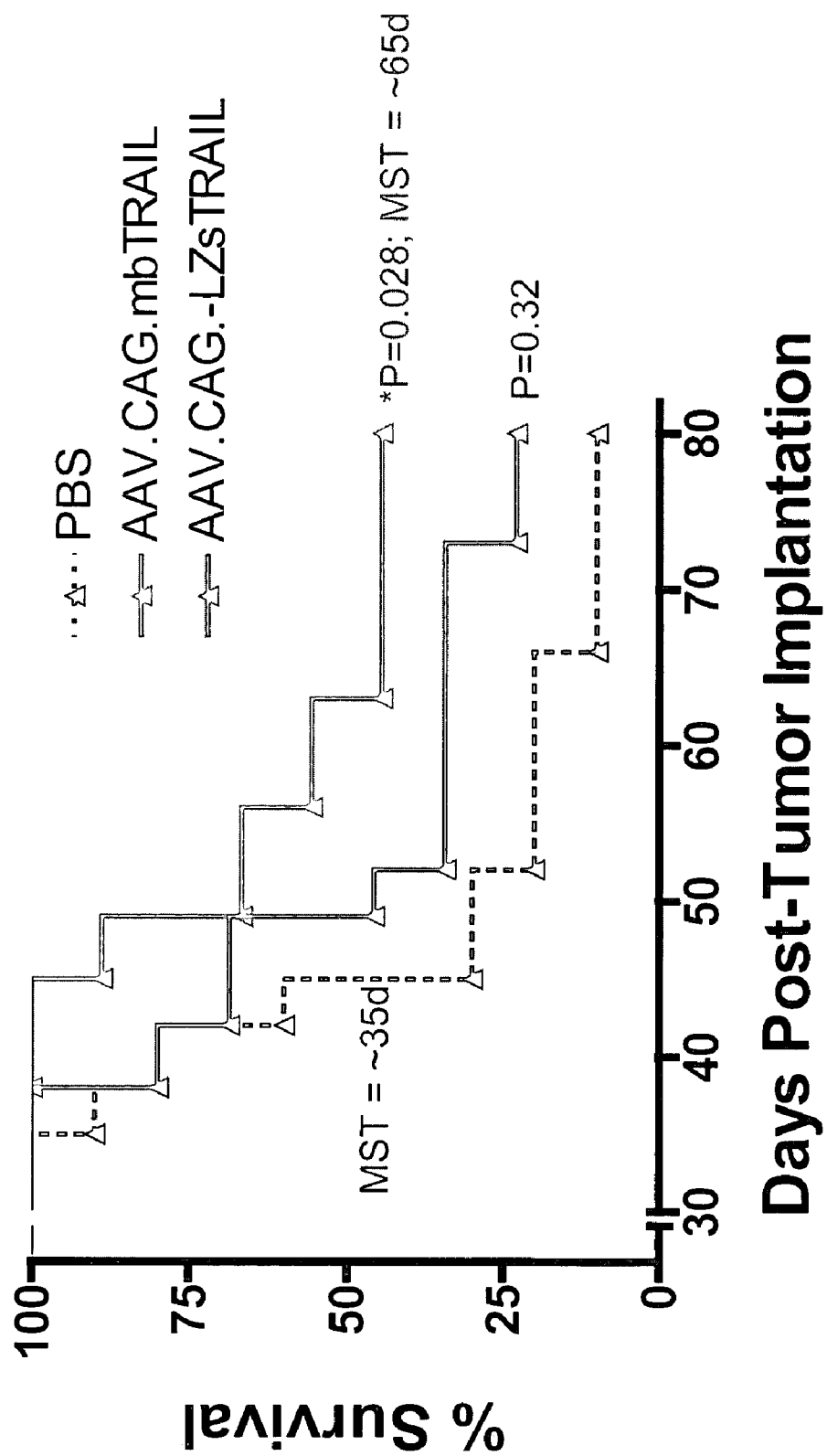
FIG. 21 shows that AAV-TRAIL increases survival of (U87MG glioma) tumor-bearing mice Immunodeficient mice bearing pre-established U87MG s.c. tumors were injected intra-tumorally (IT) with 2e5 or 5e10 vp of recombinant AAV-2 vectors encoding membrane-bound human TRAIL (mbTRAIL) or soluble TRAIL (LZsTRAIL). Mice were sacrificed when tumors became necrotic or reached a maximal volume of 1500 $mm^3$. Kaplan Meier survival curves is shown.

To verify the anti-glioma activity of TRAIL, recombinant AAV vectors encoding membrane-bound human TRAIL and soluble TRAIL whose expression was controlled under the CAG promoter were generated. As shown in FIG. 19A–19D, dose-dependent cytotoxicity of human T98G (FIG. 19A), human LN18 (FIG. 19B), human U87MG (FIG. 19C) and human U138MG (FIG. 19D) glioma tumor cell lines were observed following infection with increasing amounts of recombinant AAV2 vectors encoding membrane-bound TRAIL or soluble TRAIL. To demonstrate the anti-glioma activity of AAV-TRAIL gene transfer in vivo, immunodeficient mice bearing pre-established (50–100 mm) subcutaneous U87MG tumors were injected with a single injection of AAV-mbTRAIL, AAV-LZsTRAIL on Day 7, 14 and 21 days following tumor implantation. A significant delay of U87MG tumor growth was observed following AAV-TRAIL gene transfer in comparison to mice that were untreated (FIG. 20). Kaplan Meier analysis demonstrated that AAV-mbTRAIL gene transfer had a significant effect in prolonging the survival of U87MG-tumor bearing mice with a median survival time of 65d (P=0.028) in comparison to a median survival time of 30d in control treated mice (FIG. 21). The combinatorial cytotoxic effects of TRAIL and chemotherapy were also tested in glioma tumor cell lines. As shown in FIG. 22, U87MG and T98G human glioma tumor cell lines, when pre-treated with sub-toxic doses of anti-neoplastic agents (etoposide, BCNU, vincristine), had an augmented cytotoxic effect when combined with treatment soluble TRAIL.

EXAMPLE 6

In Vivo Evaluation of Alternative Stereotypes of AAV for Gene Transfer to the Normal Murine CNS and Orthotopic Tumors.

An rAAV vector plasmid, pAAV-CAG-EGFP-WPRE-BGHpA, which encodes enhanced green fluorescent protein (EGFP) under the control of the CAG promoter was constructed (FIG. 1) by replacing the liver specific promoter (LSP) of the plasmid pAAV-LSP-EGFP-WPRE-BGHpA with the CAG promoter from the plasmid pBacMam-2 (Novagen, Madison, Wis. ). Briefly, the plasmid pAAV-LSP-EGFP-WPRE-BGHpA was cut with Not I, blunted using T4 polymerase, then cut with Xho I, dephosphorylated using Calf Intestinal Phosphatase and a 4902 bp fragment isolated. pBacMam-2 was cut with Xho I, then Hpa I to isolate a 1780 bp fragment. The two fragments were then ligated together using a Rapid Ligation Kit (Roche Applied Science: Mannheim, Germany) to produce pAAV-CAG-EGFP-WPRE-BGHpA. AAV serotype-2, -5, -6, -7 and -8 vectors encoding the EGFP transgene were then prepared and purified according to the methods of Snyder et al., 1997, Nature Genetics 16(3):270–6. The plasmid pUC-ACG was employed as a helper for AAV-2 production, pRepCap5 (Chiorini et al., 1999, J. Virol 73(2):1309–1319) for AAV-5 vector and pRepCap6 (Halbert Cl et al., 2000, Journal of Virology 74(3):1524–32) for AAV-6 packaging. rAAV-7 and AAV-8 vectors were packaged using p5E18-VD2/7 and p5E18-VD2/8 respectively (Gao G P et al., 2002, PNAS 99(18): 11854–11859).

Figure 23:
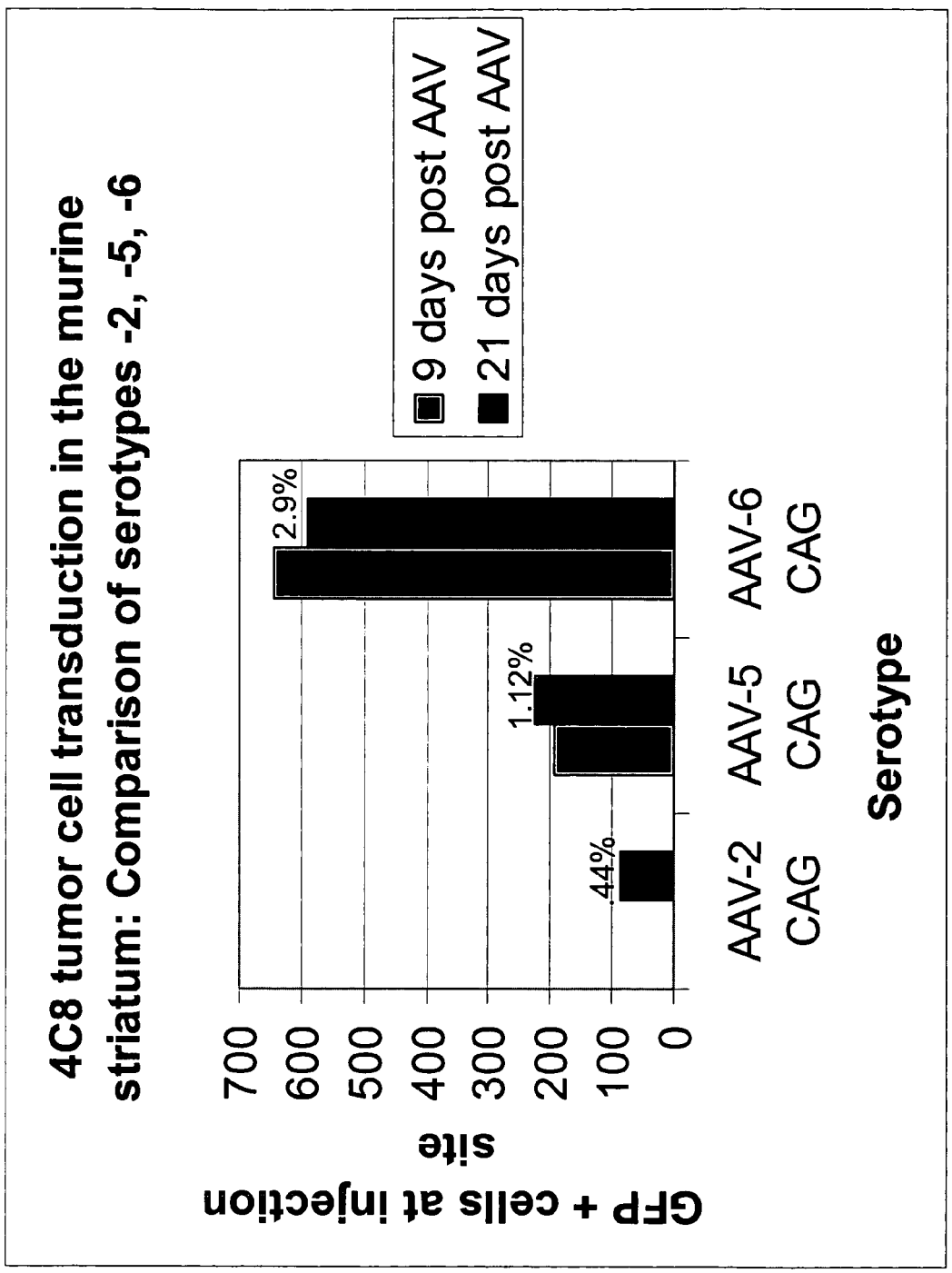
FIG. 23 illustrates the gene transfer efficiency of AAV serotypes-2, -5 and -6 in the murine 4C8 model which has 4C8 glial tumor cells orthotopically implanted within mice. B6D2F1 mice were stereotaxically implanted in the right striatum with 2×10e5 4C8 murine glioma cells. 7 days following implantation 1×10e9 vector genomes of AAV vector serotype-2, -5 or -6 encoding enhanced green fluorescent protein (EGFP) were stereotaxically injected into identical co-ordinates as for the 4C8 tumor implantation. 9 days and 21 days post-AAV injection into the tumor, animals were sacrificed and the brains removed to examine gene transfer to the tumor cells using fluorescent photomicroscopy. Values reflect transduced tumor cells and astrocytes present within the tumor reported as a percentage of the total cells present, as assessed by DAPI staining.
Figure 24:
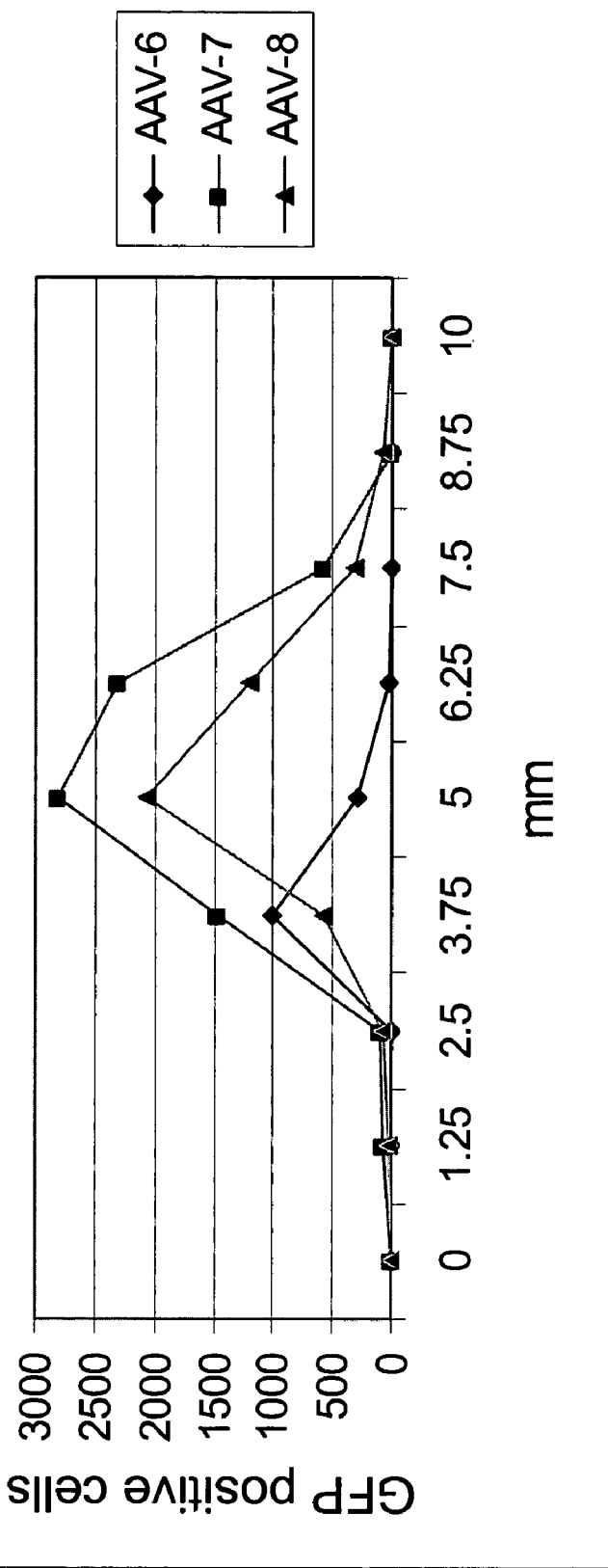
FIG. 24 illustrates the effect of AAV serotype (AAV-6, -7 and -8) on transduction of murine striatum using a GFP reporter gene. B6D2F1 mice were stereotaxically injected in the right striatum with AAV vector serotypes-6, -7 or -8 encoding EGFP under the control of the CAG promoter. 14 days following vector injection animals were sacrificed. brains sectioned and examined under fluorescence microscopy for EGFP expression throughout the brain. EGFP positive cells were quantitated using Image Analysis. The stereotaxic injection point of AAV virus was at 5 mm, with 0 mm representing the front and 10 mm representing the back of the murine brain
Figure 25:
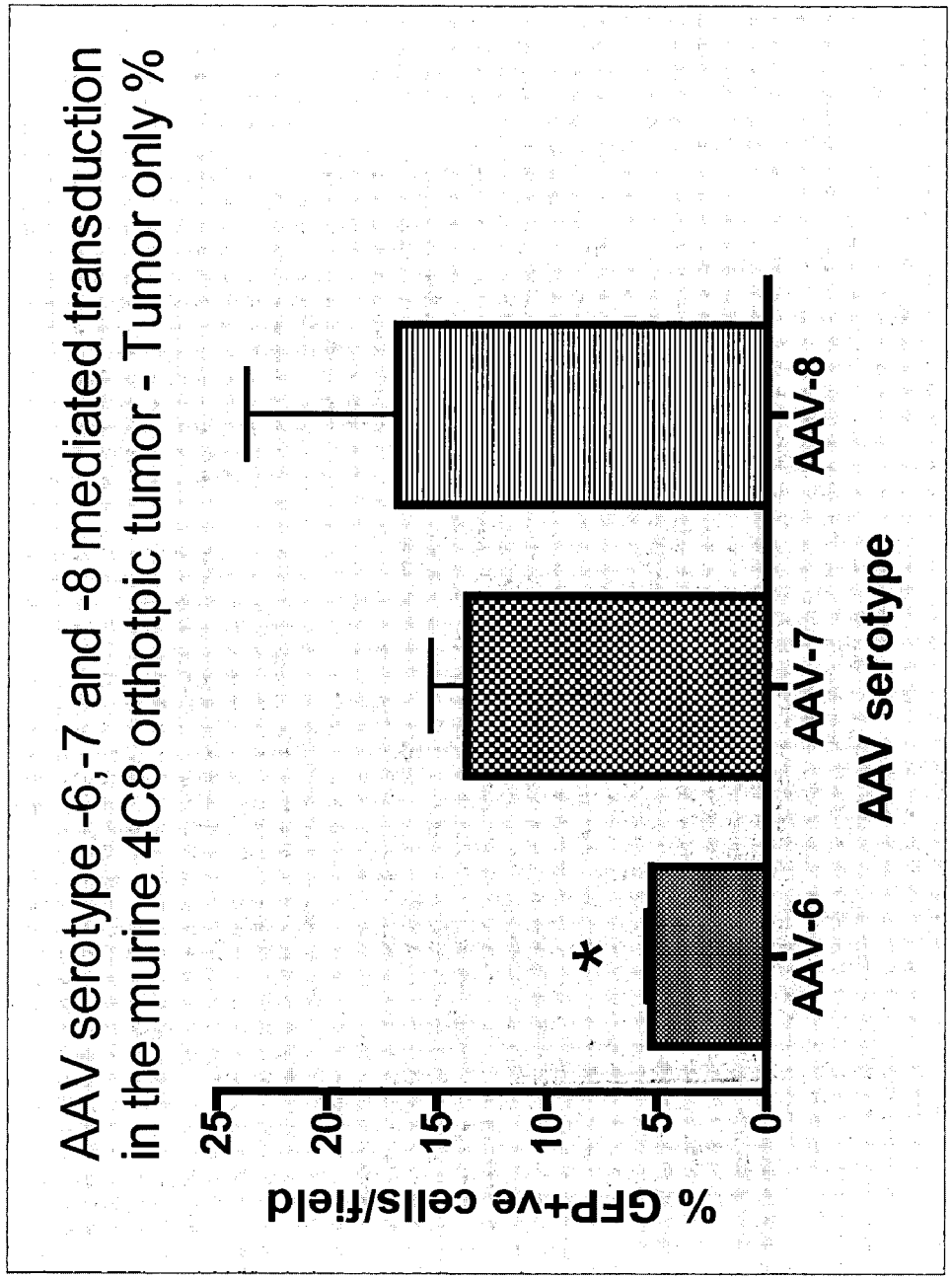
FIG. 25 illustrates the effect of AAV serotype (AAV-6, -7 and -8) on transduction of the 4C8 tumor in the murine CNS. B6D2F1 mice were stereotaxically implanted in the right striatum with 2×10e5 4C8 murine glioma cells. 7 days following implantation 1×10e9 vector genomes of AAV vector serotype-6, -7 or -8 encoding enhanced green fluorescent protein (EGFP) were stereotaxically injected into identical coordinates as used for the 4C8 tumor implantation. 14 days post-AAV injection, animals were sacrificed and the brains removed to examine gene transfer to the tumor cells. Values reflect transduced tumor cells and astrocytes present within the tumor reported as a percentage of the total cells present as assessed by DAPI staining.

To evaluate the transduction efficiency of these modified serotypes in the murine striatum in the presence of a 4C8 tumor, B6D2F1 mice were stereotaxically implanted in the right striatum with 4C8 murine glioma cells. 7 days following 4C8 cell implantation animals were injected with 1×10e9 vector genomes of AAV vector serotype-2, -5 or -6 encoding enhanced green fluorescent protein into identical coordinates as for the tumor implantation. 9 days and 21 days post-AAV injection into the tumor, animals were sacrificed and the brains removed to examine gene transfer under fluorescent photomicroscopy to the tumor cells (FIG. 23). Transduction in the murine CNS was also examined using AAV serotype-6, -7 and -8 in the absence of the 4C8 tumor. B6D2F1 mice were stereotaxically injected in the right striatum with AAV vector serotypes-6, -7 and -8 encoding EGFP under the control of the CAG promoter. 14 days following vector injection animals were sacrificed and brains sectioned and examined under fluorescence microscopy for EGFP expression throughout the brain. EGFP positive cells were quantitated using Image analysis (FIG. 24). In the presence of the orthotopic tumor, AAV-7 and AAV-8 demonstrated an increased level of gene transfer in the B6D2F1/4C8 model 14 days post-injection of virus (FIG. 25). These results demonstrate that different serotypes of AAV, such as AAV-6, -7 and -8 show better gene transfer efficiency to both the normal murine brain and to implanted orthotopic glial tumors such as 4C8 relative to that of AAV-2. These results suggest that AAV-6, -7 and -8 provide an advantage for gene transfer of therapeutic genes in the treatment of glioma.

EXAMPLE 7

Efficacy of Hydrodynamically Expressed VEGF-TRAP in the Treatment of Subcutaneous U87 and C6 Glioma Tumors This study is directed to hydrodynamic gene transfer of rAAV-plasmid encoding anti cancer compounds such as VEGF-TRAP in treatment of human U87 and rat C6 glioma subcutaneous tumors. Mice were injected via tail vein on Day 0 with a plasmid vector encoding VEGF-TRAP and expression was monitored in serum 3 days later. Day 4 post-injection animals are implanted with either U87 or C6 tumor cells. Efficacy of VEGF-TRAP expressed by hydrodynamic delivery was assessed by the rate of tumor growth over the course of the experiment in comparison to pAAV-Null injected mice. Hydrodynamic delivery was carried out as described in Zhang et al., Human Gene Ther., 10:1735–1737, 1999 and Liu et al., Gene Ther., 6:1258–1266, 1999.

The U87 glioma tumor model is described above in Example 3. The C6 glioma tumor model relies on rat C6 human glioma cells cultured under standard conditions, trypsinized, washed in media, spun down and resuspended in media at 50 million cells/ml. 0.2 ml are injected into each mouse (5×106 cells/mouse). In one exemplary study female NCR.nu/nu homozygous mice (Taconic) were dosed via the tail vein with 50 ug of pAAV-CAG-VEGF-TRAP, or pAAV-Null using each of the U87 and C6 glioma models. Studies are typically carried out for 7 to 10 week and mice were monitored by daily observation (following tumor implantation), serum bleeds on Day 3, 7, 14, 28 and 56, twice weekly tumor measurement and evaluation of body weight/body conditions. The study endpoints include tumor volume and weight loss with mice immediately euthanized if tumor volume exceeds 2000 mm$^3$ or weight loss is 15% or greater.

Tumor volumes (mm$^3$) are calculated as 0.5 times length× width×depth measurements in mm. Tumor lag time is defined as time from inoculation to progressive tumor growth or the experiment day when two successive tumor measurements showed increased tumor volume. Tumor growth rate is calculated as the slope of tumor volume over time in days. VEGF-Trap test groups will be compared to AAV-Null test groups to determine efficacy.

EXAMPLE 8

Figure 26:
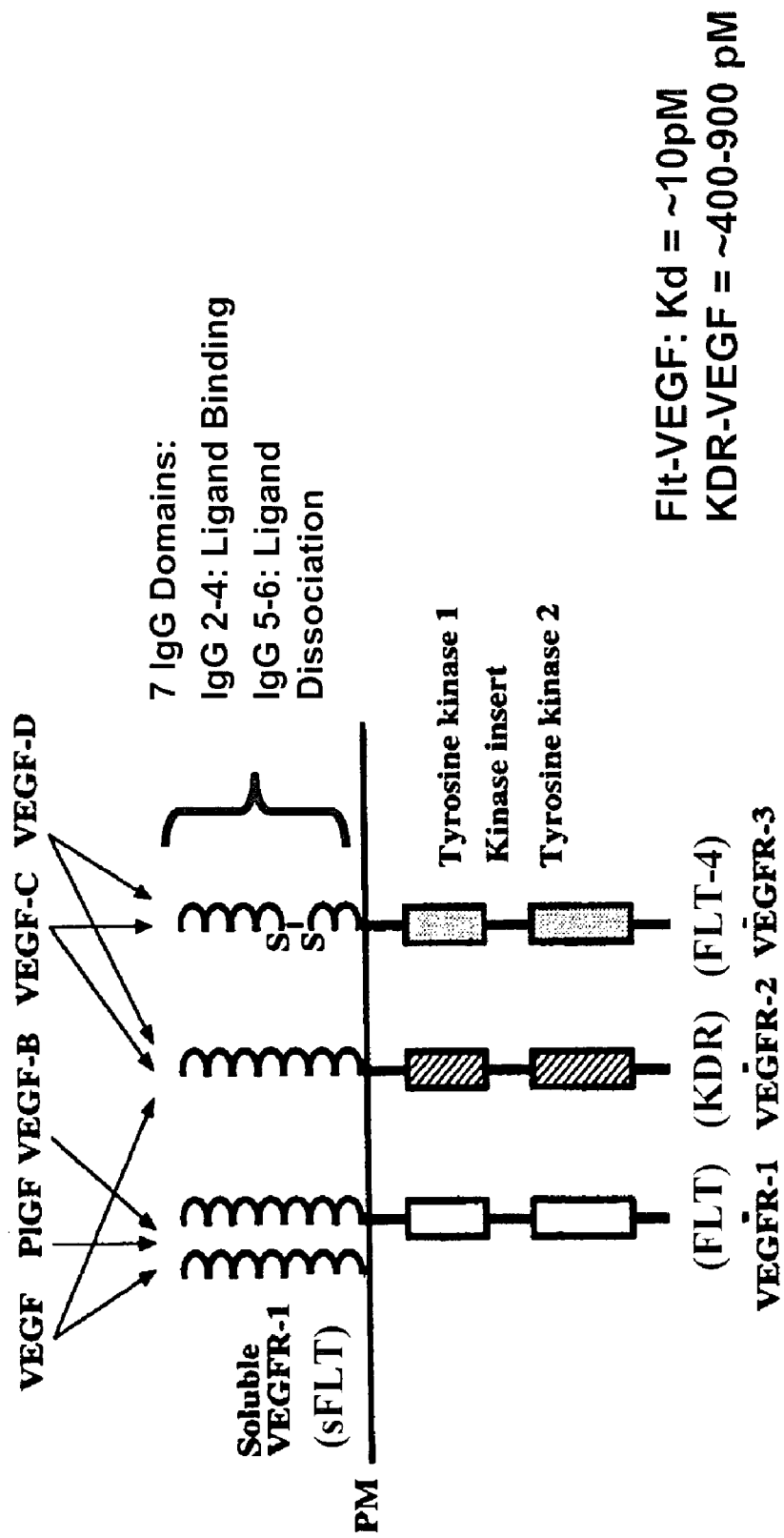
FIG. 26 is a schematic depiction of VEGF & VEGF receptors.
Figure 27:
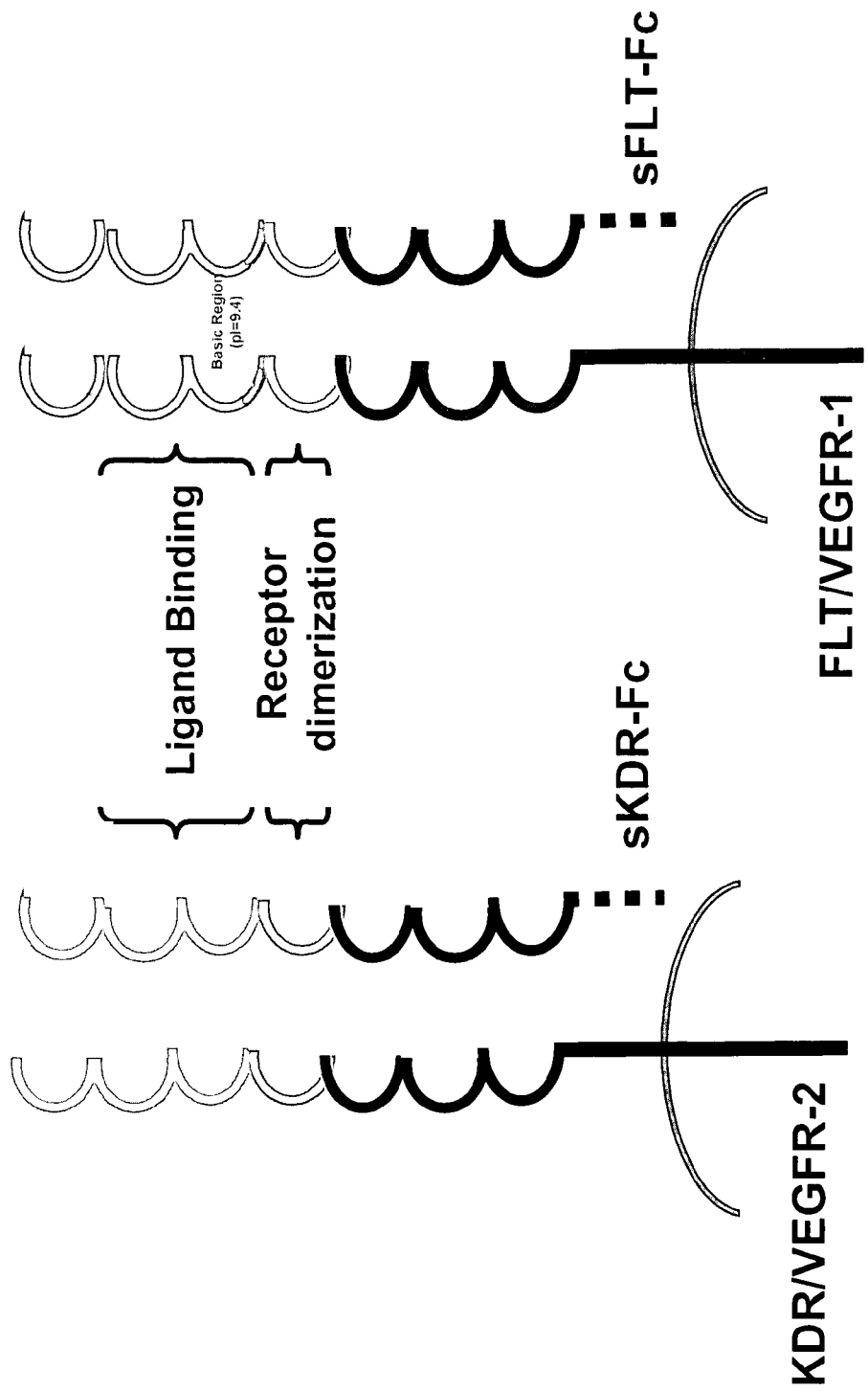
FIG. 27 is a schematic depiction of Soluble VEGFR1 and VEGFR2 IgG1 fusion proteins

Efficacy of AAV-8 Systemically Expressed VEGF-TRAP in the Treatment of Subcutaneous U87 and C6 Glioma Tumors The VEGF ligand and receptor family (FIG. 26) have been strongly implicated in human cancer progression. A soluble hybrid VEGF receptor, VEGF-TRAP (Holash et al., 2002, PNAS 99(17):11393–11398) was constructed (FIG. 27) to block the members of the VEGF ligand family in addition to placental growth factor. VEGF-TRAP consists of domain 2 of VEGFR1 fused to VEGFR2 Domain 3 followed by an IgG1 FC region for receptor dimerization. Secretion of the VEGF-TRAP molecule is achieved by the addition of the signal sequence of VEGFR1 to the N-terminus of the molecule. To create VEGF-TRAP, individual domains of the chimeric molecule were individually amplified using PCR (Expand High Fidelity PCR Kit, Roche Applied Science: Mannheim, Germany). and then joined using a secondary PCR step. For VEGFR1 domain 1 a 316 b.p. PCR product was generated encompassing the region using the primers forward 5' GAC TAG CAG TCC GGA GGT AGA CCT TTC GTA GAG ATG 3' (SEQ ID NO:15), and reverse 5' CGG ACT CAG AAC CAC ATC TAT GAT TGT ATT GGT 3' (SEQ ID NO:16)) in a standard PCR reaction using pBLAST-hFLT-1 (Invivogen, San Diego, Calif.) as a template. A 317 b.p. fragment of VEGFR2 encompassing domain 3 of the soluble receptor was generated using a forward primer 5' ACA ATC ATA GAT GTG GTT CTG AGT CCG TCT CAT GCC CAC TGT GC 3' (SEQ ID NO:18), and reverse 5' GAT AAT GCC CGG GCC CTT TTC ATG GAC CCT GAC AAA TG 3' (SEQ ID NO:19)) on the template pBLAST-hElk-1(Invivogen, San Diego, Calif). A second round of PCR was then conducted to fuse the VEGFR1 domain 2 region with the VEGFR2 domain 3 by using the VEGFR1 domain 2 forward primer and the VEGFR2 domain 3 reverse primer in a PCR reaction employing the previous PCR products as a template, to yield a 633 b.p. band. The IgG1Fc region (737 b.p) was amplified by PCR of the plasmid pTR-CAG-VEGFR3-WPRE-BGHpA (forward primer 5' AGG GCC CGG GCG ACA AAA CTC ACA CAT GCC CAC TGT GC 3' (SEQ ID NO:21), and reverse primer 5' CAT TCG CTA GCA ATT 3' (SEQ ID NO:29)). The Fc IgG1 region was then fused to the 3' end of the VEGFR1 domain 2/VEGFR2 domain 3 fusion using a third round of PCR using the R1 D2 forward primer and the FC region's reverse primer on a reaction using the IgG1 Fc PCR product and the VEGFR1 domain 2/VEGFR2 domain 3 fusion PCR product as a template, giving us a 1.37 Kbp PCR product. This final PCR fusion was then cloned into pBluescript SK+(Stratagene La Jolla, Calif.) following Hinc II digestion using a Rapid Ligation Kit (Roche Applied Science, Mannheim, Germany) to create pBSSK+-d2VEGFR1/d3VEGFR2/IgG1 Fc. The VEGFR1 signal sequence was generated as an synthetic oligonucleotide (direct strand 5' TCG AAG ATC TAT GGT CAG CTA CTG GGA CAC CGG GGT CCT GCT GTG CGC GCT GCT CAG CTG TCT GCT TCT CAC AGG ATC TAG TTC CGG AGG TAG 3' (SEQ ID NO:23) and complementary strand 5' CTA CCT CCG GAA CTA GAT CCT GTG AGA AGC AGA CAG CTG AGC AGC GCG CAC AGC AGG ACC CCG GTG TCC CAG TAG CTG ACC TAA GAT CTT CGA 3' (SEQ ID NO:30)) which was then cut with BspEI and ligated into identical sites of pBSSK+-d2VEGFR1/ d3VEGFR2/IgG1Fc to create pBSSK+-VEGF-TRAP. A rAAV plasmid encoding VEGF-TRAP soluble receptor was constructed by digestion of pBSSK+-VEGF-TRAP with Bgl II and Nsi I and ligation into identical sites of the plasmid pTR-CAG VEGFR3-WPRE-BGHpA. The final expression vector was named pTR-CAG-VEGF-Trap-WPRE-BGHpA. Recombinant AAV-8 vectors encoding the VEGF-Trap expression vector were packaged using p5e18-VD2/8 (Gao GP et al., 2002, PNAS 99(18):11854–11859).

A murine subcutaneous human U87 glioma tumor model and a rat C6 glioma model were used for evaluation of the effect VEGF-TRAP on tumor growth and survival in mice. In the U87 study, 30 mice were implanted with s.c. human U87 tumors on day 0. On day 1 following tumor implantation, mice were intravenously injected by tail vein with 5×10e11 vector genomes of AAV8-VEGF-TRAP (n=10), 5×10e11 vector genomes of AAV8-KONG control (n=10) or PBS (n=10). The preparation of human U87 glioma cells, parameters of the model and endpoint evaluations were carried out as described in Example 3.

Figure 28:
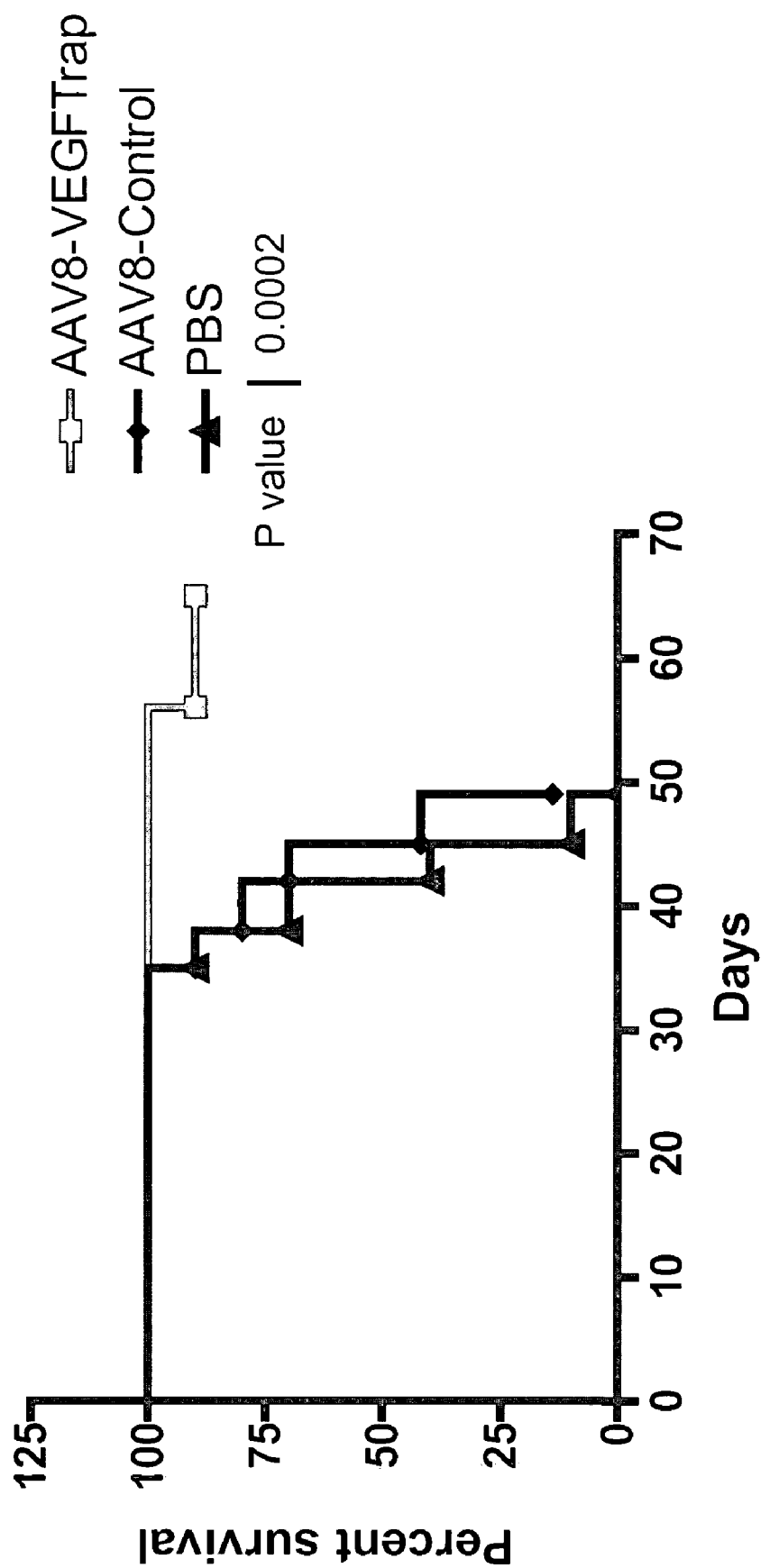
FIG. 28 shows that AAV mediated VEGF-TRAP expression prolongs survival in U87 s.c. tumor-bearing NCRnu.nu mice in the human U87 glioma s.c. model. NCRnu.nu mice were sub-cutaneously challenged with U87 tumors on day 0. On day 1 post-implantation, 5×10e11 vector genomes of AAV serotype 8 vector encoding VEGF-Trap or a null (KONG) control were administered intravenously by tail vein injection. Following vector administration animal survival was assessed up to 65 days. Expression of VEGF-TRAP significantly enhanced survival (p=0.0002). Solid line with square symbols: AAV-VEGF-Trap injected, solid line with diamonds: AAV-KONG (null) control injected, solid line with triangles: PBS injected.

Following vector administration animal survival in the U87 glioma model was assessed up to 65 days (FIG. 28). Expression of VEGF-TRAP exhibited significantly enhanced survival (p=0.0002) compared to both AAV-8 control or PBS injected groups.

For investigating the efficacy of AAV-8 encoded VEGF-Trap in the in the C6 glioma model, mice were intravenously injected by tail vein with 5×10e11 vector genomes of AAV8-CAG-VEGF-TRAP (n=10), 5×10e11 vector genomes of AAV8-KONG control (n=10) or PBS (n=10). 14 days following AAV-8 injection, animals were implanted with s.c. C6 tumors. The preparation of rat C6 glioma cells, parameters of the model and endpoint evaluations were carried out as described in Example 4.

Studies are typically carried out for approximately 8 weeks and mice were monitored by daily observation (following tumor implantation), twice weekly tumor measurement and evaluation of body weight/body conditions. Serum bleeds were conducted at 14 and 28 days post-AAV injection and at sacrifice (300 ul whole blood). The study endpoints include tumor volume and weight loss with mice immediately euthanized if tumor volume exceeds 2000 mm$^3$ or weight loss is 15% or greater. Studies are typically run with 10 mice per group.

Figure 29:
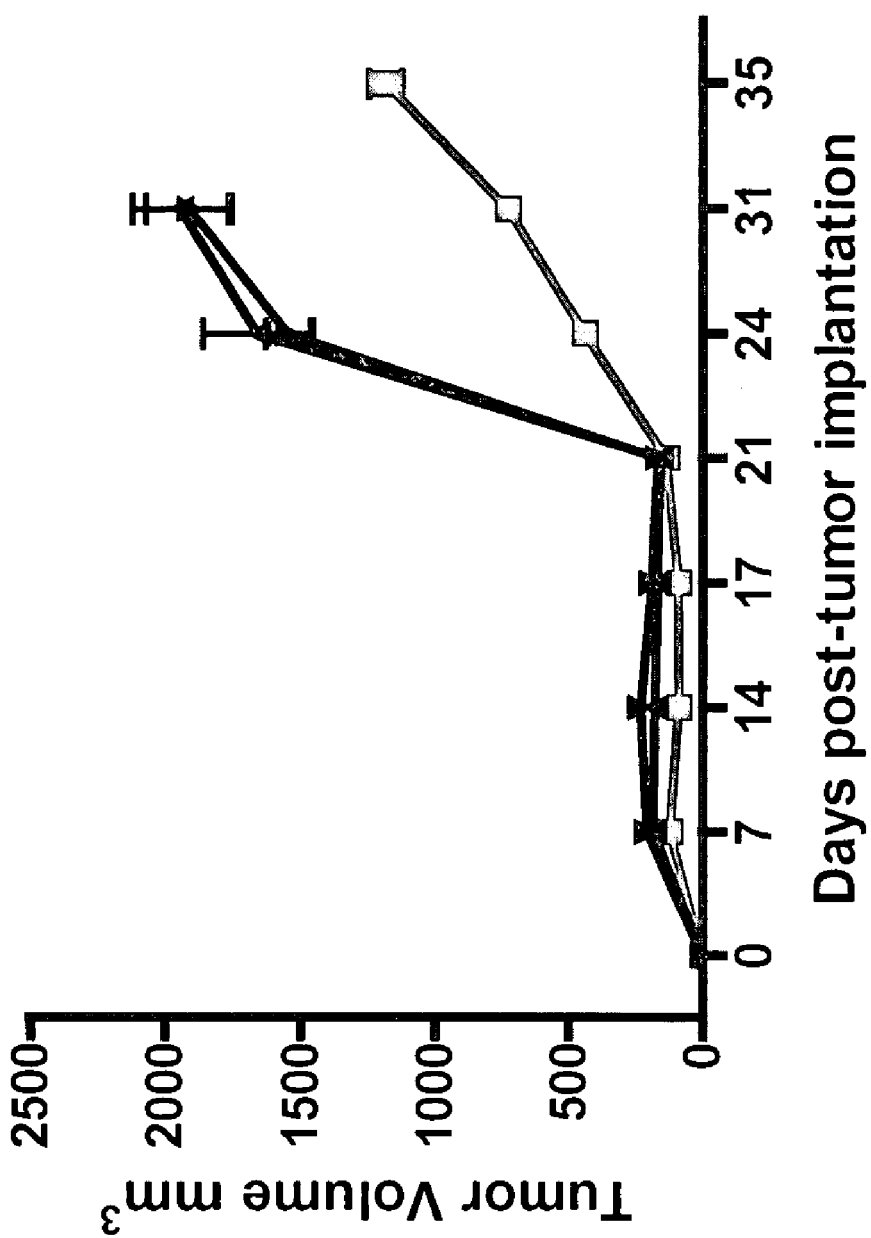
FIG. 29 shows that AAV mediated VEGF-TRAP expression delays the growth of s.c. C6 glioma tumors in NCRnu.nu mice NCRnu.nu mice were administered 5×10e11 vector genomes of AAV serotype 8 vector encoding VEGF-TRAP or a null (KONG) control by tail vein injection. 14 days following virus injection, mice were then sub-cutaneously challenged with C6 tumor cells. Tumor volumes were measured at indicated times up to 35 days post C6 tumor implantation. Solid line with square symbols: AAV-VEGF-Trap injected, solid line with diamonds: AAV-KONG (null) control injected, solid line with triangles: PBS injected.
Figure 30:
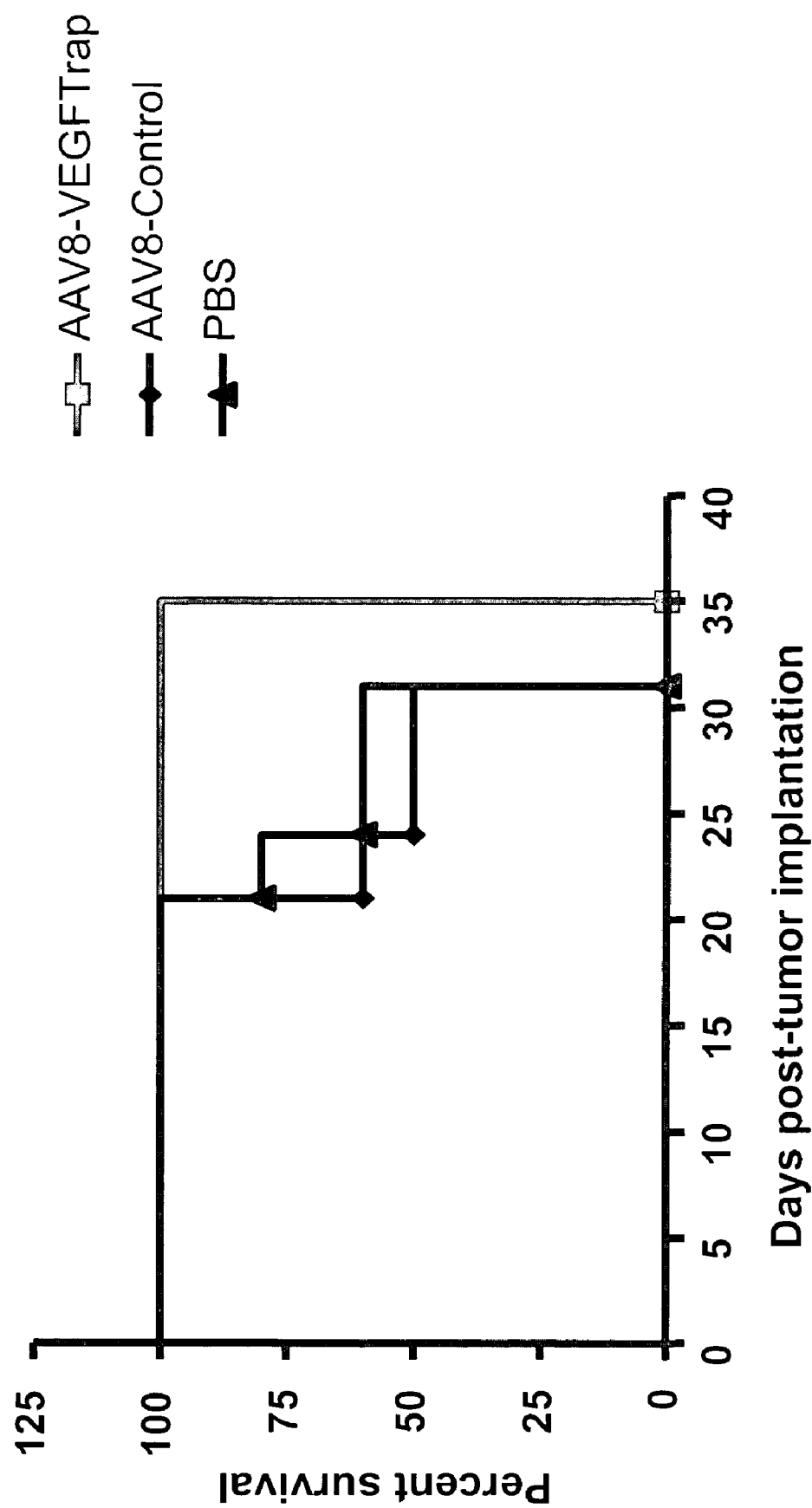
FIG. 30 shows that AAV mediated VEGF-TRAP expression prolongs survival in s.c. C6 tumor-bearing NCRnu.nu mice in the rat C6 glioma s.c. model. NCRnu.nu mice were administered 5×10e11 vector genomes of AAV serotype 8 vector encoding VEGF-Trap or a null (KONG) control by tail vein injection. 14 days following virus injection, mice were sub-cutaneously challenged with C6 tumor cells. Survival advantage was calculated from Kaplan Meier curves as shown. Expression of VEGF-TRAP significantly enhanced survival (p=0.001). Solid line with square symbols: AAV-VEGF-TRAP injected, solid line with diamonds: AAV-KONG (null) control injected, solid line with triangles: PBS injected.

Tumor volumes were measured at indicated times up to 35 days post C6 tumor implantation (FIG. 29) and indicate a significant inhibition of tumor growth by expression of VEGF-TRAP which correlated with a survival advantage (FIG. 30) as calculated from Kaplan Meier curves (p=0.001).

EXAMPLE 9

Figure 31:
FIG. 31 shows the results of MRI of mouse brains demonstrating that orthotopic 4C8 tumor growth is reduced at 30 days post-implantation by AAV mediated VEGF-TRAP expression. B6D2F1 mice were stereotaxically implanted in the right striatum with 2×10e5 4C8 murine glioma cells. 7 days following 4C8 implantation 1.2×10e9 vector genomes of AAV-6 encoding VEGF-TRAP or EGFP control were stereotaxically injected into identical coordinates used for the 4C8 tumor implantation. Following vector injection, tumor volume was monitored using MRI imaging. CG-82 (top row) represents serial 1.2 mm sections through the brain of an animal injected with control vector, where tumor growth can be observed as a dark mass in the striatum of the animal at 30 days post-tumor implantation. CG-77 (bottom row) represents serial 1.2 mm sections through the brain of an animal injected with VEGF-TRAP vector, where tumor growth is notably absent 30 days post-tumor implantation.
Figure 32:
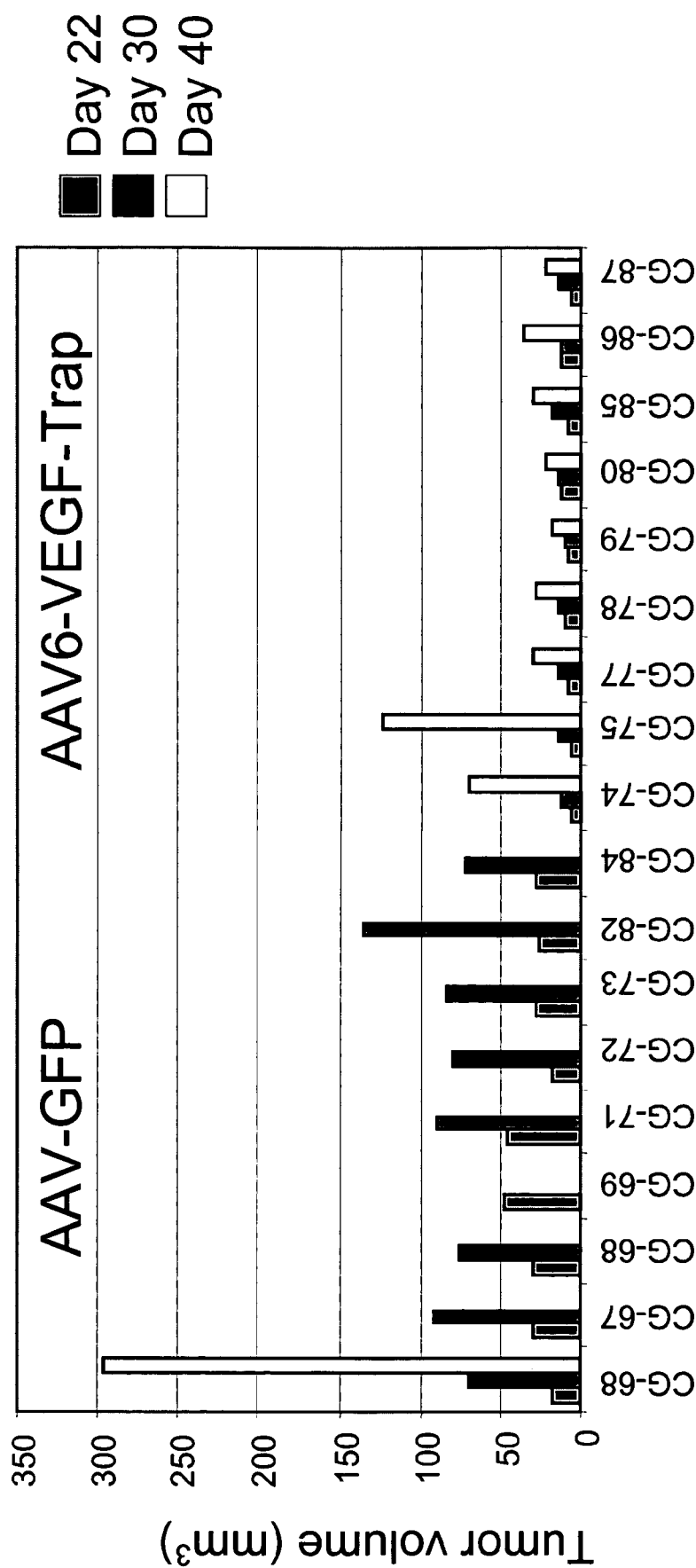
FIG. 32 shows that AAV mediated VEGF-TRAP expression reduces orthotopic 4C8 tumor growth at day 22, 30 and 40 days post vector injection. B6D2F1 mice were stereotaxically implanted in the right striatum with 2×10e5 4C8 murine glioma cells. 7 days following 4C8 implantation 1.2×10e9 vector genomes of AAV-6 encoding VEGF-TRAP or EGFP control were stereotaxically injected into identical coordinates as for the 4C8 tumor implantation. Following vector injection, tumor size was assessed using MRI imaging of tumors followed by NIH image analysis to determine total tumor volume in mm$^3$. The results from individual animals are displayed 22, 30 and 40 days post-tumor implantation.
Figure 33A:
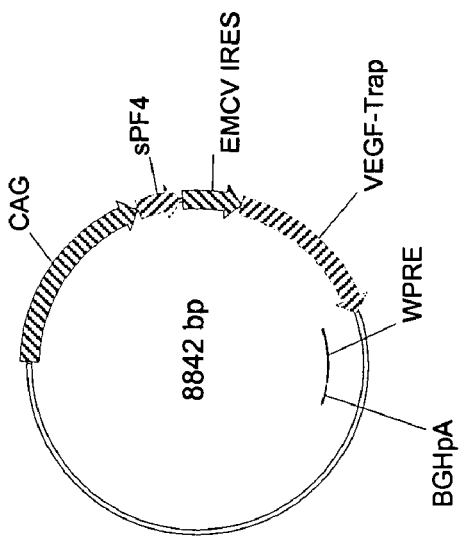
FIGS. 33A–D depict exemplary plasmids for the expression of soluble platelet factor 4 (sPF4) and VEGF TRAP wherein the plasmids comprise the coding sequences and either a F2A sequence or an IRES in alternate orientations as described in Example 10. The figures illustrate plasmids comprising in the 5' to 3' direction: sPF4:F2A:VEGF TRAP (pTR-CAG-sPF4-F2A-VT.
Figure 33B:
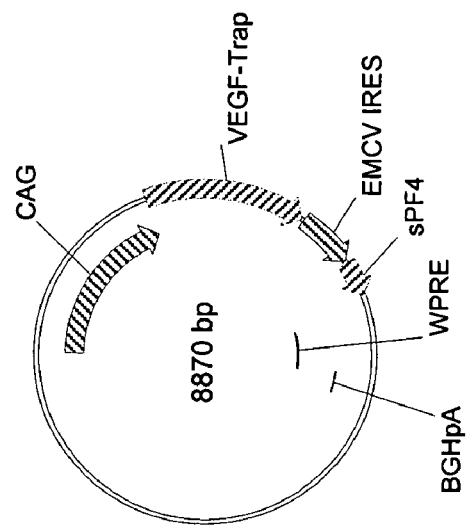
Figure 33C:
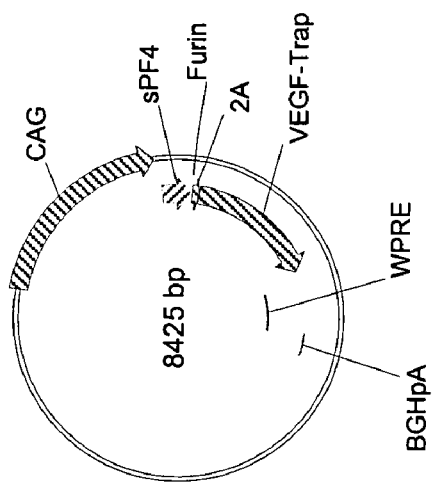
Figure 33D:
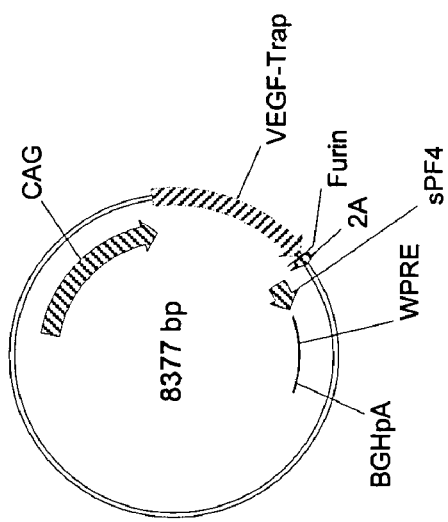

Efficacy of AAV-6 Expressed VEGF-Trap in the Treatment of Orthotopic 4C8 Glioma Tumors A recombinant AAV-6 vector encoding VEGF-TRAP was prepared and purified according to Snyder et al., 1997, Nature Genetics 16(3):270–6 using the AAV-6 packaging plasmid pRepCap6 (Halbert Cl et al., 2000, Journal of Virology 74(3):1524–32). B6D2F1 mice were stereotaxically implanted in the right striatum with 2×10E5 4C8 murine glioma cells. 7 days following 4C8 implantation 1.2×10e9 vector genomes of AAV-6 encoding VEGF-Trap or EGFP control were stereotaxically injected into identical co-ordinates as for tumor implantation (right striatum). Following vector injection, tumor volume was monitored in the animals using MRI (FIG. 31 and FIG. 32) demonstrating a clear tumor inhibition following AAV-6 mediated VEGF-TRAP expression. Tumor inhibition correlated with a survival advantage (Figure X—insert in replacement of FIG. 33) as calculated from Kaplan Meier curves (p=X).

EXAMPLE 10

Expression of VEGF-Trap and PF-4(DLR) from a Single Promoter Construct for Combined Cancer Therapy In this example the VEGF-TRAP and PF-4(DLR) genes are expressed from a single promoter using the F2A (Ryan et al., J. Gen. Virol. 72:2727–2732, 1991; Vakharia et al., J. Virol. 61:3199–3207, 1987; Donnelly et al., J. Gen. Virol. 78:13–21, 1997) protein cleavage site for co-expression of 2 anti-angiogenic genes. The plasmids that were evaluated are diagrammed in FIGS. 33A–D. In these examples a 2A or IRES sequence was used to fuse the VEGF-TRAP and PF-4(DLR) coding sequence together downstream of the CAG promoter. Both orientations of the two genes relative to the F2A and IRES sequences were cloned and evaluated. These plasmids were initially tested by transient transfection into 293T cells, which was performed in a 6-well dish using a FUGENE 6 kit (Roche Applied Science, Mannheim, Germany). The transfections were done in triplicate using 2×105 cells and 1 μg of DNA per well, and 200 ng of a CAG-GFP expressing plasmid was added to each sample as a transfection control. Cell culture supernatants were harvested approximately 40 hours later and assayed for VEGF-TRAP and PF-4(DLR) expression using human IgG (Bethyl Laboratories) and Asserachrom PF-4 ELISA assays (Diagnostica Stago), respectively. In the IRES containing vectors, the gene upstream of the IRES is expressed at high levels whereas the gene downstream of the IRES is very poorly expressed (FIG. 34). This is in striking contrast to the F2A containing vectors, which express both proteins at equal levels. Expression levels of the two proteins are almost identical when placed either upstream or downstream F2A site, indicating that the F2A sequence appears to function independent of orientation. These data show that the F2A allows expression of two genes from a single promoter construct.

From the foregoing, it can be appreciated that the compositions and methods of the present invention offer advantages in providing a means for effective and sustained delivery of one or more therapeutic compounds to a cancer patient.

TABLE 11

Table of Sequences

| SEQ ID NO | SEQUENCE |
|---|---|
| 1 | nucleic acid coding sequence for membrane bound human TRAIL full length protein: ATGGCTATGATGGAGGTCCAGGGGGGACCCAGCCTGGGACAGACCTGCGTGCT GATCGTGATCTTTACAGTGCTCCTGCAGTCTCTCTGTGTGGCTGTAACTTACGTG |

TABLE 11-continued

Table of Sequences

| SEQ ID NO | SEQUENCE |
|---|---|
| | TACTTTACCAACGAGCTGAAGCAGATGCAGGACAAGTACTCCAAAAGTGGCATTG |
| | CTTGTTTCTTAAAAGAAGATGACAGTTATTGGGACCCCAATGACGAAGAGAGTAT |
| | GAACAGCCCCTGCTGGCAAGTCAAGTGGCAACTCCGTCAGCTCGTTAGAAAGAT |
| | GATTTTGAGAACCTCTGAGGAAACCATTTCTACAGTTCAAGAAAAGCAACAAAATA |
| | TTTCTCCCCTAGTGAGAGAAAGAGGTCCTCAGAGAGTAGCAGCTCACATAACTGG |
| | GACCAGAGGAAGAAGCAACACATTGTCTTCTCCAAACTCCAAGAATGAAAAGGCT |
| | CTGGGCCGCAAAATAAACTCCTGGGAATCATCAAGGAGTGGGCATTCATTCCTGA |
| | GCAACTTGCACTTGAGGAATGGTGAACTGGTCATCCATGAAAAAGGGTTTTACTA |
| | CATCTATTCCCAAACATACTTTCGATTTCAGGAGGAAATAAAAGAAAACACAAAGA |
| | ACGACAAACAAATGGTCCAATATATTTACAAATACACAAGTTATCCTGACCCTATA |
| | TTGTTGATGAAAAGTGCTAGAAATAGTTGTTGGTCTAAAGATGCAGAATATGGACT |
| | CTATTCCATCTATCAAGGGGAATATTTGAGCTTAAGGAAAATGACAGAATTTTTG |
| | TTTCTGTAACAAATGAGCACTTAATAGACATGGACCATGAAGCCAGTTTTTTCGGG |
| | GCCTTTTTAGTTGGCTAA |
| 2 | full length protein sequence for membrane bound human TRAIL (amino-acids 1–281):<br>MAMMEVQGGPSLGQTCVLIVIFTVLLQSLCVAVTYVYFTNELKQMQDKYSKSGIACFL<br>KEDDSYWDPNDEESMNSPCWQVKWQLRQLVRKMILRTSEETISTVQEKQQNISPLV<br>RERGPQRVAAHITGTRGRSNTLSSPNSKNEKALGRKINSWESSRSGHSFLSNLHLRN<br>GELVIHEKGFYYIYSQTYFRFQEEIKENTKNDKQMVQYIYKYTSYPDPILLMKSARNSC<br>WSKDAEYGLYSIYQGGIFELKENDRIFVSVTNEHLIDMDHEASFFGAFLVG |
| 3 | nucleic acid coding sequence for isoluecine zipper modified variant version of soluble human TRAIL (LZsTRAIL):<br>CATGGATGCAATGAAGAGAGGGCTCTGCTGTGTGCTGCTGCTGTGTGGAGCAGT<br>CTTCGTTTCGCCGTCCGGCATGAAGCAGATCGAGGACAAAATTGAGGAAATCCTT<br>TCGAAGATTTACCACATCGAGAACGAGATCGCCCGGATTAAGAAGCTTATTGGCG<br>AGAGGGAAGGATCCGGTGTGAGAGAAAGAGGTCCTCAGAGAGTAGCAGCTCACA<br>TAACTGGGACCAGAGGAAGAAGCAACACATTGTCTTCTCCAAACTCCAAGAATGA<br>AAAGGCTCTGGGCCGCAAAATAAACTCCTGGGAATCATCAAGGAGTGGGCATTC<br>ATTCCTGAGCAACTTGCACTTGAGGAATGGTGAACTGGTCATCCATGAAAAAGGG<br>TTTTACTACATCTATTCCCAAACATACTTTCGATTTCAGGAGGAAATAAAAGAAAA<br>CACAAAGAACGACAAACAAATGGTCCAATATATTTACAAATACACAAGTTATCCTG<br>ACCCTATATTGTTGATGAAAAGTGCTAGAAATAGTTGTTGGTCTAAAGATGCAGAA<br>TATGGACTCTATTCCATCTATCAAGGGGAATATTTGAGCTTAAGGAAAATGACAG<br>AATTTTTGTTTCTGTAACAAATGAGCACTTGATAGACATGGACCATGAAGCCAGTT<br>TTTTCGGGGCCTTTTTAGTTGGCTAAG |
| 4 | amino acid sequence for isoluecine zipper modified variant version of soluble human TRAIL (LZsTRAIL):<br>MDAMKRGLCCVLLLCGAVFVSPSGMKQIEDKIEEILSKIYHIENEIARIKKLIGEREGSG<br>VRERGPQRVAAHITGTRGRSNTLSSPNSKNEKALGRKINSWESSRSGHSFLSNLHLR |

TABLE 11-continued

Table of Sequences

| SEQ ID NO | SEQUENCE |
|---|---|

NGELVIHEKGFYYIYSQTYFRFQEEIKENTKNDKQMVQYIYKYTSYPDPILLMKSARNS

CWSKDAEYGLYSIYQGGIFELKENDRIFVSVTNEHLIDMDHEASFFGAFLVG 5 amino acid sequence for isoleucine zipper motif added to soluble human TRAIL
MKQIEDKIEEILSKIYHIENEIARIKKLIGERE 6 nucleic acid coding sequence for platelet factor-4 (PF-4):
ATGAGCTCCGCAGCCGGGTTCTGCGCCTCACGCCCCGGGCTGCTGTTCCTGGG

GTTGCTGCTCCTGCCACTTGTGGTCGCCTTCGCCAGCGCTGAAGCTGAAGAAGA

TGGGGACCTGCAGTGCCTGTGTGTGAAGACCACCTCCCAGGTCCGTCCCAGGCA

CATCACCAGCCTGGAGGTGATCAAGGCCGGACCCCACTGCCCCACTGCCCAACT

GATAGCCACGCTGAAGAATGGAAGGAAAATTTGCTTGGACCTGCAAGCCCCGCT

GTACAAGAAAATAATTAAGAAACTTTTGGAGAGTTAG 7 amino acid coding sequence for platelet factor-4 (PF-4):
MSSAAGFCASRPGLLFLGLLLLPLWAFASAEAEEDGDLQCLCVKTTSQVRPRHITSL

EVIKAGPHCPTAQLIATLKNGRKICLDLQAPLYKKIIKKLLES 8 nucleic acid coding sequence for platelet factor-4 (PF-4) with the DLR mutation:
ATGAGCTCCGCAGCCGGGTTCTGCGCCTCACGCCCCGGGCTGCTGTTCCTGGG

GTTGCTGCTCCTGCCACTTGTGGTCGCCTTCGCCAGCGCTGAAGCTGAAGAAGA

TGGGGACCTGCAGTGCCTGTGTGTGAAGACCACCTCCCAGGTCCGTCCCAGGCA

CATCACCAGCCTGGAGGTGATCAAGGCCGGACCCCACTGCCCCACTGCCCAACT

GATAGCCACGCTGAAGAATGGAAGGAAAATTTGCTTGGACCTGCGAGCCCCGCT

GTACAAGAAAATAATTAAGAAACTTTTGGAGAGTTAG 9 amino acid coding sequence for platelet factor-4 (PF-4) with the DLR mutation:
MSSMGFCASRPGLLFLGLLLLPLWAFASAEAEEDGDLQCLCVKTTSQVRPRHITSLEVIKAGPHCPTAQ

LIATLKNGRKICLDLRAPLYKKIIKKLLES

10 PCR primer:sPF4(DLR) Forward
(ggAAAATTTgCTTggACCTgCgAgCCCCgCTgTACAAgAAAATAATTAAg)

11 PCR primer:sPF4(DLR) Reverse
(CTTAATTATTTTCTTgTACAgCggggCTCgCAggTCCAAgCAAATTTTCC)

12 nucleic acid coding sequence for VEGF-TRAP:
ATGGTCAGCTACTGGGACACCGGGGTCCTGCTGTGCGCGCTGCTCAGCTGTCTGCTTCTCACAGGA

TCTAGTTCCGGAAGTAGACCTTTCGTAGAGATGTACAGTGAAATCCCCGAAATTATACACATGACTGA

AGGAAGGGAGCTCGTCATTCCCTGCCGGGTTACGTCACCTAACATCACTGTTACTTTAAAAAAGTTTC

CACTTGACACTTTGATCCCTGATGGAAAACGCATAATCTGGGACAGTAGAAAGGGCTTCATCATATCA

AATGCAACGTACAAAGAAATAGGGCTTCTGACCTGTGAAGCAACAGTCAATGGGCATTTGTATAAGA

CAAACTATCTCACACATCGACAAACCAATACAATCATAGATGTGGTTCTGAGTCCGTCTCATGGAATT

GAACTATCTGTTGGAGAAAAGCTTGTCTTAAATTGTACAGCAAGAACTGAACTAAATGTGGGGATTGA

CTTCAACTGGGAATACCCTTCTTCGAAGCATCAGCATAAGAAACTTGTAAACCGAGACCTAAAAACCC

AGTCTGGGAGTGAGATGAAGAAATTTTTGAGCACCTTAACTATAGATGGTGTAACCCGGAGTGACCA

AGGATTGTACACCTGTGCAGCATCCAGTGGGCTGATGACCAAGAAGAACAGCACATTTGTCAGGGT

TABLE 11-continued

Table of Sequences

| SEQ ID NO | SEQUENCE |
|---|---|
| | CCATGAAAAGGGCCCGGGCGACAAAACTCACACATGCCCACTGTGCCCAGCACCTGAACTCCTGGG |
| | GGGACCGTCAGTCTTCCTCTTCCCCCCAAAACCCAAGGACACCCTCATGATCTCCCGGACCCCTGA |
| | GGTCACATGCGTGGTGGTGGACGTGAGCCACGAAGACCCTGAGGTCAAGTTCAACTGGTACGTGGA |
| | CGGCGTGGAGGTGCATAATGCCAAGACAAAGCCGCGGGAGGAGCAGTACAACAGCACGTACCGTG |
| | TGGTCAGCGTCCTCACCGTCCTGCACCAGGACTGGCTGAATGGCAAGGAGTACAAGTGCAAGGTCT |
| | CCAACAAAGCCCTCCCAGCCCCCATCGAGAAAACCATCTCCAAAGCCAAAGGGCAGCCCCGAGAAC |
| | CACAGGTGTACACCCTGCCCCCATCCCGGGATGAGCTGACCAAGAACCAGGTCAGCCTGACCTGCC |
| | TAGTCAAAGGCTTCTATCCCAGCGACATCGCCGTGGAGTGGGAGAGCAATGGGCAGCCGGAGAAC |
| | AACTACAAGGCCACGCCTCCCGTGCTGGACTCCGACGGCTCCTTCTTCCTCTACAGCAAGCTCACC |
| | GTGGACAAGAGCAGGTGGCAGCAGGGGAACGTCTTCTCATGCTCCGTGATGCATGAGGCTCTGCAC |
| | AACCACTACACGCAGAAGAGCCTCTCCCTGTCTCCGGGTAAATGA |
| 13 | amino acid coding sequence for VEGF-TRAP:<br>MVSYWDTGVLLCALLSCLLLTGSSSGGRPFVEMYSEIPEIIHMTEGRELVIPCRVTSPNITVTLKKFPLDTLI<br>PDGKRIIWDSRKGFIISNATYKEIGLLTCEATVNGHLYKTNYLTHRQTNTIIDWLSPSHGIELSVGEKLVLNC<br>TARTELNVGIDFNWEYPSSKHQHKKLVNRDLKTQSGSEMKKFLSTLTIDGVTRSDQGLYTCAASSGLMTK<br>KNSTFVRVHEKGPGDKTHTCPLCPAPELLGGPSVFLFPPKPKDTLMISRTPEVTCVVVDVSHEDPEVKFN<br>WYVDGVEVHNAKTKPREEQYNSTYRWSVLTVLHQDWLNGKEYKCKVSNKALPAPIEKTISKAKGQPRE<br>PQVYTLPPSRDELTKNQVSLTCLVKGFYPSDIAVEWESNGQPENNYKATPPVLDSDGSFFLYSKLTVDKS<br>RWQQGNVFSCSVMHEALHNHYTQKSLSLSPGK |
| 14 | nucleic acid coding sequence for VEGFR1 domain 2; 330 b.p. PCR product:<br>GACTAGCAGTCCGGAGGTAGACCTTTCGTAGAGATGTACAGTGAAATCCCCGAAATTATACACATGA<br>CTGAAGGAAGGGAGCTCGTCATTCCCTGCCGGGTTACGTCACCTAACATCACTGTTACTTTAAAAAA<br>TAACATCACTGTTACTTTAAAAAAGTTTCCACTTGACACTTTGATCCCTGATGGAA<br>AACGCATAATCTGGGACAGTAGAAAGGGCTTCATCATATCAAATGCAACGTACAA<br>AGAAATAGGGCTTCTGACCTGTGAAGCAACAGTCAATGGGCATTTGTATAAGACA<br>AACTATCTCACACATCGACAAACCAATACAATCATAGATGTGGTTCTGAGTCCG |
| 15 | PCR primer: VEGFR1 domain 2 Forward<br>5' GAC TAG CAG TCC GGA GGT AGA CCT TTC GTA GAG ATG 3' |
| 16 | PCR primer: VEGFR1 domain 2 Reverse<br>5' CGG ACT CAG AAC CAC ATC TAT GAT TGT ATT GGT |
| 17 | nucleic acid coding sequence for VEGFR2 domain 3; 333 b.p. PCR product:<br>ACAATCATAGATGTGGTTCTGAGTCCGTCTCATGGAATTGAACTATCTGTTGGAG<br>AAAAGCTTGTCTTAAATTGTACAGCAAGAACTGAACTAAATGTGGGGATTGACTTC<br>AACTGGGAATACCCTTCTTCGAAGCATCAGCATAAGAAACTTGTAAACCGAGACC<br>TAAAAACCCAGTCTGGGAGTGAGATGAAGAAATTTTTGAGCACCTTAACTATAGAT<br>GGTGTAACCCGGAGTGACCAAGGATTGTACACCTGTGCAGCATCCAGTGGGCTG<br>ATGACCAAGAAGAACAGCACATTTGTCAGGGTCCATGAAAAGGGCCCGGGCATT<br>ATC |
| 18 | PCR primer: VEGFR2 domain 3 Forward |

TABLE 11-continued

Table of Sequences

| SEQ ID NO | SEQUENCE |
|---|---|

5' ACA ATC ATA GAT GTG GTT CTG AGT CCG TCT CAT GCC CAC TGT GC 3'

19 PCR primer: VEGFR2 domain 3 Reverse
5' GAT AAT GCC CGG GCC CTT TTC ATG GAC CCT GAC AAA TG 3'

20 nucleic acid coding sequence for IgG1 FC region; 737 b.p. PCR product:
AGGGCCCGGGCGACAAAACTCACACATGCCCACTGTGCCCAGCACCTGAACTCC

TGGGGGGACCGTCAGTCTTCCTCTTCCCCCCAAAACCCAAGGACACCCTCATGA

TCTCCCGGACCCCTGAGGTCACATGCGTGGTGGTGGACGTGAGCCACGAAGAC

CCTGAGGTCAAGTTCAACTGGTACGTGGACGGCGTGGAGGTGCATAATGCCAAG

ACAAAGCCGCGGGAGGAGCAGTACAACAGCACGTACCGTGTGGTCAGCGTCCTC

ACCGTCCTGCACCAGGACTGGCTGAATGGCAAGGAGTACAAGTGCAAGGTCTCC

AACAAAGCCCTCCCAGCCCCCATCGAGAAAACCATCTCCAAAGCCAAAGGGCAG

CCCCGAGAACCACAGGTGTACACCCTGCCCCCATCCCGGGATGAGCTGACCAAG

AACCAGGTCAGCCTGACCTGCCTAGTCAAAGGCTTCTATCCCAGCGACATCGCC

GTGGAGTGGGAGAGCAATGGGCAGCCGGAGAACAACTACAAGGCCACGCCTCC

CGTGCTGGACTCCGACGGCTCCTTCTTCCTCTACAGCAAGCTCACCGTGGACAA

GAGCAGGTGGCAGCAGGGGAACGTCTTCTCATGCTCCGTGATGCATGAGGCTCT

GCACAACCACTACACGCAGAAGAGCCTCTCCCTGTCTCCGGGTAAATGA

21 PCR primer: IgG1 FC region Forward
5' AGG GCC CGG GCG ACA AAA CTC ACA CAT GCC CAC TGT GC 3'

22 PCR primer: IgG1 FC region Reverse
5' CAA TG CTA GCTCA TTT ACC CGG 3'

23 VEGFR1 signal sequence synthetic oligonucleotide direct strand
5' TCG AAG ATC TAT GGT CAG CTA CTG GGA CAC CGG GGT CCT GCT GTG

CGC GCT GCT CAG CTG TCT GCT TCT CAC AGG ATC TAG TTC GGA GGA G

3'

24 exemplary 2A coding sequence from Example 10
GCTCCAGTAAAGCAGACTCTAAACTTCGATCTTCTCAAGCTCGCTGGAGATGTTG

AGAGCAACCCAGGTCCA 25 exemplary WPRE sequence
AATCAACCTCTGGATTACAAAATTTGTGAAAGATTGACTGGTATTCTTAACTATGTT

GCTCCTTTTACGCTATGTGGATACGCTGCTTTAATGCCTTTGTATCATGCTATTGC

TTCCCGTATGGCTTTCATTTTCTCCTCCTTGTATAAATCCTGGTTGCTGTCTCTTTA

TGAGGAGTTGTGGCCCGTTGTCAGGCAACGTGGCGTGGTGTGCACTGTGTTTGC

TGACGCAACCCCCACTGGTTGGGGCATTGCCACCACCTGTCAGCTCCTTTCCGG

GACTTTCGCTTTCCCCCTCCCTATTGCCACGGCGGAACTCATCGCCGCCTGCCTT

GCCCGCTGCTGGACAGGGGCTCGGCTGTTGGGCACTGACAATTCCGTGGTGTTG

TCGGGGAAGCTGACGTCCTTTCCATGGCTGCTCGCCTGTGTTGCCACCTGGATT

CTGCGCGGGACGTCCTTCTGCTACGTCCCTTCGGCCCTCAATCCAGCGGACCTT

CCTTCCCGCGGCCTGCTGCCGGCTCTGCGGCCTCTTCCGCGTCTTCGCCTTCGC

CCTCAGACGAGTCGGATCTCCCTTTGGGCCGCCTCCCCGCCTGG

TABLE 11-continued

Table of Sequences

| SEQ ID NO | SEQUENCE |
|---|---|
| 26 | bGHpolyA (Bovine Growth Hormone Polyadenylation Signal Sequence)<br>GTGAGATCCGCTCGCTGATCAGCCTCGACTGTGCCTTCTAGTTGCCAGCCATCT<br>GTTGTTTGCCCCTCCCCCGTGCCTTCCTTGACCCTGGAAGGTGCCACTCCCACT<br>GTCCTTTCCTAATAAAATGAGGAAATTGCATCGCATTGTCTGAGTAGGTGTCATTC<br>TATTCTGGGGGGTGGGGTGGGGCAGGACAGCAAGGGGGAGGATTGGGAAGACA<br>ATAGGAG |
| 27 | exemplary EMCV IRES from Example 10<br>GTTATTTTCCACCATATTGCCGTCTTTTGGCAATGTGAGGGCCCGGAAACCTGGC<br>CCTGTCTTCTTGACGAGCATTCCTAGGGGTCTTTCCCCTCTCGCCAAAGGAATGC<br>AAGGTCTGTTGAATGTCGTGAAGGAAGCAGTTCCTCTGGAAGCTTCTTGAAGACA<br>AACAACGTCTGTAGCGACCCTTTGCAGGCAGCGGAACCCCCCACCTGGCGACAG<br>GTGCCTCTGCGGCCAAAAGCCACGTGTATAAGATACACCTGCAAAGGCGGCACA<br>ACCCCAGTGCCACGTTGTGAGTTGGATAGTTGTGGAAAGAGTCAAATGGCTCTCC<br>TCAAGCGTATTCAACAAGGGGCTGAAGGATGCCCAGAAGGTACCCCATTGTATG<br>GGATCTGATCTGGGGCCTCGGTGCACATGCTTTACATGTGTTTAGTCGAGGTTAA<br>AAAAACGTCTAGGCCCCCCGAACCACGGGGACGTGGTTTTCCTTTGAAAAACAC<br>G |
| 28 | exemplary 2A coding sequence from Example 10<br>GCTCCAGTAAAGCAGACTCTAAACTTCGATCTTCTCAAGCTCGCTGGAGATGTTG<br>AGAGCAACCCAGGTCCA |

What is claimed is:

1. A method for reducing tumor growth in a subject having a cancer, said method comprising intratumorally injecting to said subject an AAV vector comprising either a nucleic acid sequence comprising SEQ ID NO: 12 encoding a VEGF-TRAP, or a nucleic acid sequence comprising SEQ ID NO: 12 encoding a VEGF-TRAP and SEQ ID NO: 6 encoding a soluble platelet factor 4 (sPF4), wherein said nucleic acid sequence is operably linked to a promoter and following the injection the expression of either VEGF-TRAP or VEGF-TRAP and sPF4 in said subject results in reduced tumor growth.

2. The method according to claim 1, wherein said cancer is selected from the group consisting of glioma, bladder cancer, breast cancer, colon cancer, melanoma cancer, liver cancer, lung cancer, ovarian cancer, prostate cancer, renal cell carcinoma, hemangioma and astrocytoma.

3. The method according to claim 2, wherein said cancer is glioma.

4. The method according to claim 2, wherein said cancer is colon cancer.

5. The method according to claim 3, wherein the AAV vector comprising a nucleic acid sequence comprising SEQ ID NO: 12 encoding a VEGF-TRAP.

6. The method according to claim 5, wherein said promoter is a CAG promoter.

7. The method according to claim 2, wherein said AAV vector further comprises a woodchuck post-transcriptional regulatory element (WPRE).

8. The method according to claim 2, wherein said AAV vector further comprises a bovine growth hormone polyadenylation sequence (BGHpA).

9. The method according to claim 7, wherein said AAV vector further comprises a bovine growth honnone polyadenylation, sequence (BGHpA).

10. The method according to claim 2, wherein said AAV vector has a serotype selected from the group consisting of AAV-6, AAV-7 and AAV-8.

11. The method according to claim 5, further comprising administering to said subject a chemotherapeutic agent selected from the group consisting of etoposide, vincristine, cisplatin, doxorubicin, camptothecin and carmustine.

12. A method for reducing tumor growth in a subject having glioma, said method comprising intratumorally injecting to said subject an AAV vector comprising a nucleic acid sequence comprising SEQ ID NO: 12 encoding a VEGF-TRAP, a woodchuck post-transcriptional regulatory element (WPRE), and a bovine growth hormone polyadenylation sequence (BGHpA), wherein said nucleic acid sequence is operably linked to a CAG promoter and following the injection the expression of VEGF-TRAP in said subject results in reduced tumor growth.

13. The method according to claim 12, wherein said AAV vector has a serotype selected from the group consisting of AAV-6, AAV-7 and AAV-8.

14. The method according to claim 12, further comprising administering to said subject a chemotherapeutic agent selected from the group consisting of etoposide, vincristine, cisplatin, doxorubicin, camptothecin and carmustine.

15. The method according to claim 12, further comprising administering radiation therapy to said subject.

* * * * *